US012702868B2

(12) United States Patent
Johnson et al.

(10) Patent No.: US 12,702,868 B2
(45) Date of Patent: Aug. 11, 2026

(54) ELECTRON BEAM RADIATION SYSTEM WITH COLLISION DETECTION FUNCTIONALITY

(71) Applicant: INTRAOP MEDICAL CORPORATION, Sunnyvale, CA (US)

(72) Inventors: Richard L. Johnson, Suffolk, VA (US); Michael F. Turk, Porter Ranch, CA (US)

(73) Assignee: INTRAOP MEDICAL CORPORATION

( * ) Notice: Subject to any disclaimer, the term of this patent is extended or adjusted under 35 U.S.C. 154(b) by 444 days.

(21) Appl. No.: 18/290,556

(22) PCT Filed: May 19, 2022

(86) PCT No.: PCT/US2022/030022

§ 371 (c)(1),
(2) Date: Nov. 14, 2023

(87) PCT Pub. No.: WO2022/246061

PCT Pub. Date: Nov. 24, 2022

(65) Prior Publication Data

US 2024/0245933 A1 Jul. 25, 2024

Related U.S. Application Data

(60) Provisional application No. 63/190,492, filed on May 19, 2021.

(51) Int. Cl.
*A61N 5/10* (2006.01)

(52) U.S. Cl.
CPC ......... *A61N 5/1048* (2013.01); *A61N 5/1045* (2013.01); *A61N 5/1078* (2013.01); (Continued)

(58) Field of Classification Search
CPC .. A61N 5/1048; A61N 5/1045; A61N 5/1078; A61N 2005/1089; A61N 2005/1094
See application file for complete search history.

(56) References Cited

U.S. PATENT DOCUMENTS 3,201,065 A 8/1965 Dunn
3,391,881 A 7/1968 Maltby
(Continued)

FOREIGN PATENT DOCUMENTS

CN 106267587 A 1/2017
EP 0 838 844 B1 7/2003
(Continued)

OTHER PUBLICATIONS

PCT/US2018/030897, Intraop Medical Corporation, International Search Report and Written Opinion, dated Sep. 6, 2018, 12 pgs.
(Continued)

*Primary Examiner* — Sean Luck
(74) *Attorney, Agent, or Firm* — Kagan Binder, PLLC

(57) ABSTRACT

The present invention relates to the field of electron beam machines, such as linear straight through machines, and methods used for therapeutic uses. More particularly, the present invention relates to electron beam machines that incorporate a rotary coupling system to easily attach and manually or automatically rotate field defining members such as applicators and/or shields to the electron beam machines. The rotary coupling systems also incorporate functionality to automatically detect collisions involving the electron beam machines such as between an electron beam machine and other equipment or a patient.

25 Claims, 51 Drawing Sheets

(52) U.S. Cl.
CPC ................. *A61N 2005/1089* (2013.01); *A61N 2005/1094* (2013.01)

(56) References Cited

U.S. PATENT DOCUMENTS

| | | | |
|---|---|---|---|
| 3,651,360 | A | 3/1972 | Sommeria |
| 3,820,035 | A | 6/1974 | Meddaugh |
| 3,852,610 | A | 12/1974 | McIntyre |
| 4,131,799 | A | 12/1978 | Stieber |
| 4,627,089 | A | 12/1986 | Menor et al. |
| 4,638,814 | A | 1/1987 | Spanswick |
| 4,882,741 | A | 11/1989 | Brown |
| 4,891,767 | A | 1/1990 | Rzasa et al. |
| 4,995,087 | A | 2/1991 | Rathi et al. |
| 5,072,123 | A | 12/1991 | Johnsen |
| 5,321,271 | A | 6/1994 | Schonberg et al. |
| 5,326,967 | A | 7/1994 | Herrmann et al. |
| 5,418,372 | A | 5/1995 | Schonberg et al. |
| 5,661,377 | A | 8/1997 | Mishin et al. |
| 5,745,545 | A | 4/1998 | Hughes |
| 5,933,523 | A | 8/1999 | Drisko et al. |
| 6,076,005 | A | 6/2000 | Sontag et al. |
| 6,078,036 | A | 6/2000 | Cook et al. |
| 6,087,664 | A | 7/2000 | Gripp et al. |
| 6,118,847 | A | 9/2000 | Hernandez-Guerra et al. |
| 6,137,893 | A | 10/2000 | Michael et al. |
| 6,346,966 | B1 | 2/2002 | Toh |
| 6,362,875 | B1 | 3/2002 | Burkley |
| 6,554,452 | B1 | 4/2003 | Bourn et al. |
| 6,690,965 | B1 | 2/2004 | Riaziat et al. |
| 6,864,633 | B2 | 3/2005 | Trail et al. |
| 6,871,993 | B2 | 3/2005 | Hecht |
| 7,312,461 | B2 * | 12/2007 | Lewellen ............. A61N 5/1001 424/9.34 |
| 7,339,320 | B1 | 3/2008 | Meddaugh et al. |
| 7,400,093 | B2 | 7/2008 | Salop et al. |
| 7,894,649 | B2 | 2/2011 | Fu et al. |
| 8,111,025 | B2 | 2/2012 | Whittum et al. |
| 8,198,587 | B2 | 6/2012 | Whittum et al. |
| 8,269,197 | B2 | 9/2012 | Goer et al. |
| 8,719,398 | B2 | 5/2014 | Qian et al. |
| 8,791,437 | B2 | 7/2014 | Felici et al. |
| 8,853,636 | B2 | 10/2014 | Perkins |
| 9,030,134 | B2 | 5/2015 | Whittum et al. |
| 9,040,945 | B1 | 5/2015 | Hayman |
| 9,257,253 | B1 | 2/2016 | Allen et al. |
| 9,308,395 | B2 | 4/2016 | Adler, Jr. et al. |
| 9,393,439 | B2 | 7/2016 | Goer |
| 9,746,581 | B2 | 8/2017 | Whittum et al. |
| 9,757,593 | B2 | 9/2017 | Adler et al. |
| 9,855,445 | B2 | 1/2018 | Mansfield |
| 10,071,264 | B2 | 9/2018 | Liger |
| 10,092,774 | B1 | 10/2018 | Vanderstraten et al. |
| 10,183,179 | B1 | 1/2019 | Smith et al. |
| 10,245,448 | B2 | 4/2019 | Heese |
| 10,307,618 | B2 | 6/2019 | Mansfield |
| 10,485,993 | B2 | 11/2019 | Goer et al. |
| 11,135,449 | B2 | 10/2021 | Johnson et al. |
| 11,285,341 | B2 | 3/2022 | Goer et al. |
| 2001/0042841 | A1 | 11/2001 | Lyons et al. |
| 2007/0003874 | A1 | 1/2007 | Yang |
| 2007/0102651 | A1 | 5/2007 | Yang |
| 2008/0131312 | A1 | 6/2008 | Kang et al. |
| 2008/0298553 | A1 | 12/2008 | Takahashi et al. |
| 2009/0054318 | A1 | 2/2009 | Kanegasaki et al. |
| 2009/0126760 | A1 | 5/2009 | Banerjee et al. |
| 2009/0254154 | A1 | 10/2009 | De Taboada et al. |
| 2009/0296885 | A1 | 12/2009 | Boeh et al. |
| 2009/0314590 | A1 | 12/2009 | Dagh et al. |
| 2010/0008467 | A1 | 1/2010 | Dussault et al. |
| 2010/0127169 | A1 | 5/2010 | Whittum et al. |
| 2010/0163726 | A1 | 7/2010 | Shimada et al. |
| 2010/0166294 | A1 | 7/2010 | Marrion et al. |
| 2011/0017920 | A1 | 1/2011 | Goer et al. |
| 2011/0049377 | A1 | 3/2011 | Morf et al. |
| 2011/0114838 | A1 | 5/2011 | Han et al. |
| 2014/0091238 | A1 | 4/2014 | Miyashita et al. |
| 2015/0174430 | A1 | 6/2015 | Felici et al. |
| 2016/0247656 | A1 | 8/2016 | Hemberg et al. |
| 2016/0287905 | A1 | 10/2016 | Liger |
| 2017/0225015 | A1 | 8/2017 | Thieme et al. |
| 2017/0281981 | A1 | 10/2017 | Mansfield |
| 2018/0133514 | A1 | 5/2018 | Mansfield |
| 2018/0161600 | A1 | 6/2018 | Bowman et al. |
| 2019/0022407 | A1 | 1/2019 | Abel et al. |
| 2019/0022409 | A1 | 1/2019 | Vanderstraten et al. |
| 2019/0022411 | A1 | 1/2019 | Parry et al. |
| 2019/0022416 | A1 | 1/2019 | Smith et al. |
| 2019/0022417 | A1 | 1/2019 | Heese |
| 2019/0022422 | A1 | 1/2019 | Trail et al. |
| 2019/0029101 | A1 | 1/2019 | Roecken et al. |
| 2019/0054318 | A1 | 2/2019 | Goer et al. |
| 2019/0060667 | A1 | 2/2019 | Vanderstraeten et al. |
| 2019/0209870 | A1 | 7/2019 | Ueno et al. |
| 2019/0255361 | A1 | 8/2019 | Mansfield |
| 2019/0272969 | A1 | 9/2019 | Allen |
| 2019/0314645 | A1 | 10/2019 | Ciresianu et al. |
| 2020/0054896 | A1 | 2/2020 | Johnson et al. |
| 2020/0086144 | A1 | 3/2020 | Goer et al. |
| 2021/0124178 | A1 | 4/2021 | Matsunobu et al. |
| 2022/0323793 | A1 | 10/2022 | Brooks et al. |
| 2023/0039675 | A1 | 2/2023 | Turk et al. |

FOREIGN PATENT DOCUMENTS

| | | | |
|---|---|---|---|
| EP | 2 316 528 | A1 | 5/2011 |
| GB | 2 127 173 | A | 4/1984 |
| WO | 2012/025719 | A1 | 3/2012 |
| WO | 2013/134597 | A1 | 9/2013 |
| WO | 2013175517 | A1 | 11/2013 |
| WO | 2014/116868 | A1 | 7/2014 |
| WO | 2017/151763 | A1 | 9/2017 |
| WO | 2017/173443 | A1 | 10/2017 |
| WO | 2018/204649 | A1 | 11/2018 |
| WO | 2019/016249 | A1 | 1/2019 |
| WO | 2019/016301 | A1 | 1/2019 |
| WO | 2019/016305 | A1 | 1/2019 |
| WO | 2019/016312 | A1 | 1/2019 |
| WO | 2019/016326 | A1 | 1/2019 |
| WO | 2019/018341 | A1 | 1/2019 |
| WO | 2019/018376 | A1 | 1/2019 |
| WO | 2019/018813 | A1 | 1/2019 |
| WO | 2020/018904 | A1 | 1/2020 |
| WO | 2020035615 | A1 | 2/2020 |
| WO | 202105035 | A1 | 3/2021 |
| WO | 2021050535 | A1 | 3/2021 |
| WO | 2021108375 | A1 | 6/2021 |

OTHER PUBLICATIONS

PCT/US2017/020191, Intraop Medical Corporation, International Search Report and Written Opinion, dated May 24, 2017, 12 pages.
PCT/US2020/049925, Intraop Medical Corporation, International Search Report and Written Opinion, Feb. 10, 2021, 19 pgs.
Arvind Jain et al., Design and Operating Experience of Triode Electron Guns for Industrial Electron Accelerators, WEPMA011II, APAC 2007, Raja Ramana Center for Advanced Technology (RRCAT), Indore, India, pp. 348-350.
NanoDot™-Dosimetry Badges | Landauer,https://www.landauer.corn/product/nanodot, (2019) pp. 1-2.
Keane, MD, et al., "Intraoperative Radiotherapy in the Era ofIntensive Neoadjuvant Chemotherapy and Chemoradiotherapy for Pancreatic Adenocarcinoma American Journal of Clinical Oncology, vol. 00, No. 00 (2016), pp. 1-6."
Balter et al., "Anniversary Paper: A sampling of novel technologies and the role of medical physicists in radiation oncology" Med. Phys. 35 (12), Dec. 2008, pp. 5641-5652.
Casali et al, "An electron beam imaging system for quality assurance in IORT" Nucl. Instr. and Meth. in Phys. Res. B 213 (2004) pp. 616-620.
Palta, Ph.D., et al., "Intraoperative Electron Beam Radiation Therapy: Technique, Dosimetry, and Dose Specification: Report Task of

(56) References Cited

OTHER PUBLICATIONS

Force 48 of the Radiation Therapy Committee, American Associate of Physicists in Medicine" Int. J. Radiation Oncology Biol. Phys., vol. 33, No. 3, (1995) pp. 725-745.
Radiation Products Design, Inc., Periscopic Viewer, May 27, 2017, pp. 1-4.
Beddar et al., "Intraoperative radiation therapy using mobile electron linear accelerators: Report of AAPM Radiation Therapy Committee Task Group No. 72" Med. Phys. 33, (2006) pp. 1476-1489.
Nakagawa et al., "Dosimetry of leakage doses from a mobile accelerator for IORT and legal issues for its clinical use in Japan" Int J Clin Oncol (1999) 4, pp. 215-219.
Willett et al, Intraoperative Radiation Therapy: Journal of Clinical Oncology, vol. 25, No. 8, (2007) pp. 971-977.
R.M. Wilenzick, Department of Radiation Therapy, Alton OchsnerMedical Foundation, W.S. Kubricht, Jr., et al, Mary Bird Perkins Radiatio Treatment Center, "Evaluation of a Commercial ApplicatorSystem for Intraoperative Radiotherapy (1985) pp. 1-20."
K.R. Hogstrom, et al., "Design of metallic electron beam cones foran intraoperative therapy linear accelerator" Int. J. Radiat. Oncol. Biol. Phys. 18, (1990) pp. 1223-1232.
J. R. Palta and N. Suntharalingam, "A nondocking intraoperativeelectron beam applicator system" Int. J. Radiat. Oncol. Biol. Phys. 17, (1989) pp. 411-417.
C. E. Nelson, et al., "The dosimetric properties of an intraoperative radiation therapy applicator system for a Mevatron-80" Med. Phys. 16, ( 1989) pp. 794-799.
Ravichandran et al., "Diamond detector in absorbed dose measurements in high-energy linear accelerator photon and electron beams", Journal of Applied Clinical Medical Physics, vol. 17, No. 2, 2016, pp. 291-303.
IntraOp, Mobetron® 2000 Product Specification (Sep. 2016) pp. 1-16.
McCullough, et al., Technical Notes "The dosimetric properties of an applicator system for intraoperative electron-beam therapy utilizinga Clinac-18 accelerator" Med. Phys. vol. 9, No. 2 (Mar. 21/ Apr. 1982) pp. 261-268.
H. Kharrati, et al., "Design of a non-docking intraoperative electron beam applicator system" Radiotherapy and Oncology 33(1) (1994) pp. 80-83.
M.J. Day, B.A., et al., "The 4 MeV Linear Accelerator at NewcastleUpon Tyne" Brit. J. Radio!. 31 (1958) pp. 669-682.
M. Weissbluth, et al., The Stanford Linear Accelerator "II. Installation and Physical Measurements" Radiology, 72 (2) (1959) pp. 242-253.
Thwaites et al., "Back to the future: the history and development of the clinical linear accelerator", Phys. Med. Biol. 51 (2006) R343-R362.
Jones, "Apparatus, Technique and Dosimetry of Intraoperative Electron Beam Therapy" Vaeth JM, Meyer JL (eds): The Role of High Energy Electrons in the Treatment of Cancer. 25th Annual San Francisco Cancer Symposium, Feb. 1990. Front Radiat Ther Oncol. Basel, Karger, vol. 25 (1991) pp. 233-245.
Varian, SIP Data Sheet, Linatron XP 950 kV Portable X-Band X-Ray Source (May 2016) pp. 1-2.
Almond et al., "The calibration and use of plane-parallel ionization chambers for dosimetry of electron beams: An extension of the 1983 AAPM protocol report of AAPM Radiation Therapy Committee Task Group No. 39" Medical Physics vol. 21, No. 8, (1994) pp. 1251-1260; doi: 10.III8/I.597359.
EP 211537748.5, Intraop Medical Corporation, Extended European Search Report, search completed Apr. 23, 2021, 5 pages.
McLaughlin, David, "Energy spectra comparisons for matched clinical electron beams on Elekta linear accelerators using a permanent magnet spectrometer" (2013). LSU Master's Theses, pp. 1-173 103; https://digitalcommons.lsu.edu/gradschool_theses/ 103.
Agostinelli et al, "On-line optimization of instraoperative electron beam radiotherapy of the breast", Radiotherapy and Oncology xxx (2012) xxx-xxx, 1-5, doi:10.1016/j.radonc.2012.01.009.
Wambersi et al., "Medical Applications of Electron Linear Accelerators" In: Turner S (ed) CERN Accelerator School (CAS): Cyclotron, linacs and their applications, CERN 96-02, (1996) CERN, Geneva, pp. 229-248.
AAPM Report No. 63, Radiochromic Film Dosimetry, "Radiochromic film dosimetry: Recommendations of AAPM Radiation Therapy Committee Task Group 55" (1998), pp. 1-25, Reprinted from Medical Physics, vol. 25, Issue II, Nov. 1998.
Price et al., "In vivo dosimetry with optically stimulated dosimeters and RTQA2 radio chromic film for Intraoperative radiotherapy of the breast" Medical Physics 40 (9), pp. 091716-1-091716-9 (2013); doi: 1O.II18/1.4819825.
Tabata, "Backscattering of Electrons from 3.2 to 14 MeV*", Postprint, re-edited for inclusion in T. Tabata, edited with commentary, The Collected Works of Tatsuo Tabata vol. 3, IDEA-TR 7 (2017), of the paper published in the Physical Review, vol. 162, Issue 2, Oct. 10, 1967, pp. 336-347 (doi:IO.II03/PhysRev.162.336).
Kenneth F. Koral and Allan J. Cohen, "Empirical Equations for Electron Backscattering Coefficients, NASA Technical Note", NASA TN D-2909, pp. 1-19 (1965); https://ntrs.nasa.gov/search.jsp?R~19650017673 2019-06-20TI2:37:48+00:00Z.
Bengt E. Bjarngard, et al., "Electron scattering and collimation system for a 12-MeV linear accelerator", Med. Phys. vol. 3, No. 3, May/Jun. 1976 pp. 153-158.
Sung-Joon Ye, et al., "Monte Carlo techniques for scattering foil design and dosimetry in total skin irradiations", Med. Phys. 32 (6), Jun. 2005, pp. 1460-1468.
Prof.P.G.Mahajan et al., "Basic Operation & Applications of Van de Graaff Generator" IJSRE vol. 05, Issue 05, May 2017, pp. 6395-6399; DOI: http://dx.doi.org/10.18535/ijsre/v5i05.04.
Karzmark, "Advances in linear accelerator design for radiotherapy" Medical Physics, vol. II, No. 2, Mar./ Apr. 1984, pp. 105-128.
Purdy et al., "Dual Energy X-Ray Beam Accelerators in Radiation Therapy: An Overview" Nuclear Instruments and Methods in Physics Research BIO/II (1985) pp. 1090-1095.
D. Goer, Linear Accelerator, Medical , Encyclopedia of Medical Devices and Instrumentation, 1988, John Wiley & Sons, vol. 3, pp. 1772-1800.
Muluta et al., "Intraoperative Electron Radiotherapy (IOERT) as an Alternative to Standard Whole Breast Irradiation: Only for Low Risk Subgroups?" Breast Care (2014) 9, pp. 102-106; DOI: 10.II59/ 000362392.
Silverstein et al., "Intraoperative Radiation Therapy: A Critical Analysis of the ELIOT and TARGIT Trials. Part 1-Eliot" Ann Surg Oncol, Jun. 23, 2014, Published online: Aug. 27, 2014, pp. 1-6; DOI 10.1245/ sl0434-014-3998-6.
Silverstein et al., "Intraoperative Radiation Therapy: A Critical Analysis of the ELIOT and TARGIT Trials. Part 2-TARGIT" Ann Surg Oncol, Jun. 23, 2014, Published online: Aug. 20, 2014, pp. 1-6; DOI 10.1245/sl0434-014-3999-5.
Meurk et al., "The Mobetron: A New Concept for IORT" Vaeth JM ( ed): Intraoperative Radiation Therapy in the Treatment of Cancer, Front Radiat Ther Oncol. Basel, Karger, 1997, vol. 31 , pp. 65-70.
Khan et al., AAPM Report No. 32, Clinical electron-beam dosimetry: Report of AAPM Radiation Therapy Committee Task Group No. 25, Med. Phys., vol. 18, Issue 1, (1991) pp. 73-109.
Jean Bourhis, MD, et al., "Clinical translation of FLASH radiotherapy: Why and how?" Radiotherapy and Oncology, 139, Oct. 2019, pp. 11-17.
Kutcher et al., "Comprehensive QA for radiation oncology: Report of AAPM Radiation Therapy Committee Task Group 40," Med. Phys. 21 (4) Apr. 1994, pp. 581-618.
Klein et al., "Task Group 142 Report: Quality Assurance of Medical Accelerators," Med. Phys. 36 (9) Sep. 2009, pp. 4197-4212.
Felici et al., "Transforming an IORT Linac Into a FLASH Research Machine: Procedure and Dosimetric Characterization," Frontiers in Physics, (2002) vol. 8, Art 374, pp. 1-11.
PCT/US2022/30022, Notification of Transmittal of the International Search Report and the Written Opinion of the International Searching Authority, Or the Declaration, Aug. 24, 2022, 9 pgs.
D. Bhattacharjee et al., Development of Electron Guns for Linacs and DC Accelerator, J. of Physics: Conference Series 390 (2012) 012071.

(56) References Cited

OTHER PUBLICATIONS

S. Mahadevan et al., "Improved Version of the Triode Electron Gun", Nuclear Instruments and Methods in Physics Research A, vol. 438 (1999) pp. 573-576.
David H. Whittum, "Microwave Electron Linacs for Oncology," Reviews of Accelerator Science and Technology, vol. 2 (2009) pp. 63-92.
C.J. Karzmark et al. "Treatment Beam Production," Medical Electron Accelerators, McGraw-Hill, New York, (1993) Ch. 8, cover page, contents v-xii, pp. 137-156.
C.J. Karzmark et al. "Multi-X-Ray Energy Accelerators," Medical Electron Accelerators, McGraw-Hill, New York, (1993) Ch. 11, cover page, contents v-xii, pp. 189-199.
Esplen et al., "Physics and biology of ultrahigh dose-rate (FLASH) radiotherapy: A topical review," Institute of Physics and Engineering in Medicine, Physics in Medicine and Biology (2020) vol. 65, No. 23, pp. 1-107.
Rahman et al., "Electron FLASH Delivery at Treatment Room Isocenter for Efficient Reversible Conversion of a Clinical LINAC," Int J Radiat Oncol Biol Phys. (2021) 1;110(3):872-882. doi: 10.1016/j.ijrobp.2021.01.011. Epub Jan. 11, 2021.
Grosswendt, "Determination of Electron Depth-Dose Curves for Water, ICRU Tissue, and PMMA and Their Application to Radiation Protection Dosimetry," Radiation Protection Dosimetry (1994) vol. 54, No. 2, pp. 85-97.
Peter R. Almond et. al., "AAPM's TG-51 protocol for clinical reference dosimetry of high-energy photon and electron beams," Med. Phys. 26 (9), Sep. 1999, pp. 1847-1870.
PCT/US2020/061963, Intraop Medical Corporation, International Search Report and Written Opinion, Feb. 16, 2021, 10 pgs.
EP 20862319.9, Intraop Medical Corporation, Extended European Search Report, search completed Aug. 18, 2023, 7 pgs.
EP 20894405.8, Intraop Medical Corporation, Extended Euorpean Search Report, search completed Nov. 15, 2023, 6 pages.

* cited by examiner 12
90
88
86
93
89
47
98
96
95
38
34
84
36
81
80
83
31
82
32
78
64
76
49
26
70
68
65
73
72
66

12
90
88
86
93
89
98
96
95
84
34
36
38
81
80
83
31
82
49
78
78
32
72
76
64
68
73
26
70
65
66

95
96
98
210
214
216
220
282
202
260
290
222
224
312
213
226
314
306
α
alpha
240
211
248
262
242
244
209
215
86
122
131
124
130
88
138
141
136

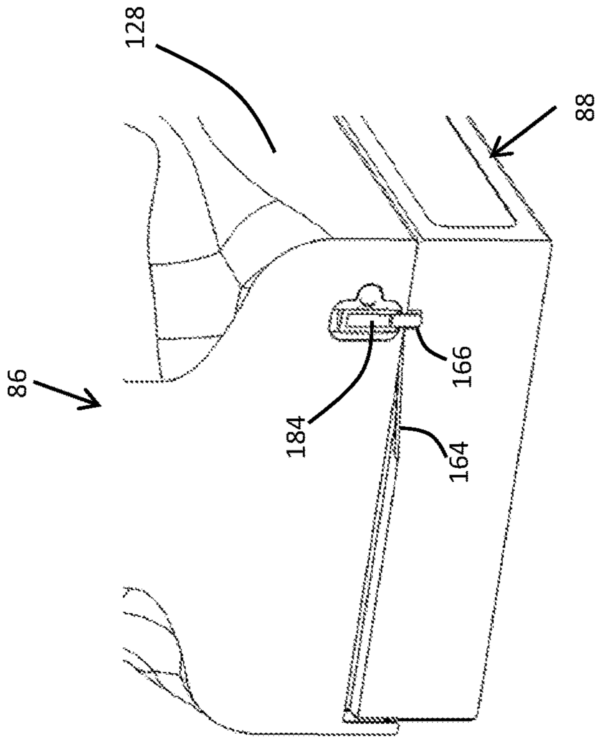
Fig. 27
Fig. 26
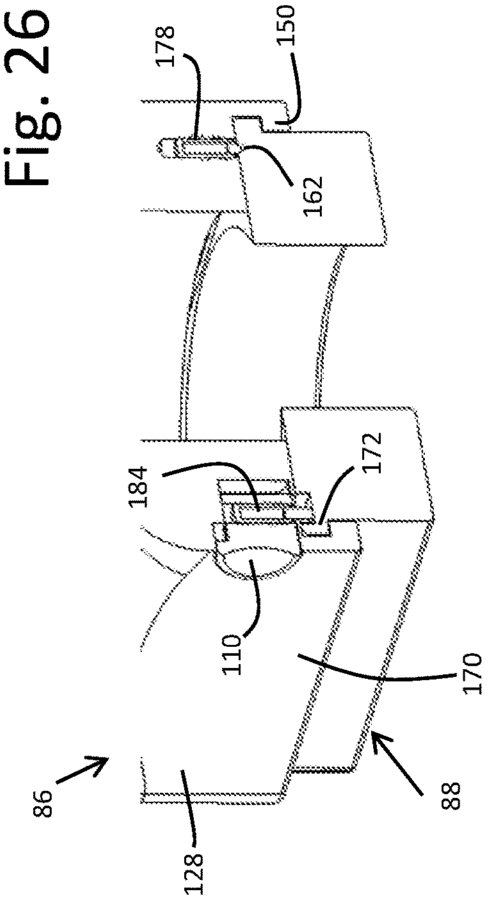
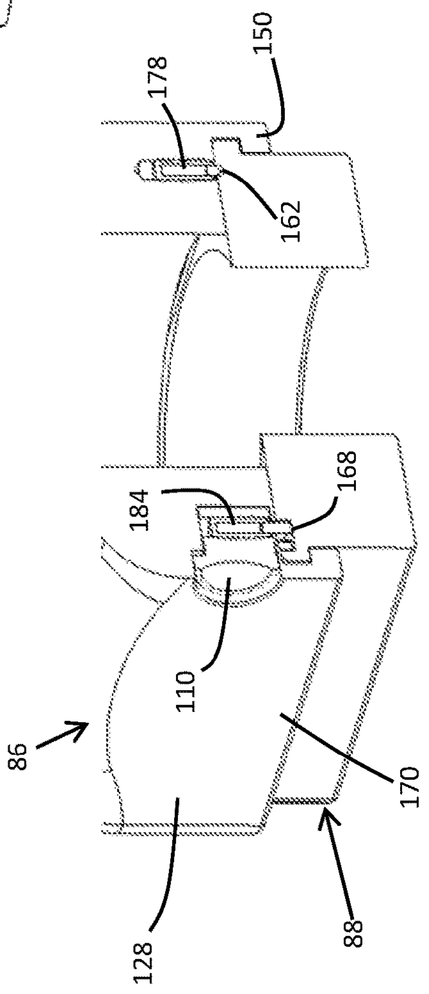
Fig. 28
128
88
86
184
166
164
178
150
162
184
172
110
170
86
88
128
178
150
162
184
168
110
86
170
128
88

380
398
396
349
348
404
406
238
403
402
396
220

95
220
228
284
232
260
262
240
244
242
238
226
98
96
222
228
230
232

Fig. 37
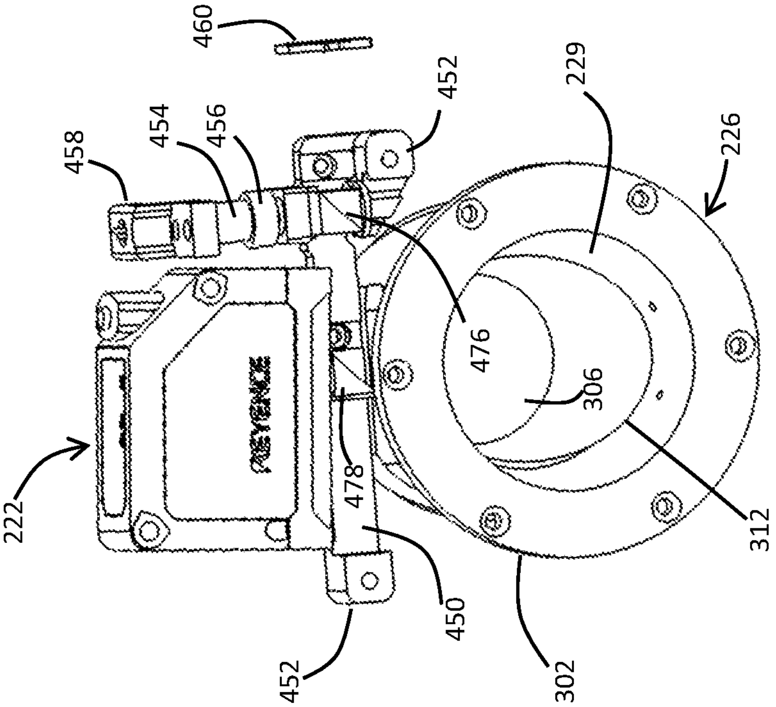
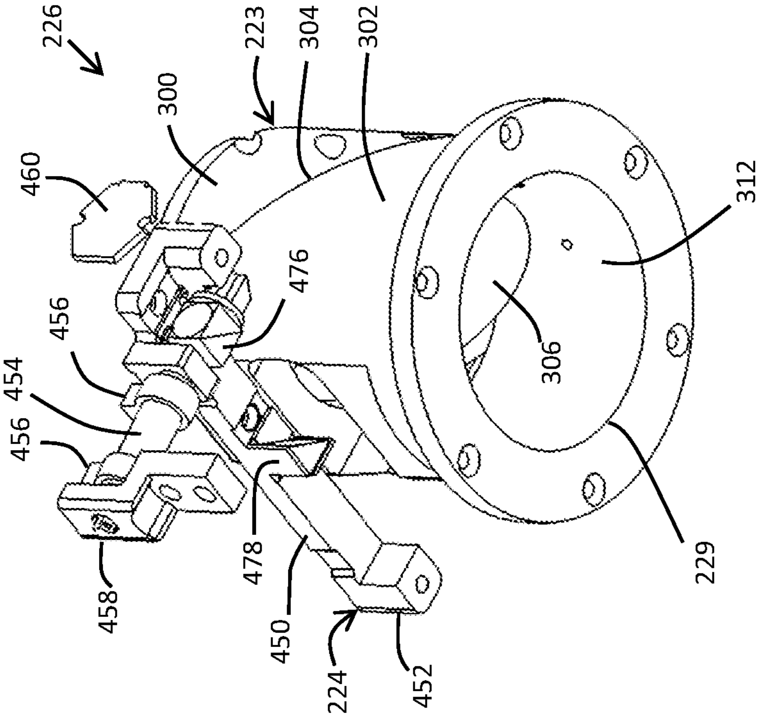
Fig. 36

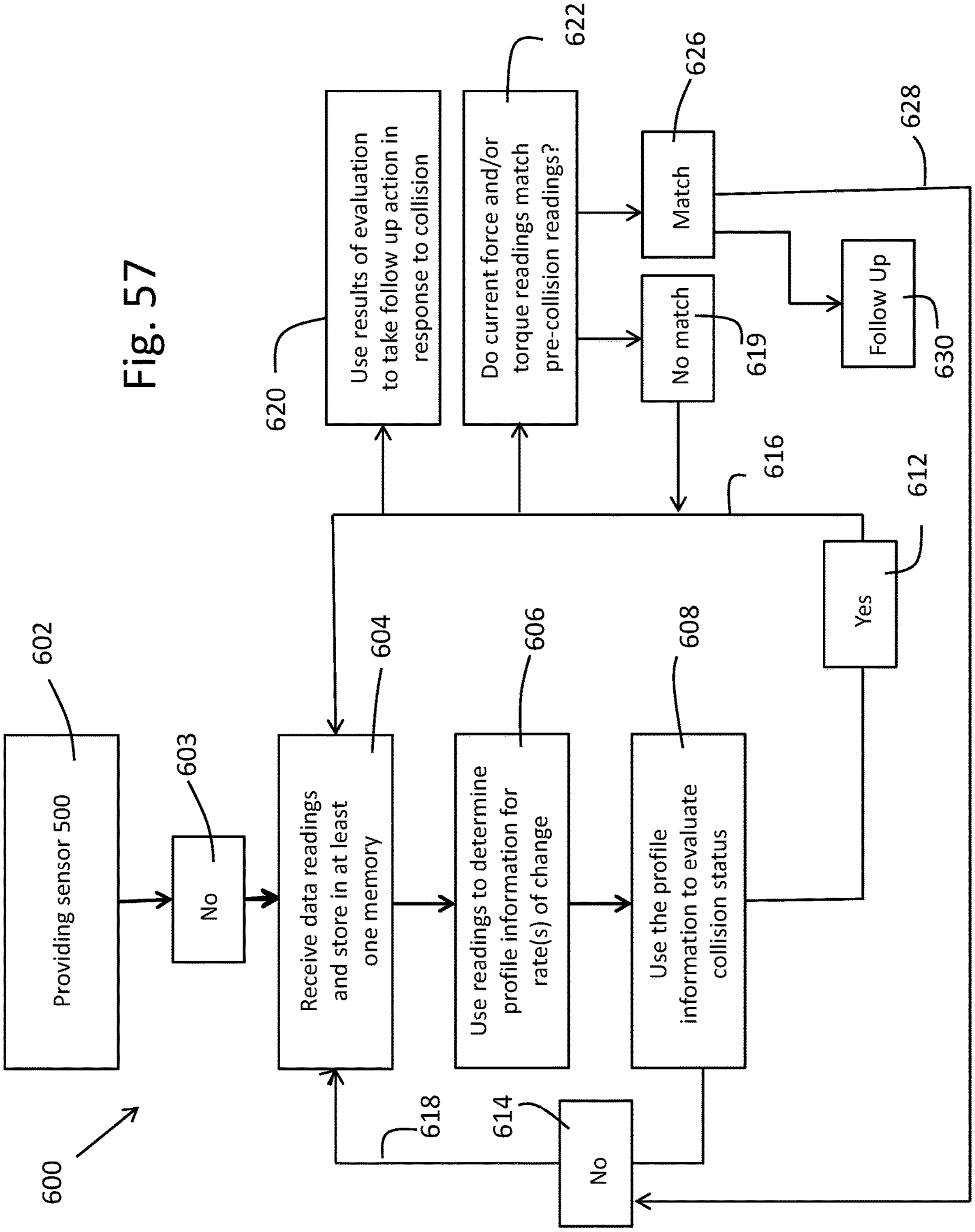

Fig. 57
600
Providing sensor 500
602
No
603
Receive data readings and store in at least one memory
604
Use readings to determine profile information for rate(s) of change
606
Use the profile information to evaluate collision status
608
Yes
612
No
614
616
618
No match
619
Use results of evaluation to take follow up action in response to collision
620
Do current force and/or torque readings match pre-collision readings?
622
Match
626
628
Follow Up
630

ELECTRON BEAM RADIATION SYSTEM WITH COLLISION DETECTION FUNCTIONALITY

PRIORITY

This application claims priority to International Application No. PCT/US2022/030022, filed on May 19, 2022, which in turn claims the benefit of U.S. Provisional Patent Application No. 63/190,492 filed on May 19, 2021, entitled "ELECTRON BEAM RADIATION SYSTEM WITH COLLISION DETECTION FUNCTIONALITY," the disclosure of which are hereby incorporated by reference in their respective entireties for all purposes.

TECHNICAL FIELD

The present invention relates to the field of electron beam machines, such as linear straight through machines, and methods used for therapeutic uses. More particularly, the present invention relates to electron beam machines that incorporate a rotary coupling system to easily attach and manually or automatically rotate field defining members such as applicators and/or shields to the electron beam machines. The rotary coupling systems also incorporate functionality to automatically detect collisions involving the electron beam machines such as between an electron beam machine and other equipment or a patient.

BACKGROUND

Electron beam ("ebeam") radiotherapy is a type of external beam therapy in which electrons are directed to a target site on a patient in order to carry out a desired treatment. Features of the electron beam such as energy, dose rate, dose, treatment duration, field size, field shape, distance to the patient, and the like are factors in carrying out treatments.

Electron beam linear accelerator-based machines are one type of electron beam machine used in electron beam radiotherapy. The MOBETRON electron beam machine available from IntraOp, Sunnyvale, CA, is an example of a mobile, self-shielded, electron beam linear accelerator (LINAC) machine useful in electron beam radiotherapy.

A typical electron beam LINAC machine uses a linear accelerator to accelerate a supply of relatively lower energy electrons. The electrons may be sourced by thermionic emission from cathodes. The electrons are injected into the accelerator and gain energy as they travel down the structure. The power needed to accelerate the electrons often is supplied by magnetrons or klystrons. Downstream of the linear accelerator, the energized electron stream is fed to a collimator. The collimator helps to narrow the beam of electrons such as to cause the electrons to become more aligned in a specific direction as well as to cause the spatial cross section of the beam to become smaller. A collimator also may help to homogenize the beam energy across its cross-section. Downstream from the collimator, one or more additional components may be used to further shape, define, and/or homogenize the beam. Examples of such field defining components include applicators and shields. Applicators or shields may be used singly or in combination.

It is desirable for electron beam machines to have positioning degrees of freedom that include rotation of beam shaping components. For example, it might be desired that an entire collimator be able to rotate at least +/−90°. Some machine designs to not allow rotation to be incorporated into machine function unless cumbersome components are added. For example, some conventional accelerators designed to deliver electrons are also expected to deliver high energy x-rays. The consequence is that the head or collimator is heavy, as it contains either multi-leaf collimators or tungsten collimators to define the X-Y treatment field. Such collimation devices must be thick enough to attenuate the x-ray radiation to 5% or less. The collimation devices also must allow field sizes of 25 to 40 cm at the patient plane. Thus, conventional collimators are too heavy to rotate without motor assistance. The head rotation also is limited due to use of cables needed to run the motors. Rotation can also interfere with how distance detection, illumination, and electron beam aiming strategies can be implemented. Better strategies to incorporate rotation functionality into electron beam LINAC machines are desired.

When used to generate electrons, field defining components such as applicators and/or shields made of plastic or metal, are attached to the collimator. Historically, electron beam LINAC machines may have had either a permanent or detachable mount to accept either electron applicators or x-ray shadow blocks. The wide-spread introduction of multileaf collimators eliminated the need for a shadow block tray attachment, but a detachable mount to attach electron applicators is still required. Without a mount, the electron applicators would be too long and awkward to use. It often is desirable to limit or otherwise define the shape of the electron beam field emitted from an electron beam LINAC machines. One strategy to accomplish this is by placing shields with aperture of appropriate size and shape downstream from the collimator such as at end of the applicator. Better strategies for mounting, de-mounting, and orienting applicators and shields are desired.

It often is desirable to illuminate a treatment site so that electron beam (also "ebeam") machine can be aimed accurately, so that the progress of a treatment can be monitored, and the like. Some conventional units generally use an incandescent light bulb that is positioned just outside the collimator. When the field light is activated, the light turns on and a mirror is moved in position to reflect the light on the target surface. Because of the relatively large light bulb to target surface distance, there is penumbra of 2-5 mm. The positioning of such a light bulb also can interfere with potential rotational positioning strategies. Better techniques to illuminate target sites without interfering with machine positioning are desired.

Treatments require that the electron beam LINAC machine be positioned at an accurate distance from the treatment site. Distance can affect the dose, ebeam energy, dose rate, and field size delivered to the target site. Some conventional strategies have used distance indicators that are optical projections of a scale. Such a projected scale has the potential to be accurate at the isocenter distance, but is less accurate at shorter and longer distances. Also, such devices can be affected by rotational positioning.

During positioning and/or use of an electron beam radiation system prior to, during, and/or after treatment of the patient, it is possible that there could be undesirable contact or collision between the system and other equipment or the patient. Rapid detection of a collision is desirable. When a collision occurs, it would be desirable for at least some follow up action(s) to be taken quickly and automatically. For example, it would be desirable for the relative motion between the machine and the other equipment or the patient to be stopped quickly. Improved strategies to detect and respond to collisions are desired to further enhance the safety and efficacy of treatments.

SUMMARY OF THE INVENTION

The present invention relates to linear, straight through electron beam machines that incorporate a rotary coupling system to easily attach and manually or automatically rotate field defining members such as applicators and/or shields to the electron beam machines. The rotary coupling systems also incorporate functionality for using different kinds of optical signals to automatically provide illumination, reference mark projection, and/or distance detection. The optical signals generated downstream from heavy collimator components and are transmitted along the central axis of the field defining elements so that function and accuracy are maintained as the components rotate. The principles of the present invention can be used with respect to any kind of ebeam machine. For purposes of illustration, the principles of the present invention will describe the invention in the context of electron beam LINAC machines.

Rotational capabilities are provided by rotatably mounting field defining members downstream from the collimator. Collimator rotation is not needed, as field size and shape can be established using the field defining members. The rotary coupling system is attached downstream from the collimator and is easily detachable for servicing components located inside the collimator. In illustrative embodiments, the rotary coupling system continues the conical opening of the collimator to improve the homogeneity resulting from wall scattering, finally terminating in a cylindrical section. In many embodiments, cylindrical applicators that attach to the rotary coupling system help to reduce the opening of the distal end of the collimator to the diameter of the applicator that is attached.

The rotary coupling system allows field defining elements to be easily rotated manually or automatically in clockwise or counter clockwise directions. Desirably, the rotation axis may be the same as the beam centerline. Rotation is unlimited in either direction. Rotation can be indexed, though, such as to allow rotation in 2° increments, and the rotation can be locked to secure the applicator position when it is in a desired orientation. The rotation mechanism desirably has a rotary position sensor for feedback purposes.

Derm radiotherapy generally may require 15-25 treatments. The field size used for Derm applications might have shielding inserted at the end of the applicator to protect healthy tissue. Since a patient might not always be on the treatment table in the exact same position each day, applicator and/or shield rotation results in the ability to rapidly position the electron beam to the correct orientation on the patient. Manual rotation is preferable to motorized rotation as it is more reliable (no cables, no motors, no electronics needed), and the manual field defining member(s) can be positioned more rapidly than a motor-driven collimator.

As another advantage, some embodiments of the present invention incorporate features and functionality that allow automatic detection of collision status for which appropriate automated and/or manual follow up action can be taken. According to a preferred methodology, collision detection is accomplished by using a sensor to monitor the force and/or torque encountered by an electron beam system. The rate(s) of change of the sensed force and/or torque are used to evaluate whether a collision has occurred. In some embodiments, both the rates of change of force and/or torque are used to evaluate collision status in combination with the actual force and torque values. It has been found that incorporating rates of change of force and/or torque into collision analysis provides more reliable, more comprehensive, and even faster detection of a collision event as compared to relying only on the actual force and/or torque values.

In exemplary modes of practice, the magnitude of the rate of change of force and/or torque as a function of time is relatively low in the absence of a collision. However, upon a collision the magnitude of the rate of change tends to increase abruptly in association with the collision event. Keeping in mind that the terminology “magnitude” is associated with the absolute value of the rate of change, either an upward (positive) or downward (negative) spike in the rate of change profile can occur in association with a collision. Because magnitude is associated with the absolute value of this response, positive and negative spikes in the rate of change cause a corresponding, positive spike in the magnitude.

In representative modes of practice, the magnitude of the rate of change of force or torque is relatively low in the absence of a collision regardless of the orientation of the electron beam machine. However, the magnitude tends to increase sharply upon a collision regardless of the orientation of the electron beam machine. Consequently, a collision can be indicated when the magnitude of the rate of change of force or torque exceeds a suitable threshold. The threshold is easy to set empirically. Force and torque values can be sensed and the rate of change of these determined as an electron beam machine is moved throughout its range of motion in the absence of collisions. This allows the magnitude range for normal operation (i.e., no collisions) to be determined. The threshold can then be set at a suitable level above this normal range.

If the threshold is set too close to the normal range, it is possible that normal fluctuations in the magnitude of the rate of change profile could exceed the threshold. If the threshold is set to far from the normal range, then it is possible that the magnitude spike associate with a collision could be missed. Balancing these concerns, it is desirable to set a threshold that is in the range from 5% to 100% higher, preferably 5% to 25% higher, than the peak magnitude of the rate of change profile. This approach sets a threshold for a magnitude spike to signal a collision. For reasons discussed further below, it also is desirable to set a maximum ceiling limit for when a magnitude spike signals a collision. As discussed below, some interactions with the equipment, such as removing or inserting an applicator, may cause spikes in magnitude much greater than those associated with collisions.

Consequently, detecting collisions when using information indicative of the rate of change of force and/or torque is easier than relying on actual (or nominal) force and torque values because the magnitude of the rate of change of force and/or torque tends to be consistently low regardless of machine orientation or set up, and yet the magnitude of the rate of change spikes sharply in the event of a collision regardless of machine orientation or set up. In contrast, the normal baselines for force and torque are highly variable as a function of machine orientation and setup. It generally would not be suitable to set a single collision threshold specification if relying only on actual force and/or torque values due to this variation, yet a single threshold specification (which could encompass a single value threshold or a threshold range to account for component replacement, service, maintenance, or the like, as further discussed below with respect to a threshold specification range)

Using rates of change of both torque and force in collision detection is advantageous in preferred modes of practice. Generally, the rate of change of torque can be more sensitive to a collision event, but there are some collision events for which the rate of change of force is a better indicator of the collision. For example, many commercially available force and torque sensors have a central axis. Torque sensing tends to be more sensitive than force sensing for collisions that are not coincident with the central axis. On the other hand, force sensing would tend to be more sensitive than torque sensing for collisions that are substantially coincident with the central axis of a sensor having such an axis.

While the rate of change information is useful to detect collisions, the actual force and torque values also are helpful to evaluate collision status in the practice of the present invention. In some modes of practice, for example, continuing to sense and evaluate the actual force and/or torque values after a collision event can be used to determine that a collision event continues or has ended and normal status (no collision) is restored. As the actual force and torque values continue to be sensed, these can be compared to the historic values of torque and/or force that were sensed in a suitable window (which could be a fraction of a second or a few seconds in some modes of practice) just prior to the collision. When actual force and/or torque values sensed after the collision are sufficiently similar to the historical pre-collision values, the system can determine that the collision event has ended. This strategy integrates evaluation of current force and/or torque values, historical force and/or torque values, and rate(s) of change of force and/or torque to evaluate collision status.

As another advantage, using information indicative of the rates of change of force and/or torque to evaluate collision status overcomes calibration issues when relying only on actual force or torque values for collision detection. Proper force and/or torque values (i.e., values in the absence of a collision) can vary considerably during the course of docking, treatment, and undocking for a particular patient as well as among docking, treatment, and undocking for different patients. If one were to only rely on force and torque values, appropriate baseline values for a multitude of different circumstances would have to be determined and frequently calibrated. It would be difficult as a practical matter to determine the proper baseline values for torque and/or force at any point in time with a strategy relying only on actual torque and force values. In other words, setting a threshold for a collision is difficult when the threshold constantly changes with changing circumstances.

In contrast, using rates of change of force and/or torque is substantially universal and robust to variations as orientation, position, angles, etc. of a machine are changed. Using rates of change uses relative relationships between pre and post-collision values, so calibration with respect to an actual baseline value of force and/or torque is not needed for accurate sensing. Using rates of change simplifies calibration, even avoids the need to calibrate or zero a sensor, and from one perspective is even self-calibrating since the rate of change is a relative measurement in practical effect, not an absolute measurement. In other words, using rates of change allows accurate collision detection even if there are variations in proper threshold values for force or torque. A normal rate of change profile is very consistent over a wide range of conditions so that a sudden positive or negative spike strongly correlates to a collision event.

In one aspect, the present invention relates to an electron beam radiation system that emits an electron beam at a surface, comprising:

a) an electron beam unit having a unit outlet, wherein the electron beam unit produces the electron beam and emits the electron beam from the unit outlet on a linear pathway leading from the unit outlet to the surface, wherein the linear pathway has a central axis;

b) at least a first field defining member positioned on the linear pathway downstream from the unit outlet, wherein the first field defining member has a through aperture comprising an inlet through which the electron beam enters the first field defining member through aperture as the electron beam travels along the linear pathway to the surface, and an outlet through which the electron beam leaves the first field defining member through aperture as the electron beam travels along the linear pathway to the surface; and c) a rotary coupling system that rotatably couples at least the first field defining member to an upstream component of the electron beam unit such that the first field defining member is rotatable on demand around a rotational axis independent of rotation of the upstream component, wherein the rotary coupling system comprises a through aperture, an inlet through which the electron beam enters the rotary coupling system through aperture as the electron beam travels along the linear pathway to the surface, and an outlet through which the electron beam leaves the rotary coupling system through aperture as the electron beam travels along the linear pathway to the surface.

In another aspect, the present invention relates to an electron beam radiation system that emits an electron beam at a surface, comprising:

a) an electron beam unit having a unit outlet, wherein the electron beam unit produces the electron beam and emits the electron beam from the unit outlet on a linear pathway leading from the unit outlet to the surface, wherein the linear pathway has a central axis;

b) at least a first field defining member positioned on the linear pathway downstream from the unit outlet, wherein the first field defining member has a through aperture comprising an inlet through which the electron beam enters the first field defining member through aperture as the electron beam travels along the linear pathway to the surface, and an outlet through which the electron beam leaves the first field defining member through aperture as the electron beam travels along the linear pathway to the surface;

c) a rotary coupling system that rotatably couples at least the first field defining member to an upstream component of the electron beam unit such that the first field defining member is rotatable on demand around a rotation axis independent of rotation of the upstream component, wherein the rotary coupling system comprises:

i) a through aperture comprising an inlet through which the electron beam enters the rotary coupling system through aperture as the electron beam travels along the linear pathway to the surface, and an outlet through which the electron beam leaves the rotary coupling system through aperture as the electron beam travels along the linear pathway to the surface;

ii) a tilted mirror mounted at a tilted angle in the through aperture of the rotary coupling system, wherein the mirror is tilted at a non-parallel and non-orthogonal angle relative to the linear pathway, wherein the mirror is at least partially reflective with respect to optical illumination in one or more wavelength bands of the electromagnetic spectrum in a range from 200 nm to 2000 nm, and wherein the tilted mirror is at least partially transparent to the electron beam such that at least a portion of the electron beam passes through the tilted mirror as the electron beam travels along the linear pathway; and iii) a window through which light can be directed at the tilted mirror from a location outside the through aperture of the rotary coupling system; and d) a light system positioned outside the through aperture of the rotary coupling system, wherein the light system produces a light signal and emits the light signal in a manner such that the light signal comprises light from one or more wavelength bands of the electromagnetic spectrum in the range from 200 nm to 2000 nm and is aimed at the tilted mirror through the window in a manner effective to be reflected downstream by the mirror along the linear pathway toward the surface.

In another aspect, the present invention relates to an electron beam radiation system that emits an electron beam at a surface, comprising:

a) an electron beam unit having a unit outlet, wherein the electron beam unit produces the electron beam and emits the electron beam from the unit outlet on a linear pathway leading from the unit outlet to the surface, wherein the linear pathway has a central axis;

b) at least a first field defining member positioned on the linear pathway downstream from the unit outlet, wherein the first field defining member has a through aperture comprising an inlet through which the electron beam enters the first field defining member through aperture as the electron beam travels along the linear pathway to the surface, and an outlet through which the electron beam leaves the first field defining member through aperture as the electron beam travels along the linear pathway to the surface;

c) a rotary coupling system that rotatably couples at least the first field defining member to an upstream component of the electron beam unit such that the first field defining member is rotatable on demand around a rotation axis independent of rotation of the upstream component, wherein the rotary coupling system comprises:

i) a through aperture comprising an inlet through which the electron beam enters the rotary coupling system through aperture as the electron beam travels along the linear pathway to the surface, and an outlet through which the electron beam leaves the rotary coupling system through aperture as the electron beam travels along the linear pathway to the surface;

ii) a tilted mirror mounted at a tilted angle in the through aperture of the rotary coupling system, wherein the mirror is tilted at a non-parallel and non-orthogonal angle relative to the linear pathway, wherein the mirror is at least partially reflective with respect to optical illumination in one or more wavelength bands of the electromagnetic spectrum in a range from 200 nm to 2000 nm, and wherein the tilted mirror is at least partially transparent to the electron beam such that at least a portion of the electron beam passes through the tilted mirror as the electron beam travels along the linear pathway; and iii) a window through which at least one optical signal can be directed at the tilted mirror from a location outside the through aperture of the rotary coupling system; and d) a light system positioned outside the through aperture of the rotary coupling system, wherein the light system produces a light signal and emits the light signal in a manner such that the light signal is aimed through the window at the tilted mirror in a manner effective to be reflected downstream along the linear pathway to the surface through the first field defining member through aperture.

In another aspect, the present invention relates to an electron beam radiation system that emits an electron beam at a surface, comprising:

a) an electron beam unit having a unit outlet, wherein the electron beam unit produces the electron beam and emits the electron beam from the unit outlet on a linear pathway leading from the unit outlet to the surface, wherein the linear pathway has a central axis;

b) at least a first field defining member positioned on the linear pathway downstream from the unit outlet, wherein the first field defining member has a through aperture comprising an inlet through which the electron beam enters the first field defining member through aperture as the electron beam travels along the linear pathway to the surface, and an outlet through which the electron beam leaves the first field defining member through aperture as the electron beam travels along the linear pathway to the surface;

c) a rotary coupling system that rotatably couples at least the first field defining member to an upstream component of the electron beam unit such that the first field defining member is rotatable on demand around a rotation axis independent of rotation of the upstream component, wherein the rotary coupling system comprises:

i) a through aperture comprising an inlet through which the electron beam enters the rotary coupling system through aperture as the electron beam travels along the linear pathway to the surface, and an outlet through which the electron beam leaves the rotary coupling system through aperture as the electron beam travels along the linear pathway to the surface;

ii) a tilted mirror mounted at a tilted angle in the through aperture of the rotary coupling system, wherein the mirror is tilted at a non-parallel and non-orthogonal angle relative to the linear pathway, wherein the mirror is at least partially reflective with respect to optical illumination in one or more wavelength bands of the electromagnetic spectrum in a range from 200 nm to 2000 nm, and wherein the tilted mirror is at least partially transparent to the electron beam such that at least a portion of the electron beam passes through the tilted mirror as the electron beam travels along the linear pathway; and iii) a window through which light can be directed at the tilted mirror from a location outside the through aperture of the rotary coupling system; and d) a light system positioned outside the through aperture of the rotary coupling system, wherein the light system produces a light signal and emits the light signal in a manner such that the light signal is aimed at the tilted mirror through the window in a manner effective to be reflected downstream along the linear pathway through the first field defining member to the surface, wherein the light system comprises a laser light source that produces a light signal comprising a visually observable optical reference mark that is reflected downstream through the first field defining member outlet onto the surface in a manner such that the location of the reference mark on the surface is indicative of how the electron beam is aimed at the surface.

In another aspect, the present invention relates to an electron beam radiation system that emits an electron beam at a surface, comprising:

a) an electron beam unit having a unit outlet, wherein the electron beam unit produces the electron beam and emits the electron beam from the unit outlet on a linear pathway leading from the unit outlet to the surface, wherein the linear pathway has a central axis;

b) at least a first field defining member positioned on the linear pathway downstream from the unit outlet, wherein the first field defining member has a through aperture comprising a central axis, an inlet through which the electron beam enters the first field defining member through aperture as the electron beam travels along the linear pathway to the surface, and an outlet through which the electron beam leaves the first field defining member through aperture as the electron beam travels along the linear pathway to the surface;

c) a rotary coupling system that rotatably couples at least the first field defining member to an upstream component of the electron beam unit such that the first field defining member is rotatable on demand around a rotation axis independent of rotation of the upstream component, wherein the rotary coupling system comprises:

i) a through aperture comprising an inlet through which the electron beam enters the rotary coupling system through aperture as the electron beam travels along the linear pathway to the surface, and an outlet through which the electron beam leaves the rotary coupling system through aperture as the electron beam travels along the linear pathway to the surface;

ii) a tilted mirror mounted at a tilted angle in the through aperture of the rotary coupling system, wherein the mirror is tilted at a non-parallel and non-orthogonal angle relative to the linear pathway, wherein the mirror is at least partially reflective with respect to optical illumination in one or more wavelength bands of the electromagnetic spectrum in a range from 200 nm to 2000 nm, and wherein the tilted mirror is at least partially transparent to the electron beam such that at least a portion of the electron beam passes through the tilted mirror as the electron beam travels along the linear pathway; and iii) a window through which at least one optical signal can be directed at the tilted mirror from a location outside the through aperture of the rotary coupling system; and d) a light system positioned outside the through aperture of the rotary coupling system, wherein the light system produces a composite light signal and emits the composite light signal in a manner such that the composite light signal is aimed at the tilted mirror in a manner effective to be reflected downstream along the linear pathway through the first field defining member toward the surface, wherein the light system comprises:

i) a laser light source that produces at least a portion of a first light signal comprising a visually observable optical reference mark.

ii) an LED light source that produces at least a portion of a second light signal comprising visually observable LED illumination; and iii) an optical combiner that combines at least the first and second light signals to provide the composite light signal in a manner such that the reference mark is reflected downstream through the first field defining member onto the surface in a manner such that the location of the reference mark on the surface is indicative of how the electron beam is aimed at the surface and such that the LED illumination illuminates the surface where the electron beam is aimed.

In another aspect, the present invention relates to an electron beam radiation system that emits an electron beam at a surface, comprising:

a) an electron beam unit having a unit outlet, wherein the electron beam unit produces the electron beam and emits the electron beam from the unit outlet on a linear pathway leading from the unit outlet to the surface, wherein the linear pathway has a central axis;

b) at least a first field defining member positioned on the linear pathway downstream from the unit outlet, wherein the first field defining member has a through aperture comprising an inlet through which the electron beam enters the first field defining member through aperture as the electron beam travels along the linear pathway to the surface, and an outlet through which the electron beam leaves the first field defining member through aperture as the electron beam travels along the linear pathway to the surface;

c) a rotary coupling system that rotatably couples at least the first field defining member to an upstream component of the electron beam unit such that the first field defining member is rotatable on demand around a rotation axis independent of rotation of the upstream component, wherein the rotary coupling system comprises:

i) a through aperture comprising an inlet through which the electron beam enters the rotary coupling system through aperture as the electron beam travels along the linear pathway to the surface, and an outlet through which the electron beam leaves the rotary coupling system through aperture as the electron beam travels along the linear pathway to the surface;

ii) a tilted mirror mounted at a tilted angle in the through aperture of the rotary coupling system, wherein the mirror is tilted at a non-parallel and non-orthogonal angle relative to the linear pathway, wherein the mirror is at least partially reflective with respect to optical illumination in one or more wavelength bands of the electromagnetic spectrum in a range from 200 nm to 2000 nm, and wherein the tilted mirror is at least partially transparent to the electron beam such that at least a portion of the electron beam passes through the tilted mirror as the electron beam travels along the linear pathway; and iii) a window through which light can be directed at the tilted mirror from a location outside the through aperture of the rotary coupling system; and d) a distance detection system positioned outside the through aperture of the rotary coupling system, wherein the distance detection system comprises a controller, a laser light source, and an image capturing sensor, wherein:

the laser light source is configured to emit a laser light signal at the tilted mirror in a manner effective to be reflected downstream along the linear pathway through the first field defining member toward the surface such that at least a portion of the laser light signal is reflected from the surface back to a location on the tilted mirror that is a function of a distance characteristic of the surface relative to a distance reference; and the image capturing sensor observes and captures image information of the tilted mirror, said image information indicative of the location on the tilted mirror onto which the laser light signal is reflected from the surface; and the control system uses the capture image information to determine a distance characteristic of the surface with respect to the distance reference.

In another aspect, the present invention relates to an electron beam radiation system that emits an electron beam, comprising:

a) an electron beam unit having a unit outlet, wherein the electron beam unit produces the electron beam and emits the electron beam from the unit outlet to the surface;

b) a sensor capable of sensing at least one of force and torque, wherein the sensor is coupled to the electron beam unit in a manner effective to detect at least one of force and/or torque readings associated with the electron beam unit; and c) a control system comprising at least one hardware processor operatively coupled to at least one memory, wherein the hardware processor is configured to execute steps comprising the following instructions stored in the at least one memory:

i) receiving the force and/or torque readings from the sensor;

ii) using information comprising the force and/or torque readings to determine profile information indicative of a rate of change of at least one of the force and/or torque readings as a function of time; and iii) using the profile information to determine a collision status of the electron beam unit.

In another aspect, the present invention relates to a method of detecting a collision status of an electron beam radiation unit that emits an electron beam, comprising the steps of:

a) a) providing an electron beam unit having a unit outlet, wherein the electron beam unit produces the electron beam and emits the electron beam from the unit outlet;

b) providing a sensor that measures at least one of torque and/or force, wherein the sensor is coupled to the electron beam radiation system in a manner effective to sense readings indicative of at least one of force and/or torque encountered by the electron beam radiation system;

c) using the sensor to sense force and/or torque readings associated with the electron beam unit;

d) using information comprising the sensed readings to determine profile information indicative of a rate of change of at least one of the torque and/or force readings as a function of time; and e) using the profile information to determine a collision status of the electron beam radiation system.

BRIEF DESCRIPTION OF THE DRAWINGS

FIG. 26 is a side cross-section perspective view of a portion of the applicator of FIG. 23 taken along line A-A, wherein the button is un-pressed and the shiftable plunger is in a locking position in which the shield is locked on the applicator.

FIG. 27 is a side cross-section perspective view of a portion of the applicator of FIG. 22 taken along line B-B showing the shiftable plunger in a locking position in the pocket behind the ramp in the wide slot.

FIG. 28 is a side cross-section perspective view of a portion of the applicator of FIG. 23 taken along line A-A, wherein the button is pressed causing the shiftable plunger to shift over in the wide slot to unlock the shield, allowing the shield to be removed from the applicator.

FIG. 36 is a bottom perspective view of the central core and mirror assembly used in the rotary coupling system of FIG. 29, also showing components of the optical illumination system in optical communication with the mirror.

FIG. 37 is a bottom perspective view of the central core and mirror assembly used in the rotary coupling system of FIG. 29, also showing components of the optical illumination system and the distance detection system in optical communication with the mirror.

FIG. 57 schematically illustrates a method of using the system of FIGS. 48 to 56 to automatically detect and respond to information indicative of the collision status of the system.

DETAILED DESCRIPTION

The embodiments of the present invention described herein are not intended to be exhaustive or to limit the invention to the precise forms disclosed in the specification and Figures. Rather a purpose of the illustrative embodiments chosen and described is so that the appreciation and understanding by others skilled in the art of the principles and practices of the present invention can be facilitated. While illustrative embodiments of the present invention have been shown and described herein, the skilled worker will appreciate that such embodiments are provided by way of example and illustration only. Numerous variations, changes, and substitutions will now occur to those skilled in the art without departing from the invention. No unnecessary limitations are to be understood therefrom. The invention is not limited to the exact details shown and described, and any variations are included that are within the scope of the claims.

All patents, patent applications, and publications cited herein are incorporated by reference in their respective entireties for all purposes.

Figure 1:
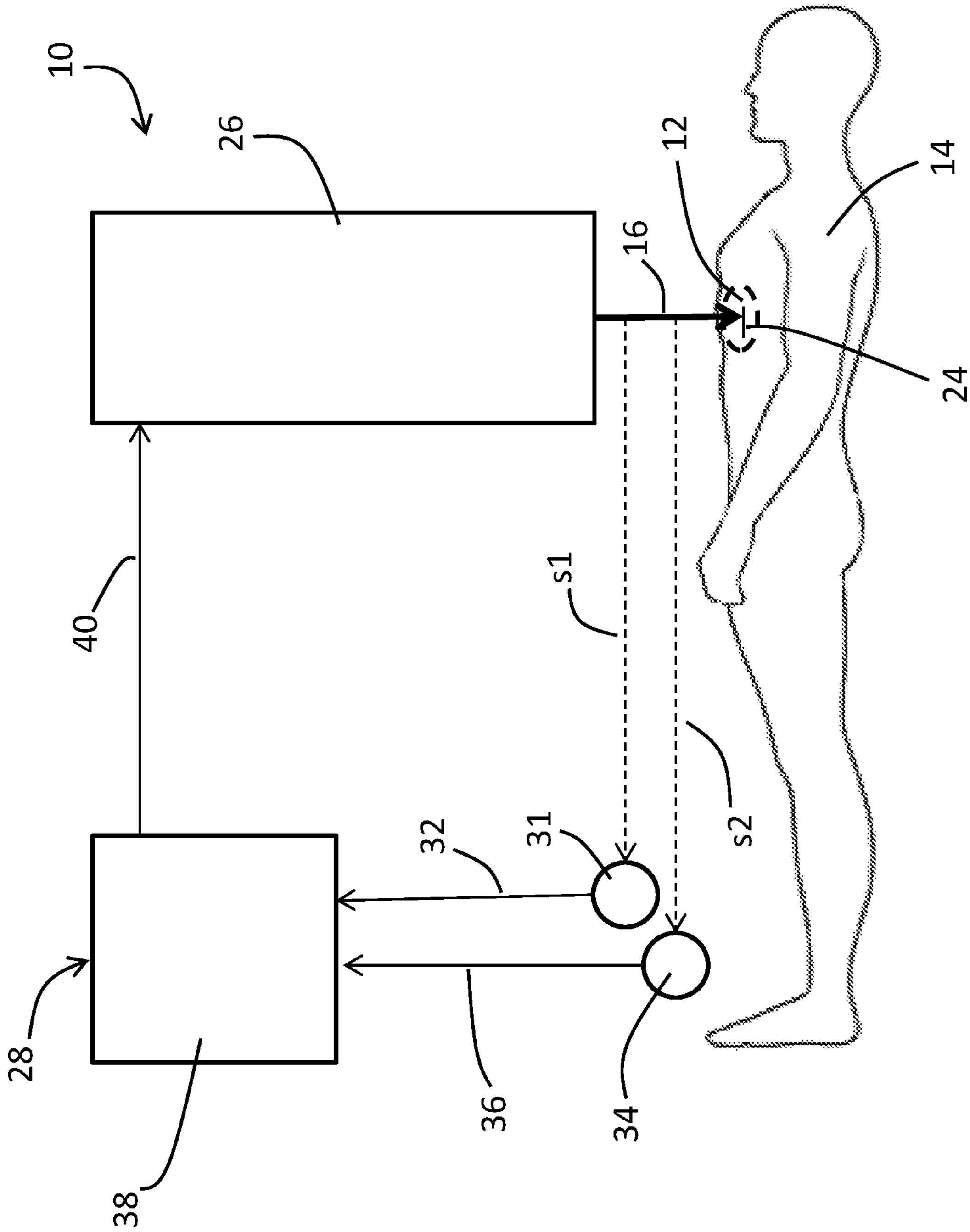
FIG. 1 schematically shows an illustrative embodiment of an electron beam radiation system of the present invention.

An exemplary embodiment of an electron beam (also referred to as an "ebeam") radiation system 10 of the present invention is schematically shown in FIG. 1. Electron beam radiation system 10 is useful to irradiate a target site 12 on a patient 14 with a desired electron beam radiation dose in one or more treatment fractions. Unit 26 is aimed so that electron beam 16 contacts and irradiates the target site 12 on patient 14 to deliver the desired dose using an appropriate electron beam energy, dose rate, and/or treatment time.

System 10 is useful for irradiating a wide range of treatment sites anywhere in or on body or body parts of the patient 14. For example, external treatments may involve treating the ears, nose, face, forehead, scalp, back, shoulders, neck, arms, hands, chest, abdomen, pelvic region, legs, or feet. Due to the ability to control the shape and aim direction of the electron beam aimed at the target site 12, system 10 is useful for treating target sites with a variety of shapes and contours.

Due to its compact nature, self-shielding capabilities, and/or mobility in many modes of practice, system 10 may be used to apply electron beam radiation before or after surgery. In some applications, such as scar amelioration, it is beneficial to irradiate the closed incision promptly. For example, system 10 can be used to deliver electron beam radiation dose(s) in a time period ranging from 0 to 24 hours, or even 0 to 5 hours, or even 0 to 1 hour, or even 0 to 30 minutes of the time of a surgery. This ability to apply irradiation treatments promptly is contrasted to treatments that use very large and immobile machines housed in separate, heavily-shielded environments that are remote from the treatment location. Radiation treatment in such large, remotely housed machines has been applied post-operatively after a delay of hours or days, thereby missing the opportunity to achieve the optimal benefits of electron beam radiation therapy.

System 10 is useful to carry out a wide range of treatments for which electron beam irradiation provides a treatment, benefit, or other desired effect for surgery or as an adjunct to surgery or other procedure. For example, system 10 may be used to treat dermatological conditions and/or to provide cosmesis. Exemplary applications in the dermatological field include prevention or treatment of scarring of the dermis including hypertrophic scarring, dermal fibroproliferative lesions, and benign fibrous tumors such as keloids. In some embodiments, electron beam radiation may be used to treat or prevent scar formation resulting from breast cancer surgical procedures or reduce the severity of scar formation in emergency room procedures. System 10 also may be used to selectively target and disable cancer tissue relative to surrounding healthy tissue.

Advantageously, system 10 also may be useful to carry out therapies referred to as "FLASH" treatments. The so-called FLASH treatments use atypically high electron beam dose rates for atypically brief time duration(s) in one or more fractions, often only a single fraction. FLASH treatments have shown the ability of high energy electron beam energy delivered for brief dose intervals to selectively target and disable cancer tissue with minimal harm if any to surrounding healthy tissue. In particular, researchers have discovered that delivering higher dose rates of 50 Gy/s and higher, even up to 1000 Gy/s, or even up to 2000 Gy/s, vastly reduces healthy tissue toxicity while preserving anti-tumor activity.

FLASH techniques used in electron beam therapy by system 10 may use electron beam energies such as an energy of 4 MeV or higher, even 6 MeV or higher, even 12 MeV or higher such as up to 20 MeV, or even up to 50 MeV, or even up to 100 MeV. Flash techniques may deliver a total electron beam dose in a single treatment or single fraction such as a dose of at least 5 Gy, or even at least 10 Gy, or even at least 15 Gy such as up to 100 Gy. Flash techniques may deliver an electron beam dose in a relatively brief interval such as a treatment in the range from 0.01 milliseconds to 500 milliseconds, or even 0.1 milliseconds to 100 milliseconds.

In contrast to FLASH radiotherapy, the operating ranges of about 12 MeV or less, or even 6 MeV or less, generally are associated with lower levels electron beam energy in the field of electron beam therapy. Such energies, particularly those of about 4 MeV or less, are potentially more useful for shallow treatments, e.g., those in which the penetration depth (discussed further below) of the electron beam is in the range from about a fraction of 1 mm to several cm. For example, in illustrative embodiments involving therapy with limited penetration depth, system 10 may implement irradiation to depths in the range from is 0.5 mm or less to about 4 cm, preferably 1 mm to about 3 cm, more preferably 1 mm to about 1 cm. In preferred modes of practice, the therapeutic penetration depth is limited to about 1.5 cm or less. Undue bremsstrahlung production can be avoided with careful attention to avoid unnecessary objects in the path of the electron beam. Certain objects are beneficially presented to the electron beam, such as scattering foils, windows, absorbers (described further below), sensors, ion chambers and the like.

Consequently, as compared to FLASH radiotherapy, other modes of practice may use lesser energy, dose rates, and or doses to be delivered in one or more fractions for suitable time periods. For example, for some therapies, the electron beam energy delivered to the target site 12 is within a range from 0.1 MeV to 12 MeV, preferably 0.2 MeV to 6 MeV, more preferably 0.3 MeV to 4 MeV, and even more preferably 0.5 MeV to 2 MeV. In some modes of practice, an operation range from 1 MeV to 2 MeV would be desirable. In such embodiments, the electron beam systems provide irradiation doses of up to about 20 Gy, such as up to about 15 Gy, up to about 10 Gy, up to about 5 Gy, or up to about 2 Gy. In such embodiments, the electron beam systems provide radiation to the target site 12 at a rate of at least about 0.2 Gy/min, at least about 1 Gy/min at least about 2 Gy/min, at least about 5 Gy/min, or at least about 10 Gy/min. In such embodiments, the electron beam energy may be delivered to the target site 12 for a time period in the range from 0.01 milliseconds to 5 minutes, or even 0.1 seconds to 3 minutes.

For purposes of illustration, FIG. 1 shows system 10 being used to irradiate incised tissue proximal to a surgical incision 24 after wound closure in order to help reduce or prevent undue formation of scar tissue that otherwise could result as the incision subsequently heals.

Electron beam radiation system 10 of FIG. 1 generally includes an electron beam generation unit 26 that emits a linearly accelerated, straight through electron beam 16. Using feedback control techniques as described in U.S. Pat. No. 10,485,993, system 10 emits electron beam 16 with high stability and precision to achieve one or more desired penetration depth settings within a broad operating range. The feedback principles described in U.S. Pat. No. 10,485,993 allow the beam penetration depth, beam energy, dose, and/or dose rate to be rapidly adjusted and controlled in continuous or very small increments within the corresponding operating ranges. Being able to adjust these characteristics continuously or in small increments provides tremendous flexibility to tailor dose, energy, dose rate, and/or penetration depth to particular patient needs. This is a significant advantage over conventional machines that have only a limited number of energy settings and/or provide beams with less stability that are subject to coarser setting adjustments.

Penetration depth of an electron beam treatment means the $R_{80}$ penetration depth as determined in water according to the protocol described in Peter R. Almond et. al, "AAPM's TG-51 protocol for clinical reference dosimetry of high-energy photon and electron beams," Med. Phys. 26 (9), September 1999, pp. 1847-1870 (referred to in the industry as the AAPM TG51 report). Note that while the protocol focuses on electron beams with mean incident energies in the range from 5 MeV to 50 MeV, the same protocol is applicable for lower or higher energies that optionally may be used in the practice of the present invention. Additionally, the report provides a protocol to determine the R50 penetration depth. This is the depth in water at which the absorbed dose falls to 50% of the maximum dose. The same depth-dose data resulting from this protocol also provides the $R_{80}$ penetration depth, which is the penetration of an electron beam dose into a water phantom at which the dose drops to 80% of the maximum dose. The depth of dose maximum is referred to as Dmax. Beam and dosimetry calibration for evaluation of machine settings with respect to determining $R_{80}$ penetration depth in the practice of the present invention are defined in water using a 5 cm diameter, circular, 30 cm long zero degree tip angle applicator at a 50 cm source to skin distance (SSD). The output for a specific energy is measured at Dmax.

For example, if this test shows that a particular machine configuration yields an $R_{80}$ penetration depth of 2 cm, that configuration is deemed to provide that $R_{80}$ penetration depth at the target site 12. The machine may be calibrated or otherwise evaluated to determine a plurality of machine configurations to correspond to a corresponding plurality of penetration depths. At the time of a procedure, the care provider selects a particular penetration depth suitable for the procedure. The machine is set to the corresponding configuration. The procedure is then performed using principles of the present invention to deliver a stable and precise electron beam as the procedure is carried out.

Electron beam energy and penetration depth are strongly correlated. See B. Grosswendt, "Determination of Electron Depth-Dose Curves for Water, ICRU Tissue, and PMMA and Their Application to Radiation Protection Dosimetry," Radiat Prot Dosimetry (1994) 54 (2): 85-97. Depending on the embodiment, this relationship can be linear or nonlinear. Generally, higher penetration depth results from using electron beams with higher energy.

Still referring to FIG. 1, system 10 includes feedback control system 28 configured to permit controlling and adjusting the penetration depth, electron beam energy, electron beam dose, and/or electron beam dose rate provided by electron beam 16 with precision and stability using feedback strategies such as those described in U.S. Pat. No. 10,485,993. As shown in FIG. 1, control system includes at least one monitoring sensor that is used to detect at least two different characteristics of the electron beam 16. Monitoring in this embodiment includes at least two sensors in the form of first sensor 31 and a separate second sensor 34. In other embodiments, more sensors may be included. Alternatively, multiple sensor capabilities may be incorporated into a single sensor component. First sensor 31 measures a first characteristic (s1) of the electron beam 16. First sensor 31 sends a corresponding first sensor signal 32 to controller 38. Signal 32 corresponds to the value of the characteristic s1 measured by first sensor 31. Second sensor 34 measures a second characteristic s2 of the electron beam 16. Second sensor 34 sends a corresponding second sensor signal 36 to controller 38

Controller 38 uses the sensed information in order to implement feedback control in one or more aspects of unit 26. For example using strategies described in U.S. Pat. No. 10,485,993, controller 38 may use the sensed information to derive an analog characteristic, A, of electron beam energy from the detected characteristics s1 and s2 presented by the signals 32 and 36. The result is that measuring at least two different characteristics of the beam and using those to derive the analog characteristic allows characteristics of the electron beam 16, such as energy, dose, dose rate, penetration depth, and/or the like, to be easily controlled by control system 28 with high precision.

Controller 38 can use the control signal 40 in different ways to implement such feedback control. As one example, control signal 40 can be used to shut off the electron beam pursuant to an interlock protocol. As another example, control signal 40 can be used to adjust power source(s) that generate the electron beam in order to tune electron beam energy as desired. In some embodiments, such power-based control can be implemented by feedback control of the microwave source 66 (See FIG. 2 or 3) and/or the electron source 70 (See FIG. 2 or 3). Using the feedback control strategies, modulator or magnetron-based feedback (e.g., feedback to regulate modulator output voltage or magnetron frequency) allows adjusting electron beam energy in steps or continuously over the desired operating range, e.g., 0.1 MeV to 12 MeV in some embodiments, or even 6 MeV up to 20 MeV, or even up to 50 MeV, or even up to 100 MeV in other illustrative embodiments.

Figure 2:
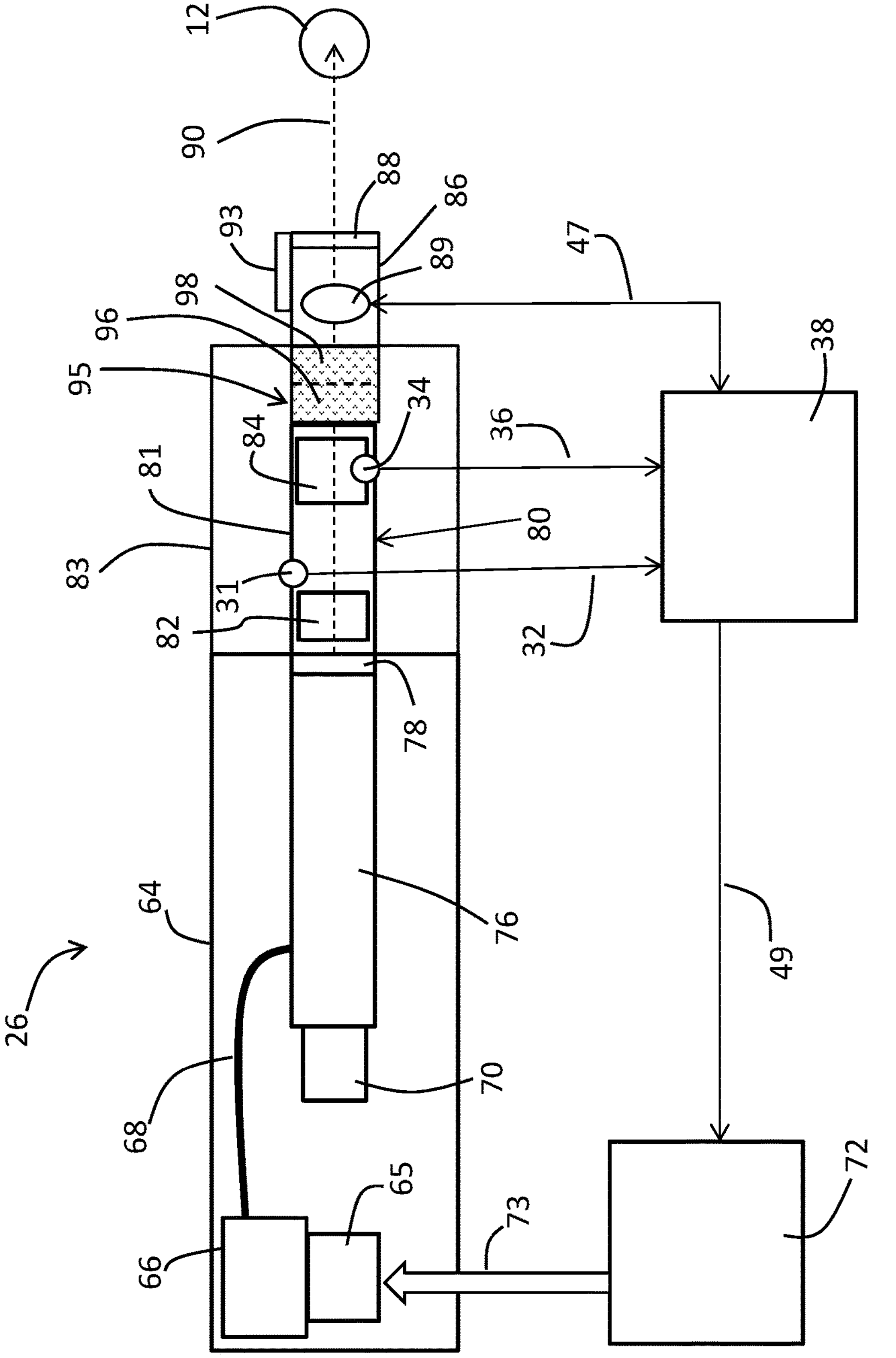
FIG. 2 schematically shows more details of an illustrative electron beam generation unit used in the electron beam radiation system of FIG. 1.
Figure 3:
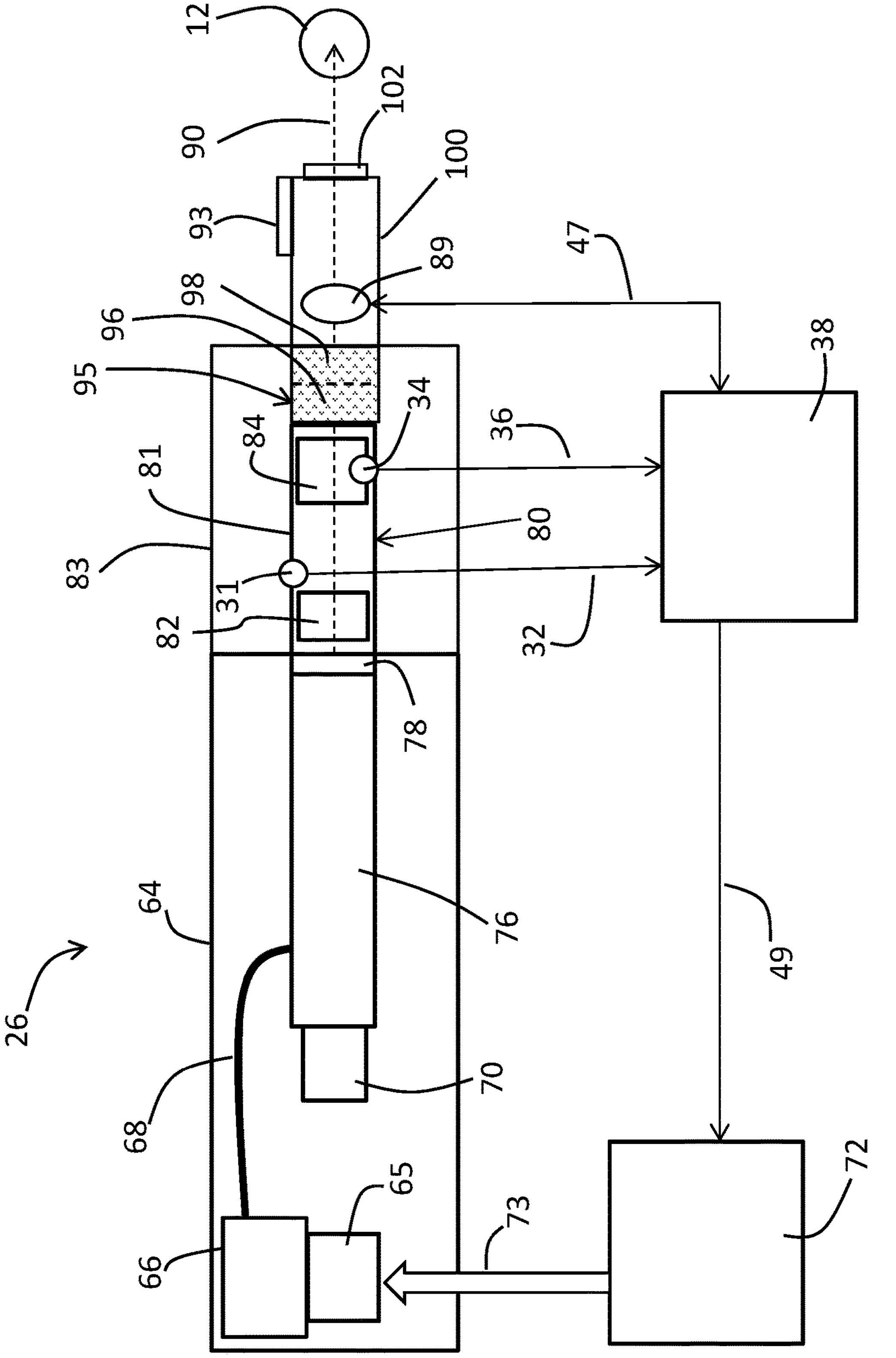
FIG. 3 schematically shows an alternative embodiment of an electron beam generation unit useful in the electron beam radiation system of FIG. 1.

As another example, the modulator output voltage can be regulated to affect current supplied to the magnetron and the microwave power. The magnetron power may be regulated, which impacts the amount of power delivered to the accelerator 86 (FIGS. 2 and 3). In addition to these strategies or as an alternative to these strategies, feedback control strategies may be used with respect to other system features that are used to establish the electron beam, including gun voltage or the like. The gun voltage can be regulated to impact the launch velocity of electrons, phasing, capture, and energy spectrum.

As another approach to implement feedback control, control signal 40 can be used to adjust the settings of one or more physical system components, e.g., one or more electron beam absorbers, whose selected position setting can be used to modulate the electron beam energy. One such adjustable component is an electron beam absorber of variable thickness that can be adjusted to present different thicknesses, and hence different absorptions, to the electron beam 16. Such absorber-based control may be accomplished with single absorbing plates providing a range of selectable thicknesses, a variable thickness ribbon, or a rotating body whose degree of rotation presents variable thickness absorption to the electron beam. Using the feedback control strategies of the present invention, absorber-based feedback allows adjusting electron beam energy in steps or continuously over the desired operating range.

When using any absorber(s) to help tune the electron beam 16, control system 28 desirably includes monitors (not shown) that confirm that an absorber is in the correct installed position. If the monitors provide a signal indicating that the position is incorrect, an interlock protocol is triggered that prevents the electron beam from being turned on. Similarly, in those embodiments in which system 10 includes a plurality of absorbers with different thicknesses, a particular absorber or combination of absorbers is the proper absorber selection for carrying out a particular treatment at a desired penetration depth. Accordingly, control system 28 desirably contains monitors that check if the installed absorber matches the machine settings for the particular treatment. If the improper absorber is installed for the selected procedure, an interlock protocol is triggered that prevents the beam from turning on. As a further safety function, a particular treatment will usually involve delivery of a particular radiation dose. Control system 28 desirably monitors the delivered dose in real-time and initiates an interlock protocol to turn off the electron beam to avoid overdose.

Some embodiments of the present invention combine both power-based and absorption-based feedback control of the electron beam energy, dose, dose rate, and/or hence penetration depth.

Exemplary features of one embodiment of a suitable electron beam generation unit 26 useful in system 10 are shown schematically in FIG. 2. Unit 26 according to FIG. 2 incorporates an advanced applicator coupling system 95 in accordance with the present invention.

Figure 46:
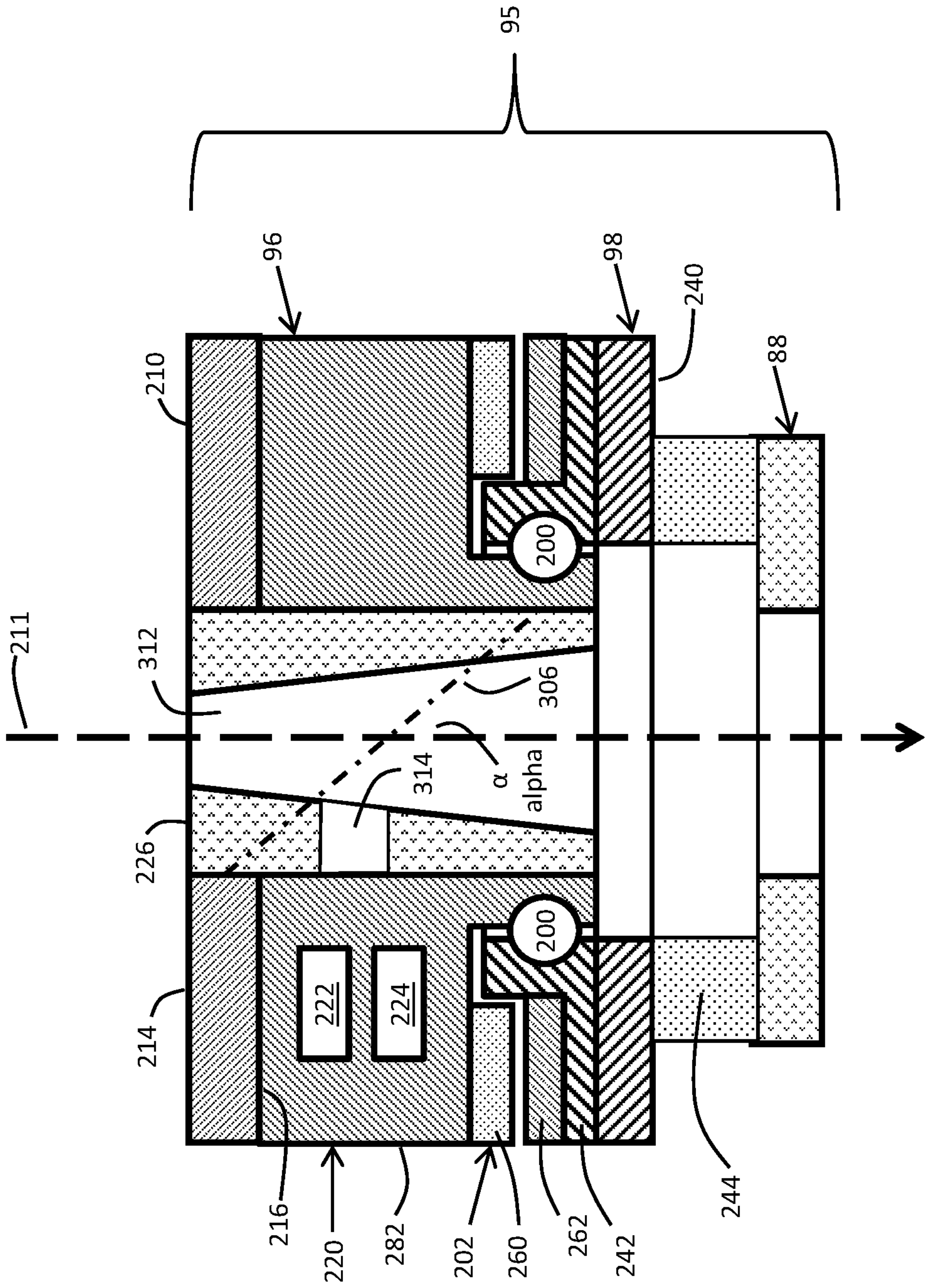
FIG. 46 schematically shows an exploded, side cross-section view of the rotary coupling system of FIG. 7 in which only the shield, and not the applicator, is used as a field defining member downstream from the rotary coupling system.
Figure 47:
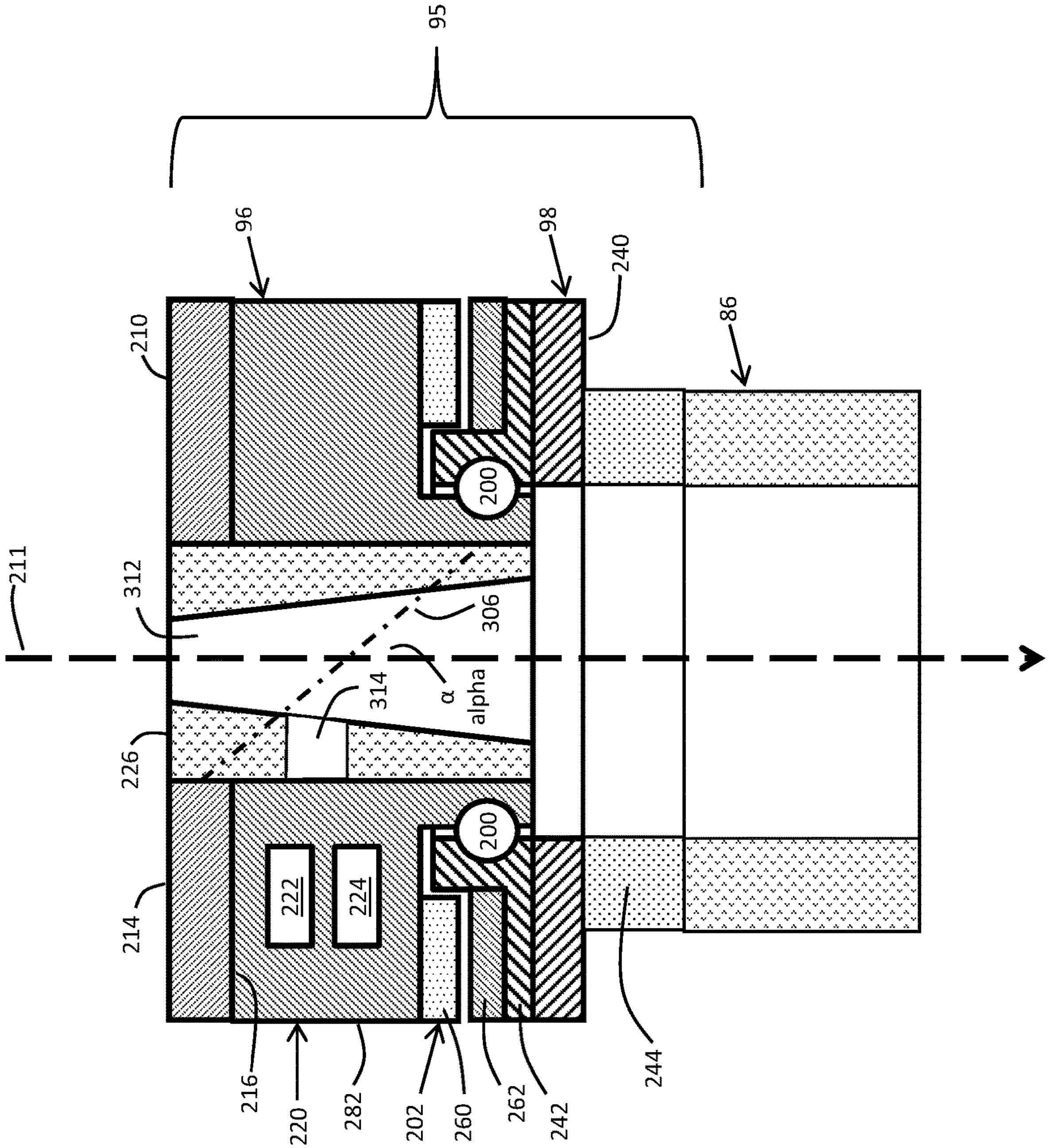
FIG. 47 schematically shows an exploded, side cross-section view of the rotary coupling system of FIG. 7 in which only the applicator, and not the shield, is used as a field defining member downstream from the rotary coupling system.

As seen in FIG. 2, electron beam generation unit 26 generally includes a first housing 64 that contains a modulator 65, microwave source 66, a microwave network 68, an electron source 70, and a linear accelerator 76. A second housing 83 contains a collimator 80. Using features of the present invention, the rotary coupling system 95 helps to rotatably mount on or more field defining members to be incorporated into unit 26. By way of example, system 10 is illustrated with a first field defining member in the form of an applicator 86 and a second field-defining member in the form of shield 88 integrated into the unit 26. Coupling system 95 generally incorporates a first sub-assembly 96 and a second sub-assembly 98, wherein the first sub-assembly 96 and second sub-assembly 98 are rotatably coupled to each other. The rotational coupling allows relative rotation between the two sub-assemblies 96 and 98 about an axis of rotation 211 (see, e.g., FIG. 5 and discussion below) that is parallel to, and desirably co-linear and coincident with, the central axis of the linear electron beam path 90. The coupling system 95 also incorporates automated distance detection, automated illumination functionality, and other functionality to be described further below. FIG. 46 below describes an embodiment in which shield 88 is attached to the rotary coupling system 95 to help shape the electron beam field, while the applicator 86 is not used. FIG. 47 below describes an embodiment in which applicator 86 is attached to the rotary coupling system 95 to help shape the electron beam field, while the shield 88 is not used.

An external power supply 72 supplies power to the modulator 65 via power cable 73. Power supply 72 and power cable 73 as an option may be included inside housing 64 along with other components. Controller 38 may be in communication with power supply 72 by communication pathway 49. An exit window 78 is provided at the interface between linear accelerator 76 and collimator 80. Scattering foil system 82 and ion chamber 84 are housed in collimator 80. Unit 26 generates an electron beam, which is aimed along substantially linear electron beam path 90 from accelerator 76 straight through applicator 86 to the target site 12 (also shown in FIG. 1). An optional field-defining shield 88 is placed at the exit of the applicator 86. A first sensor 31 is deployed with respect to collimator 80 for use in the feedback control strategies such as those described in U.S. Pat. No. 10,485,993. In such embodiments, ion chamber 84 among other functions also may serve as a second sensor 34 in such feedback control strategies.

Electron beam generation unit 26 as shown in FIG. 2 is the type that uses linear acceleration techniques to boost electron beam energy to desired levels. The use of linear accelerator structures to generate electron beams for therapeutic uses is well known. Additionally, electron beam generation unit 26 is a "straight through" type of system. As known in the art, a straight through system aims an electron beam at a target site along a generally linear path from the exit window 78 of the linear accelerator 76 straight through to the target site 12. This helps to ensure use of much of the beam current produced. Bending systems, in contrast, waste greater proportions of the beam current through absorption in bending magnet slits. Wastage of beam current in bending systems generally produces substantially greater background radiation per unit of dose delivered. A linear, straight-through beam line minimizes such beam loss and better optimizes dose per unit current to the target site. This means that the linear systems need less shielding. Straight through systems, therefore, tend to be smaller, more lightweight, and more compact than alternative systems that use heavy magnets and heavy shielding to aim electron beams on bent paths to a target site. An additional advantage of a straight through system is that energy may be varied quickly as there is no eddy current diffusion time limit or hysteresis as with bent beam systems. This makes linear, straight through systems more suitable for intraoperative procedures.

One example of such a system suitable for intraoperative procedures is described in U.S. Pat. No. 8,269,197 assigned to IntraOp Medical Corporation. Another example of such a system suitable for intraoperative procedures is the electron beam machine commercially available from IntraOp Medical Corporation under the trade designation MOBETRON. Generally, linear, straight through systems such as these are a result of engineering a compact linear accelerator that can fit when vertical under ceiling heights common to many procedure sites such as treatment rooms or surgery rooms. These compact systems avoid complex bending systems that tend to generate spurious background radiation that necessitates massive shielding.

Still referring to FIG. 2, modulator 65 receives power from the power output of power supply 72 via cable 73. Power supply 72 may be any suitable source of electricity. Power supply 72, as an option, may be a component of a continuous source of electricity from a power utility. Alternatively, power supply 72 may be battery powered, permitting untethered operation of electron beam generation unit 26. Modulator 65 accepts the power from power supply 72 (which may be line power, battery power or any suitable power source), and converts it to short pulses of high voltage that it applies to the microwave source 66. Microwave source 66 converts the voltage into microwave or RF energy.

Examples of suitable microwave sources for use as microwave source 66 include a magnetron or a klystron to power linear accelerator 76. A magnetron is more preferred as being less expensive and simpler to incorporate into system 10.

Many suitable embodiments of a magnetron operate using X-band, S-band, or C-band frequencies. X-band devices are more preferred, as other embodiments of unit 26 tend to be heavier when using S or C band devices. X-band frequency technology also tends to minimize the diameter, and hence the weight, of the accelerator structure. One illustrative example of a suitable magnetron operating at X-band frequencies is the Model L-6170-03 sold by L3 Electron Devices. This magnetron is capable of operating at a peak power of about 2.0 megawatts and 200 watts of average power.

Microwave network 68 conveys the microwave or RF power from the microwave source 66 to the linear accelerator 76. The microwave network 68 often typically includes a waveguide (not shown), circulator (not shown), a load (not shown), and an automatic frequency control system (not shown). The use of these components in an accelerator system is well known to those skilled in the art and has been described in the patent literature. See, e.g., U.S. Pat. No. 3,820,035. Briefly, microwaves from the RF source passes through the circulator before entering the accelerator guide to protect the RF source from reflected power from the accelerator 76. Instead, the power not absorbed in the accelerator 76 is reflected back into the circulator and shunted into a water-cooled or air-cooled dummy load. In the preferred embodiment, air-cooling is preferred as air cooling reduces weight and minimizes servicing issues. An AFC circuit is used to keep the resonant circuit tuned to the microwave frequency. Air cooling works in the practice of the present invention because magnetron average power, e.g., 200W in an illustrative embodiment, is relatively low for electron beams. In contrast, x-ray machines typically involve average power in the range from 1 kW to 3 KW. The ability to use air cooling with electron beams is one factor that helps preferred electron beam machines of the present invention to be so compact and lightweight.

Microwave or RF power may be injected into the accelerator 76 through a fixed waveguide if the microwave source 66 (e.g., a magnetron) is mounted on a rigid assembly (not shown) with the linear accelerator 76. Alternatively, a flexible waveguide may be used in the microwave network 68. As one option for implementing the feedback principles of the present invention, microwave or RF power supplied to the linear accelerator 76 through microwave network 68 may be modulated in the case of a magnetron by varying the pulsed high voltage supplied to the magnetron from power supply 72. Modulating the voltage of the power supply 72 in this manner allows the energy level, dose, dose rate, and/or penetration depth of the electron beam 16 to be controlled and adjusted to many different desired settings with excellent precision using the feedback strategies of the present invention. For a klystron, the same approach may be used. Alternatively, the input microwave power to the klystron may be varied.

In parallel with microwave source 66 supplying microwave or RF energy to linear accelerator 76, electron source 70 supplies electrons to linear accelerator 76. Electron source 70 typically includes an electron gun and features that couple the gun to the linear accelerator 76. Many different embodiments of electron guns are known and would be suitable. For example, some embodiments use a diode-type or triode-type electron gun, with a high-voltage applied between cathode and anode. Many commercially available electron guns operate at voltage ranges between 10 kV to 17 kV, though electron guns operating at other voltages may, in some embodiments, also be used. The voltage often is either DC or pulsed. In the case of the triode-type gun, a lower grid voltage also is applied between the cathode and grid. The grid can disable or enable the beam, and the grid voltage may be varied continuously to inject more or less gun current. The grid voltage may optionally be controlled through a feedback system. A skilled worker in the field of linear accelerator engineering is able to understand and choose an appropriate gun design suitable for the linear accelerator 76 to be used.

One example of a commercially available electron gun suitable in the practice of the present invention has been sold by L3 Electron Devices (formerly Litton) under the product designation M592 Electron Gun. The injector cathode of this particular gun operates in some embodiments at 10 kV to 14 kV and has a very small diameter emitting surface. This design is intended to provide low emittance and good capture efficiency while maintaining low energy spread. Typical pulse widths for operation may be in the range from 0.5 to 6 microseconds.

The RF source is pulsed by a modulator 65. It is preferred that the modulator 65 be solid state based rather than tube based to reduce weight and improve portability. The pulse repetition frequency (PRF) may be selected from a wide range such as from about 1 to about 500 pulses per second, and the pulse width may be selected from a wide range such as from about 1 to 25 microseconds. Some treatments can occur at these frequency rates and pulse widths for a particular time duration, e.g., from 0.5 seconds to 3 or even more minutes in some treatments. Other treatments may proceed for a given number of pulses and optionally fractional pulses such as from 1 to 50 pulses. The combination of PRF and pulse width is one factor that impacts the dose rate of the emerging electron beam. For diode-gun systems, the gun likewise may be pulsed by the same modulator system, albeit with an intervening gun transformer to permit a step in voltage.

Linear accelerator 76 is configured to receive the microwave or RF power from the microwave network 68. Linear accelerator 76 also is configured to receive the electrons from the electron source 70. Linear accelerator 76 is coupled to the microwave network 68 and the electron source 70 in a manner effective to use the microwave or RF power to accelerate the electrons to provide electron beam 16 having an energy in the desired operating range.

A variety of different linear accelerator structures would be suitable in the practice of the present invention. For example, linear accelerator 76 may have a structure that implements any of a variety of different cavity coupling strategies. Examples of suitable structures include those that provide side cavity coupling, slot coupling, and center hole coupling. C. J. Karzmark, Craig S. Nunan and Eiji Tanabe, Medical Electron Accelerators (McGraw-Hill, New York, 1993). Linear accelerator 76 also may have a structure that implements a variety of different symmetry strategies. Examples of suitable structures include those that provide periodic, bi-periodic, or tri-periodic symmetry. Examples of suitable accelerator structures also may implement a range of standing wave or travelling wave strategies. Examples of suitable linear accelerators 76 also may be selected to operate with many different bands of microwave or RF power. Examples of suitable power bands include S-Band (2-4 GHZ), C-Band (4-8 GHZ), X-Band (8-12 GHz), and still higher frequencies. David H. Whittum, "Microwave Electron Linacs for Oncology," Reviews of Accelerator Science and Technology, Vol. 2 (2009) 63-92. In some illustrative embodiments, the linear accelerator 76 uses a low profile structure design, incorporating on-axis bi-periodic cavities operated at X-band frequencies. U.S. Pat. No. 8,111,025 provides more details on charged particle accelerators, radiation sources, systems, and methods. Side-coupled X-band accelerators and on-axis and side-coupled S-band and C-band accelerators are other suitable examples.

The linear accelerator 76, its attached electron source 70, and one or more other components of electron beam generation unit 26 may be mounted inside housing 64 on a strongback (not shown) or other suitable support member. The linear accelerator 76 and electron source 70 may be encased in lead or other shielding material (not shown) as desired to minimize radiation leakage. The higher the resonant frequency of the accelerator guide, the smaller is the diameter of the structure. This results in a lighter-weight encasement to limit leakage radiation. An advantage of linear, straight through machines is that the shielding requirements are less severe than machines that using beam bending strategies. This allows straight-through electron beam radiation machines to be deployed for intraoperative procedures rather than being deployed in remote locations inside heavily shielded rooms.

During operation, the network 68, the linear accelerator 76 and the microwave source 66 experience heating. It is desirable to cool unit 26 (particularly the units 65, 66, the circulator and loads in 68, and 76) in order to dissipate this heat. A variety of strategies can be used to accomplish cooling. For example, accelerator 76 and microwave source 66 can be water-cooled as is well known. In addition, the practice of the present invention permits operation at low-duty cycle, for which air-cooling would be quite adequate. The ability to practice air cooling simplifies the construction of unit 26 and helps to make the unit 26 smaller and more compact. The result is that the corresponding system 10 (See FIG. 1) is easier to deploy and use in intraoperative procedures.

An exit window 78 at the beam outlet of linear accelerator 76 is to help maintain a vacuum within the accelerator. The window 78 should be strong enough to withstand the pressure difference between the accelerator vacuum and the ambient atmospheric pressure, e.g., a difference of about 15 psi in some instances, but should be thin enough to avoid excessive beam interception and/or bremsstrahlung production. Balancing these factors, the window 78 may be formed of titanium in many embodiments. Alternatively, beryllium or other metallic or composite materials also may be used.

The accelerated electron beam 16 exits the linear accelerator 76 through exit window 78 and next continues on a linear path through collimator assembly 80 that receives, broadens, and flattens the beam. To implement feedback strategies of the present invention, one or more sensors may be deployed in or around collimator 80 in order to detect two or more independent characteristics of the beam. In the illustrative embodiment of FIG. 2, sensor 31 functions as a first sensor, and ion chamber 84, among its other functions, functions as a second sensor 34. Sensor 31 schematically is shown to the side of collimator 80, and thus generally out of the beam path in this embodiment. Other deployments, including deployments in the beam path or other locations downstream from exit window 78 may be used, if desired. For example, toroid devices are generally annular in shape and can be deployed so that the beam is transmitted through the open central region of the toroid.

Collimator 80 can include a housing 81. Housing 81 may be constructed of materials that help contain bremsstrahlung radiation, or the collimator design itself could be sufficient to contain the bremsstrahlung radiation. Inside housing 81, scattering foil system 82 and ion chamber 84 are provided. Scattering foil system 82 serves multiple functions. For example, electron beam systems typically produce beams of small transverse dimension, on the order of 1 mm to 3 mm across, much smaller than typical treatment fields. Scattering foil system 82 helps to broaden the electron beam 16. The scattering foil system 82 also helps to flatten electron beam 16. In many modes of practice, the beam passes through the scattering foil system 82 to help in shaping of the isodose curves at the treatment plane at target site 12.

In illustrative modes of practice, scattering foil system 82 helps to enlarge the accelerated beam 16 from being several square millimeters in cross section to several square centimeters in cross section. Uniformity of dose across the treatment field is a desired goal to simplify dose planning for therapeutic applications. For example, collimator 80 with or without applicator 86 may function to provide a flat electron beam dose profile such that the coefficient of variation of the beam dose across the full width at half-maximum (FWHM) of the beam is less than ±50%, less than ±40%, less that ±30%, less than ±20%, less than ±10%, less than ±5%, less than ±2.5%, or less than ±1%. Those of skill in the art will recognize that the coefficient of variation of the electron beam energy across the FWHM may have any value within this range, for example, about ±5%. In some embodiments, the collimator may function to broaden the electron beam to field sizes that are 1 cm to 25 cm across.

A typical scattering foil system 82 includes at least one, even two or more, and even three or more scattering foils (not shown). The distance between the two or more foils can vary, depending on the energy range of the unit, the field size needed for the treatment application, and the geometry and materials of the mass elements in the treatment head. Generally, electron scattering foils may be designed using techniques such as empirical design iteration or Monte Carlo simulations. Other means of providing uniformity could rely on magnetic phenomena. For example, steering coils could be employed to raster the beam across a programmed area. Alternatively, a quadrupole magnet system could be used to modify the beam size at the target plane.

Ion chamber 84 serves multiple functions. In one aspect, ion chamber 84 monitors the radiation dose delivered by the system and radiation when the prescribed pre-set dose is delivered. The monitor features of ion chamber 84 may be segmented transversely to provide a reading of beam position in the transverse plane. This reading may be used in a conventional feedback control system to provide current to steering coils upstream, so as to steer the beam and continuously correct any beam offset or symmetry error. Advantageously, in the practice of the present invention, this reading may be used in an innovative feedback control system (described further below) used to control the electron beam energy, and hence penetration depth at the target site, with excellent precision. As another function, ion chamber 84 may be used to terminate the beam and limit the amount of radiation received at the target site if an issue with the electron beam is detected. For example, a loss of a scattering foil could result in delivery of an excessive dose. In this fashion, ion chamber 84 and associated electronics provide protective interlocks to shut down the beam under such circumstances.

The first sub-assembly 96 of coupling system 95 is attached to the exit end of collimator 80. In the meantime, applicator 86 is attached to the exit end of the second sub-assembly 98. Field defining shield 88 (also referred to as an "insert") is attached to the exit end of the applicator 86. Because second sub-assembly 98 is rotatably coupled to the first sub-assembly 96, this means that applicator 86 and the attached shield 88 are able to rotate about axis 211 relative to the first sub-assembly 96 and, hence, collimator 80 and other upstream components of unit 26. Rotation is helpful to help ensure that an appropriate alignment for the field defining opening (e.g., the outlet of the shield 88) with the treatment site, e.g., tumor, scar, incision, etc., is achieved.

If the applicator is metallic and could come into contact with the target site 12, the applicator 86 desirably is electrically isolated from the upstream components (e.g., coupling system 95, collimator 80, etc.) of system 10. This can be accomplished in various ways such as by interposing an insulative coupling between applicator 86 and second sub-assembly 98 or between applicator 86 and patient 14, or by forming applicator from a material that is inherently insulating (e.g., polymethyl(meth)acrylate often referred to as PMMA, quartz, ceramic, or the like).

The accelerated and collimated electron beam is aimed at a target site 12 through applicator 86 and field defining shield 88. The applicator 86 and shield 88 are configured so that the electron beam continues on linear electron beam path 90 straight through to the target site 12. In many modes of practice, the applicator 86 and shield 88 further help to define the shape and flatness of the electron beam 16. Applicator 86 also makes it easier to aim the electron beam while minimizing the manipulation of, contact with, or disturbance of the patient 14 or target site 12. Furthermore, the use of applicator 86 and shield 88 helps to avoid stray radiation and minimizes the dose delivered to healthy tissue by confining the radiation field.

Applicator 86 and/or shield 88 optionally may include one or more other components to help further modify the electron beam characteristics. For example, energy reduction with low bremsstrahlung can be achieved by interspersing thin (0.5-1 mm) sheets of plastic or sheets made from low atomic number material into the applicator 86 and/or shield 88 in a slot provided to accept them. Materials with higher electron density also may be used and could be thinner for the same absorption. The applicator 86 and/or shield 88 could also incorporate element(s) to act as a secondary scattering component. These may be made from suitable shaped low atomic number materials that help to further scatter electrons within the volume of applicator 86 and/or shield 88. Examples of such materials, but by no means exclusive to these materials, include aluminum, carbon, and copper and combinations of these. These can be located in applicator 86 at positions determined by Monte Carlo calculations or empirically for the energy and field size needed for the application.

In some modes of practice, a transparent or partially transparent applicator 86 and/or shield 88 may be beneficial. For example, such an applicator design may allow easier viewing of the treatment site. Applicators and or shields fabricated at least in part from PMMA, quartz, or the like would permit such viewing.

Unit 26 may be positioned in any orientation or position with respect to the target site 12 regardless of patient orientation. In many modes of practice, the distance from the exit end of the applicator 86 (or the end of field defining shield 88, if present) to the surface of the target site 12 can vary from contact with the target site 12 to distances up to about 10 cm from the patient surface. The distance can be determined by any suitable measurement technique such as by either mechanical measurement or an electronic rangefinder. Advantageously, coupling system 95 includes functionality that allows distance to be determined automatically. In some embodiments, the system 10 and/or applicator 86 may be positioned manually to achieve any orientation or position relative to the target site 12. In some embodiments, system 10 and/or the applicator 86 may be positioned using one or more motor drives for automated control of orientation and position. For example, the applicator 86 could be placed by hand and held in place by a suitable support structure (not shown). Then the electron beam machine would be docked (i.e., aligned) to the applicator 86. The applicator 86 desirably is electrically isolated from other components of system 10, particularly in treatments in which the applicator contacts or is close to the patient 14.

The applicator 86 may have a variety of shapes, such as being shaped to produce circular, square, irregular, or rectangular fields on the target site. Some useful applicators include cylindrical pathways for the electron beam to traverse. Another example of an applicator design, called a scan horn, creates long narrow fields by having scattering elements within the applicator that scatter electrons preferentially along the length of the field. In some embodiments, the scan horn may be used to confine the irradiated area to a strip of from about 2 cm to about 10 cm in length, and about 0.2 cm to about 1 cm in width.

FIG. 2 shows how an absorber 89 may be mounted on applicator 86 in a manner effective to tune the electron beam to adjust electron beam energy, dose, dose rate, penetration depth, or the like. By having a library of absorbers 89 with fine, stepwise differences in electron beam absorption, different adjustments of the electron beam in fine increments can be delivered to treatment sites such as site 12. In the meantime, feedback strategies such as those described in U.S. Pat. No. 10,485,993 are used to stabilize the electron beam with high precision prior to tuning by the absorber 89. To change to another penetration depth setting, one or more different absorbers 89 are presented to the beam and/or the machine may be set to produce an electron beam with a different energy level that is presented to the one or more absorbers 89. The different absorbers 89 may be installed manually or via automation. U.S. Pat. No. 10,485,993 further describes how to use absorbers to help adjust an electron beam.

FIG. 2 shows absorber 89 mounted to applicator 86. The absorber 89 may be located in other positions and still provide effective tuning. Generally, the absorber 89 is deployed in the path 90 of the electron beam between the exit window 78 and the target site 12. Many suitable embodiments of absorber 89 are fabricated from one or more low Z materials above atomic number 4. Exemplary materials useful to form absorber 89 include carbon, aluminum, beryllium, and combinations of two or more of these. Higher Z materials could be used, but with the risk of generating undo amounts of Bremsstrahlung radiation. Controller 38 may be in communication with absorber(s) 89 via communication pathway 47.

FIG. 2 shows machine vision capability integrated with unit 26. In some embodiments, machine vision is achieved by mounting one or more endoscopes 93 onto applicator 86. Endoscope 93 allows real time video imaging of target site 12. Endoscope 93 or other machine vision capability is helpful to allow target site 12 to be viewed without obstruction by applicator 86, shield 88, or other components of system 10. As one advantage, endoscope 93 allows real time viewing of target site 12 as system 10 is set up and aimed at the target site 12. This can be helpful to make sure that system 10 is aimed properly at site 12 without undue misalignment or tilting. An operator can also view the captured image information to observe the site 12 during a treatment. This will allow the operator to capture image information to document the treatment. Also, the operator can observe to make sure that the patient 14 does not move out of the proper set up as a treatment proceeds. Endoscope 93 is very suitable for this, as endoscopes generally are flexible for easy mounting, capture high quality, real time images, and are inexpensive.

FIG. 3 shows an alternative configuration of unit 26 FIG. 2. Unit 26 of FIG. 3 is identical to unit 26 as shown in FIG. 2 except that a different applicator 100 and an alternative field defining shield 102 are used. In this illustration, applicator 100 is longer than applicator 86 (FIG. 2), while shield 102 is smaller and helps shape a more tightly defined electron beam field than shield 88 (FIG. 2). FIG. 3 shows the modular capabilities of unit 26 with respect to independently choose and use different applicators and/or shields to easily adapt to the needs of a variety of different electron beam treatments and circumstances. The applicators are modular in the sense that a library may include an inventory of two or more applicators, each of which is interchangeably mounted on the unit 26. Similarly, the shields are modular in the sense that a library may include an inventory of two or more shields, each of which is interchangeably mounted on the unit 26.

Figure 4:
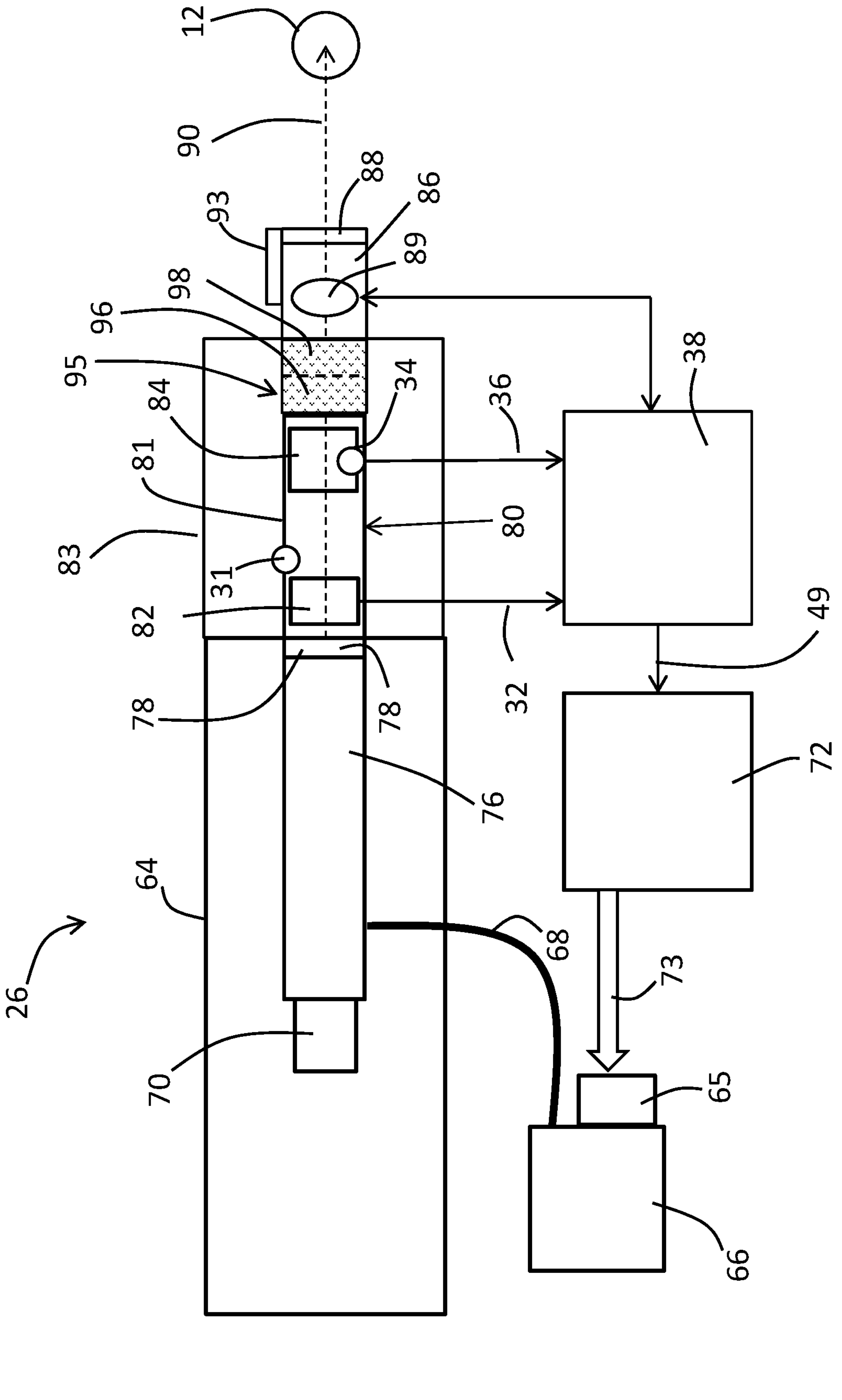
FIG. 4 schematically shows an alternative embodiment of an electron beam generation unit useful in the electron beam radiation system of FIG. 1.

FIG. 4 shows another alternative embodiment of the electron beam generation unit 26. The unit 26 of FIG. 4 is identical to the system 10 of FIG. 2 except that the microwave source 66 and a portion of the microwave network 68 are external to housing 64. Rotational motion between the two ends of the network 68 can be practiced by incorporating one or more rotary joints into network 68 according to conventional practices.

Figure 12:
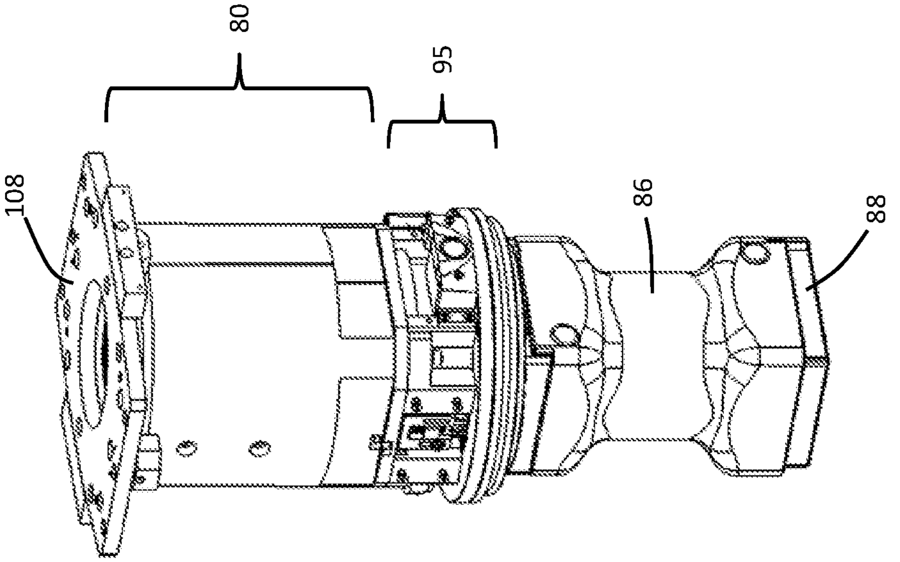
FIG. 12 shows a perspective view of the assembled components of FIG. 11 with a housing removed to uncover the underlying collimator and rotary coupling system.

FIGS. 5 to 45 show the applicator 86, shield 88 and coupling system 95 of FIGS. 1 and 2 in more detail. Referring first to FIGS. 11 and 12, FIGS. 11 and 12 show how easily housing 83 is mounted and de-mounted from unit 26. FIG. 11 shows how housing 83 is mounted over the collimator 80 (not shown in FIG. 11 as being under housing 83) and the coupling system 95 (not shown in FIG. 11 as being under housing 83) using screws 105 to help hold housing 83 in place. The applicator 86 and shield 88 are accessible below the housing 83. To remove housing 83, the screws 105 are removed. Similar screws are on the other side of housing 83 as well. Removing the screws 105 releases the housing 83. This allows the housing to be removed from unit 26 in the direction shown by downward arrow 106. Note that button 438 is used for the separate function of releasing rotational locking functionality so that the applicator 86 can be rotated. FIG. 12 shows the uncovered unit 26 after housing 83 is removed. The collimator 80 and coupling system 95 are now exposed. A mounting plate 108 also is shown at the top of the collimator 80. Mounting plate 108 is used to attach collimator 80 to upstream components of unit 26.

Figure 14:
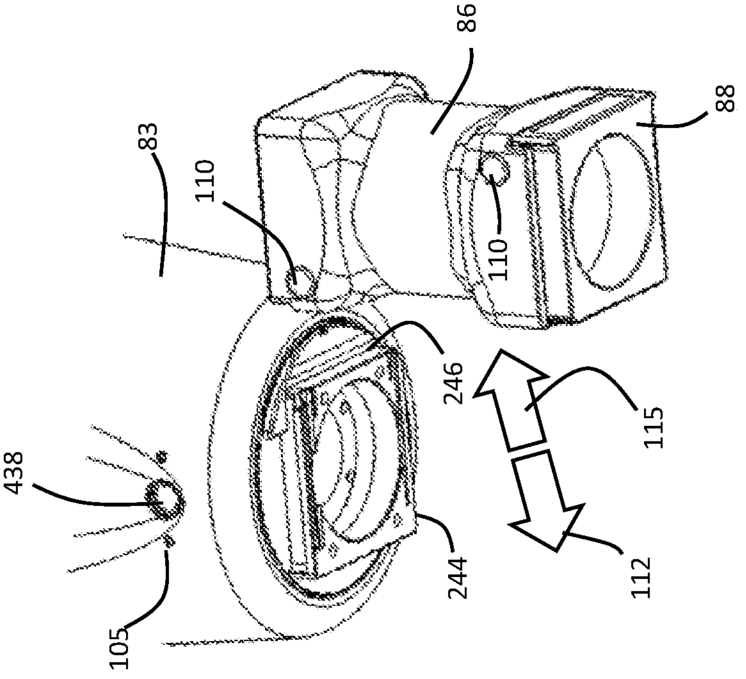
FIG. 14 is a bottom, perspective view of the components shown in FIG. 13.
Figure 13:
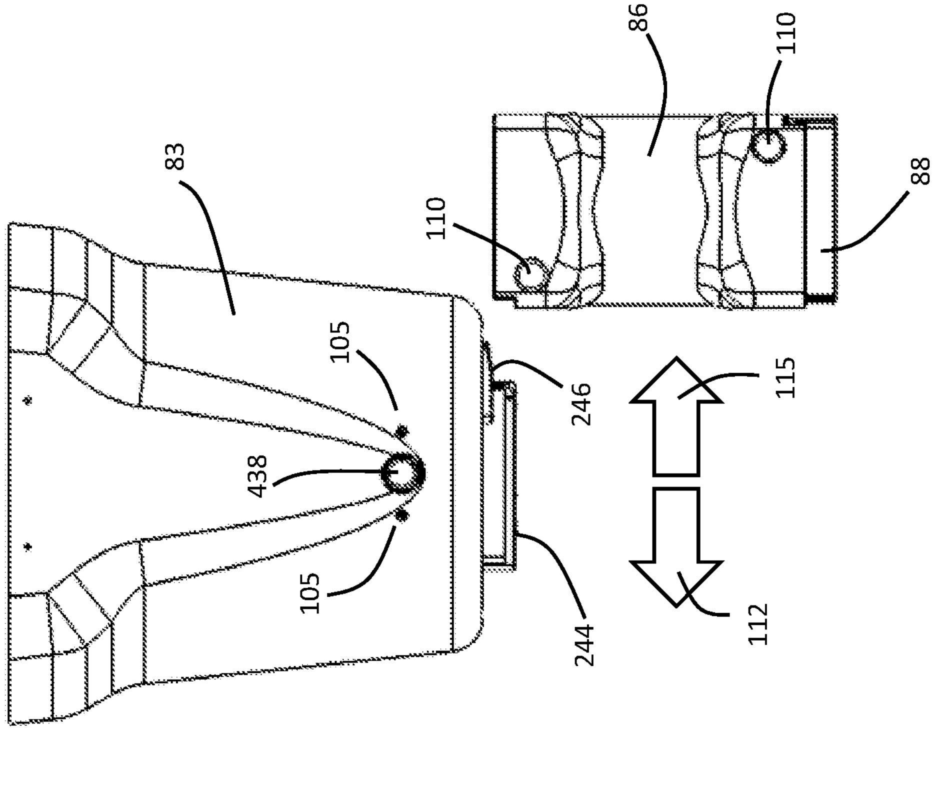
FIG. 13 is a further side view of the components of FIG. 8 showing how the applicator and shield (attached to the outlet of the applicator) are mounted and demounted from the rotary coupling system.
Figure 16:
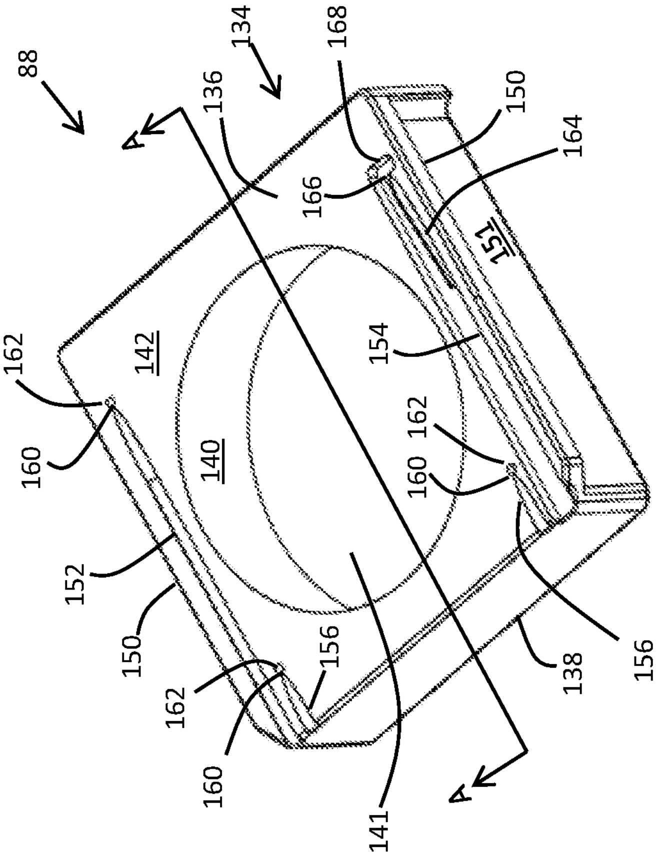
FIG. 16 is a top perspective view of the shield of FIG. 11.
Figure 15:
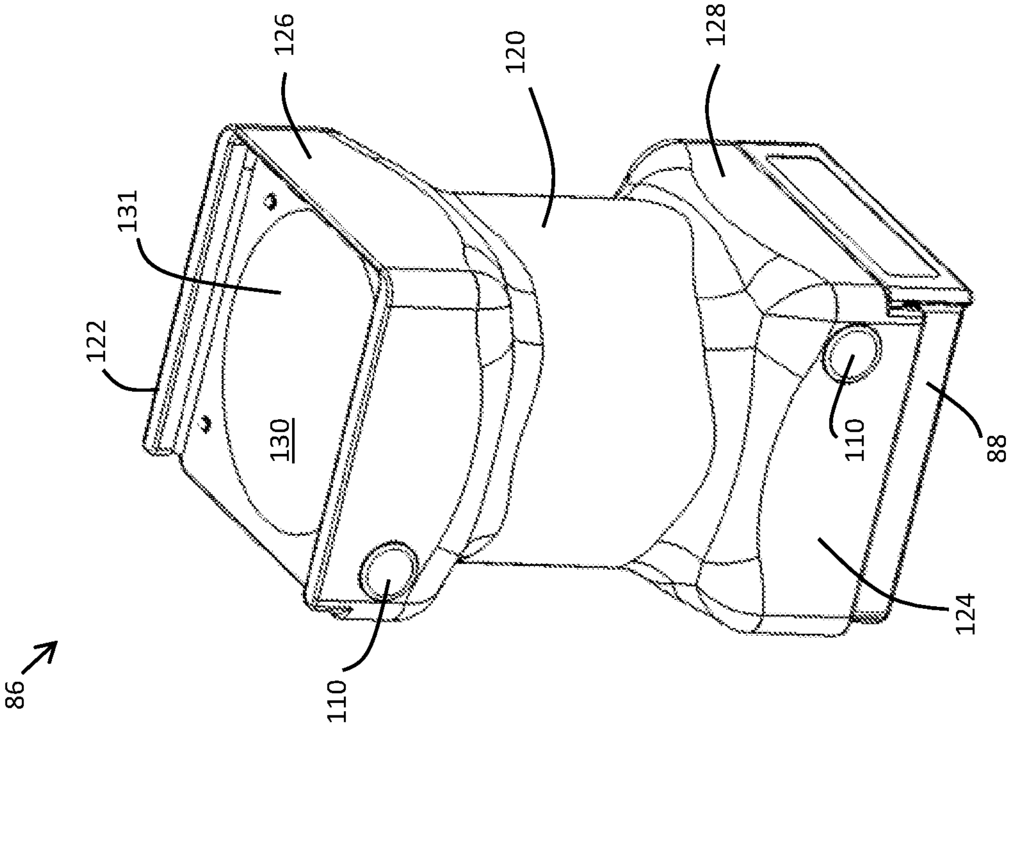
FIG. 15 is a top perspective view of the applicator used of FIG. 11.
Figure 18:
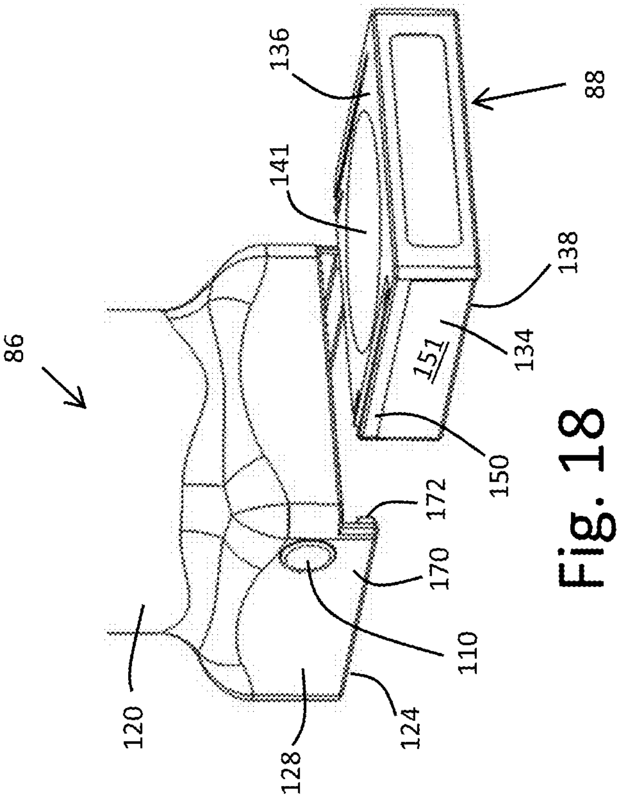
FIG. 18 is another side perspective view showing the shield and a lower portion of the applicator of FIG. 17.
Figure 17:
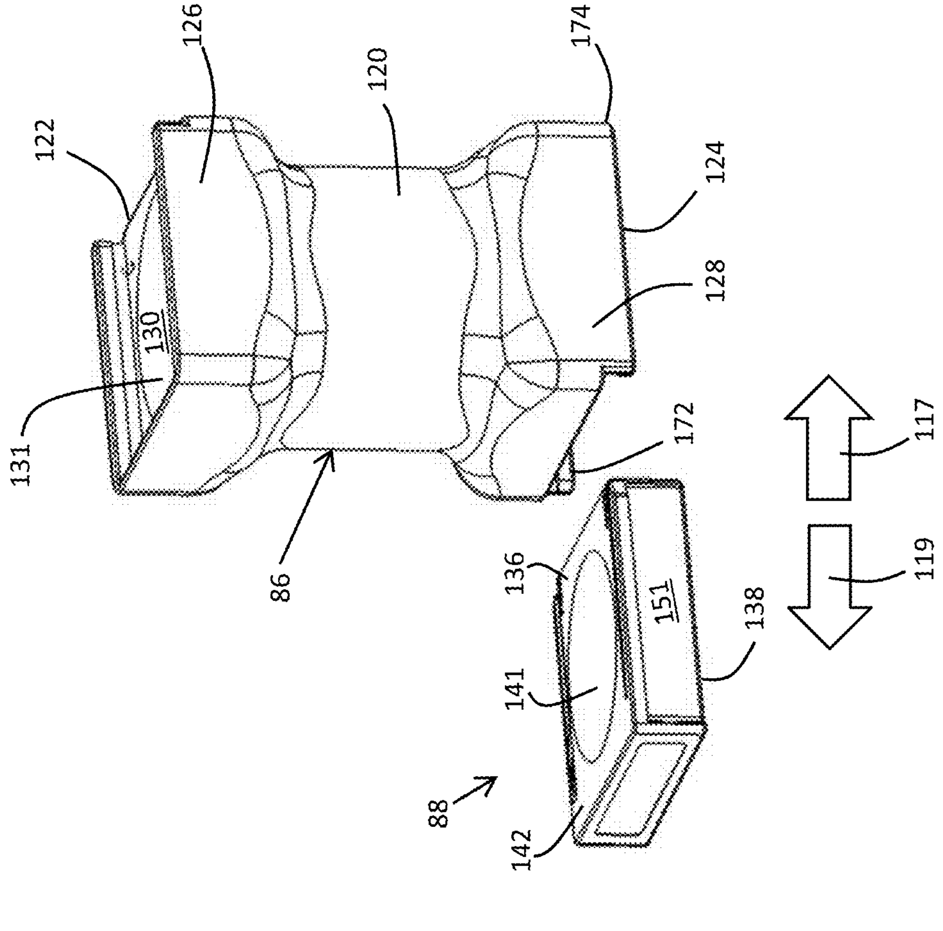
FIG. 17 is a side perspective view showing how the applicator and shield of FIG. 11 are mounted to and demounted from each other.
Figure 20:
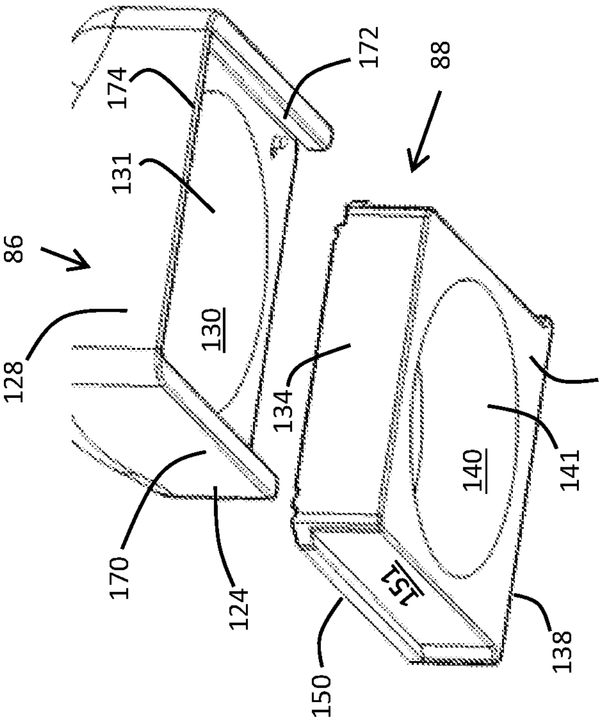
FIG. 20 is a bottom perspective view showing the shield and a lower portion of the applicator of FIG. 19.
Figure 19:
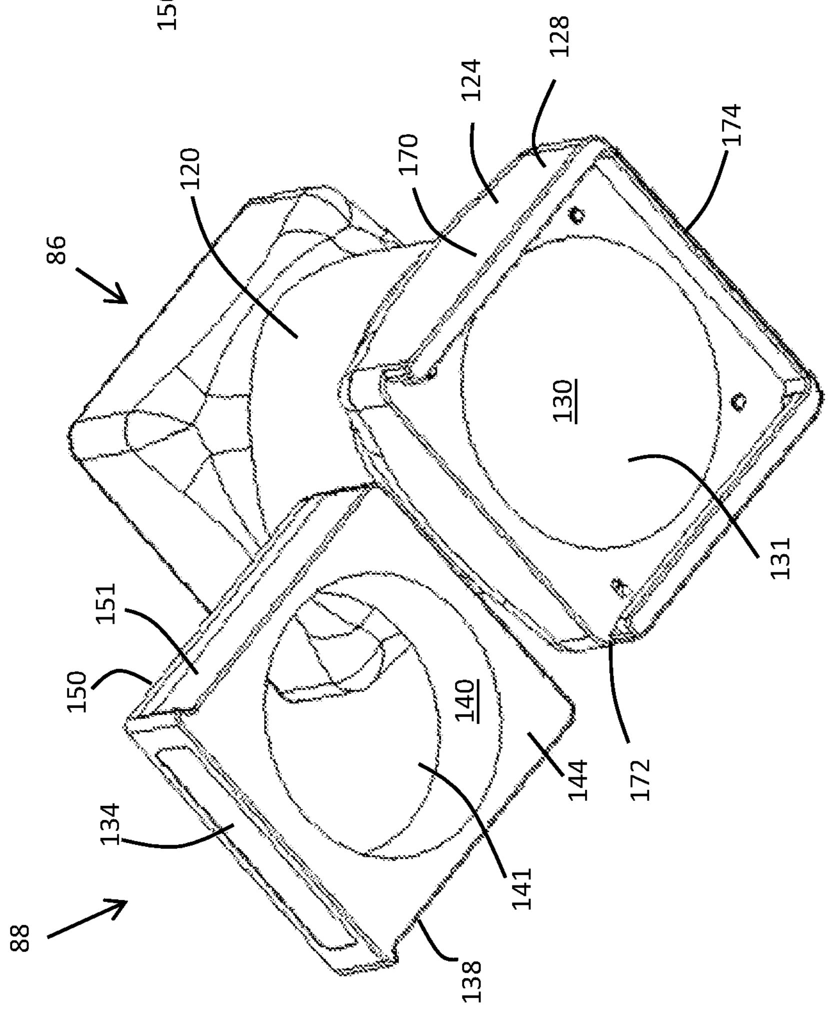
FIG. 19 is a bottom perspective view of the applicator and shield of FIG. 17.

FIGS. 13 and 14 show how applicator 86 and an attached shield 88 are easily mounted and de-mounted from a mounting plate 244 on the lower end of the coupling system 95. To mount, applicator 86 and mounting plate 244 include complementary features that allow applicator 86 to be simply slid onto mounting plate 244 in the direction of arrow 112. Front plate 246 is provided in a different color than mounting plate 244 and housing 83 to help provide a visual guide to mount applicator 86 from the right direction. The leading face of mounting plate 246 has a shallow bevel in order to help guide applicator 86 onto mounting plate 244. At the time of mounting, shield 88 may already be attached to applicator 86. Alternatively, shield 88 may be mounted onto applicator 86 at a later time. Once mounted to mounting plate 244, because second, downstream sub-assembly 98 is rotatable with respect to the first, upstream sub-assembly 96 about axis 211 (see FIGS. 5-8), applicator 86 and shield 88 mounted to the second sub-assembly 98 are rotatable about the same axis 211 as well. Mounting plate 244 and applicator 86 include complementary mounting features (described further below) that help to mount and lock applicator 86 in place.

De-mounting of applicator 86 from mounting plate 244 is easy. Button 110 is pushed to release locking features described below. This allows applicator 86 to be slid off of mounting plate 244 in the direction of arrow 115. Similar, complementary mounting and de-mounting features (described further below) also are used to mount the shield 88 to the applicator 86.

FIGS. 17 to 20 show how shield 88 is easily mounted and de-mounted from applicator 86. To mount, applicator 86 and shield 88 include complementary features that allow shield 88 to be simply slid onto applicator 86 in the direction of arrow 117. Shield 88 and applicator 86 include complementary mounting features (described further below) that help to mount and lock applicator 86 in place.

De-mounting of shield 88 from applicator 86 is easy. Button 110 is pushed to release locking features described below. This allows shield 88 to be slid off of applicator 86 in the direction of arrow 119. Similar, complementary mounting and de-mounting features (described further below) also are used to mount the applicator 86 to mounting plate 244.

FIGS. 5 to 7 and 11-28 show applicator 86 and shield 88 in more detail. Applicator 86 includes body 120 extending from a first inlet end 122 proximal to the coupling system 95 (FIG. 1) to a second, outlet end 124. Head 126 is at first inlet end 122. Head 126 includes mounting features (described below) used to mount applicator head 126 onto the outlet end of the mounting plate 244. Foot 128 is at second outlet end 124. Foot 128 includes mounting features (described below) used to mount applicator foot 128 to shield 88. Applicator 86 includes through aperture 131 defined at least in part by interior surface 130. Aperture 131 has a length that is centered about axis 211. Aperture 131 provides a pathway for the electron beam 16 (FIG. 1) to travel through aperture 131 from the inlet end 122 to the outlet end 124.

Field defining shield 88 (also referred to in the industry as an "insert") has body 134 extending from a first inlet end 136 to a second, outlet end 138. Top face 142 is at inlet end 136. Lower face 144 is at outlet end 138. Shield 88 includes a through aperture 141 defined at least in part by interior wall 140. Aperture 141 has a length that is centered about axis 211. Aperture 141 provides a pathway for the electron beam 16 (FIG. 1) to travel through aperture 141 from the inlet end 136 to the outlet end 138.

FIGS. 13 to 28 show coupling features used to mount and de-mount the applicator 86 from the mounting plate 244 and the shield 88 from applicator 86. The same coupling features are used both respect to the head 126 and foot 128 of the applicator 86. For brevity, the features associated with mounting and de-mounting the applicator 86 and shield 88 at the foot 128 of applicator 86 are described, with the understanding that the features associated with the mounting plate 244 and head 126 of applicator 86 are of the same type.

First, mounting features on the top face 142 of shield 88 are described. Similar features are incorporated into mounting plate 244. Rails 150 extend along opposite sides 151 of shield 88 at the inlet end 136. The top face 142 includes long slot 152, a long wide slot 154, and short slots 156 extending along top face 142 generally parallel to rails 150. The ends of slots 152 and 156 include constrictions 160 defining terminal ends 162. Ramp 164 having backstop 166 is provided on one side proximal to the end of wide slot 154. Pocket 168 is formed behind backstop 166 on one side of wide slot 154.

Mounting features at the foot 128 of applicator 86 are now described. Foot 128 includes sidewalls 170 including slots or tracks 172. The tracks 172 are open at one end and terminate at backwall 174. Foot 128 includes a plurality of plungers 178 that are able to move up and down but are biased, such as by a spring, to be in a lowered position. The plungers 178 are deployed to ride in slots 152 and 156 of shield 88 when shield 88 is mounted to and held on foot 128. The plungers 178 are able to ride up over the constrictions 160 and become releasably held in the pockets 168. Pulling or pushing on shield 88 causes the plungers 178 to engage or be released from the pockets 168. Plungers 178 have tapered heads to facilitate this engaging and releasing function.

Releasable locking functionality is provided by button 110 and shiftable plunger 184. Button 110 engages shiftable plunger 184. Shiftable plunger 184 not only is able to move up and down in a similar spring-biased manner as plungers 178, but also plunger 184 has a side-to-side range of motion based on button actuation. When not actuated (FIGS. 26 and 27), button 110 tends to be in an un-pressed configuration in which plunger 184 is biased to be on the same side of track 154 as ramp 164. In this configuration, plunger 184 is able to ride up ramp 164 when shield 88 is inserted onto foot 128 and then is trapped behind ramp 164 when shield 88 is fully inserted onto applicator 86. This locks shield 88 onto applicator 86. When button 110 is pressed (FIG. 28), plunger 184 is pushed over to the other side of track 154 so as to be clear of ramp 164. This unblocks plunger 184, and hence unlocks shield 88, allowing shield 88 to be removed from applicator 86. Plunger 184 has a rounded head to facilitate this locking and unlocking functionality.

Figure 21:
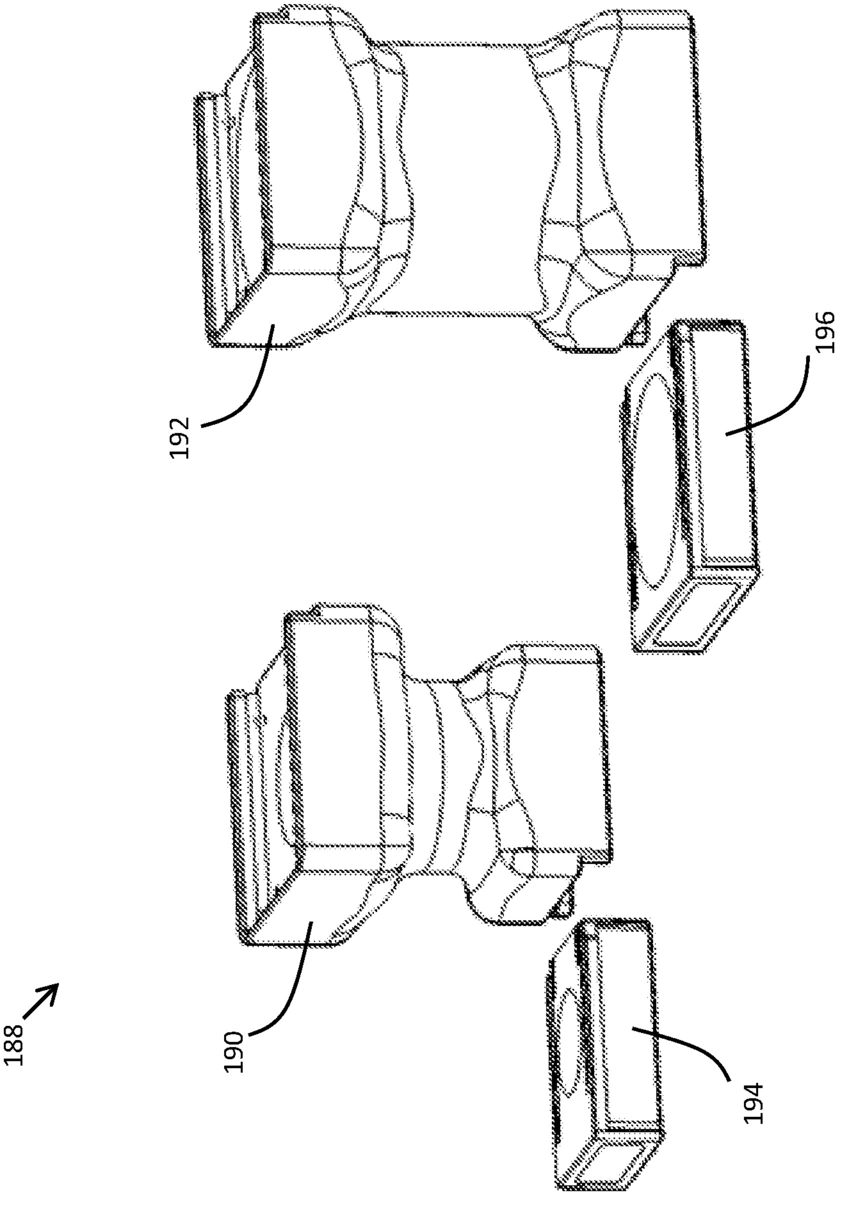
FIG. 21 is a perspective view of a library including applicators and shields of the present invention.
Figure 23:
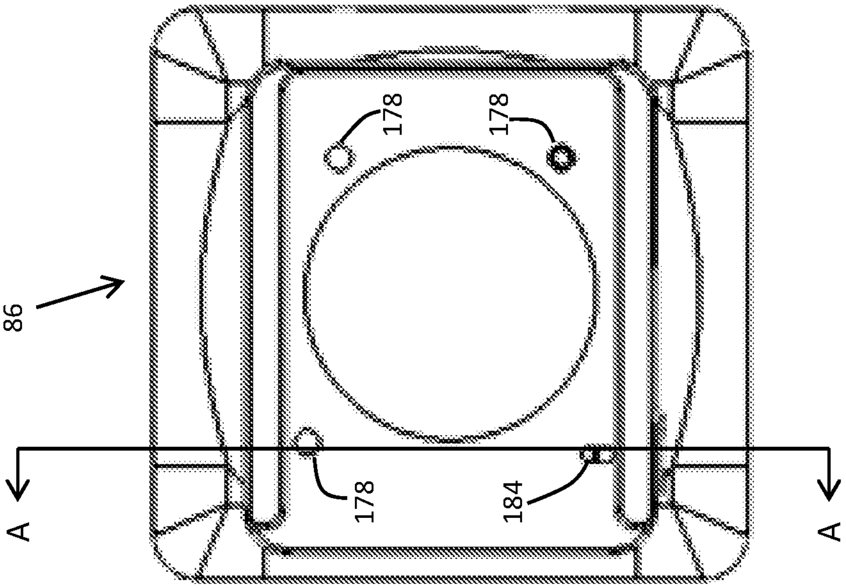
FIG. 23 is identical to the top view of FIG. 22 except for showing cross-section guide lines A-A.
Figure 22:
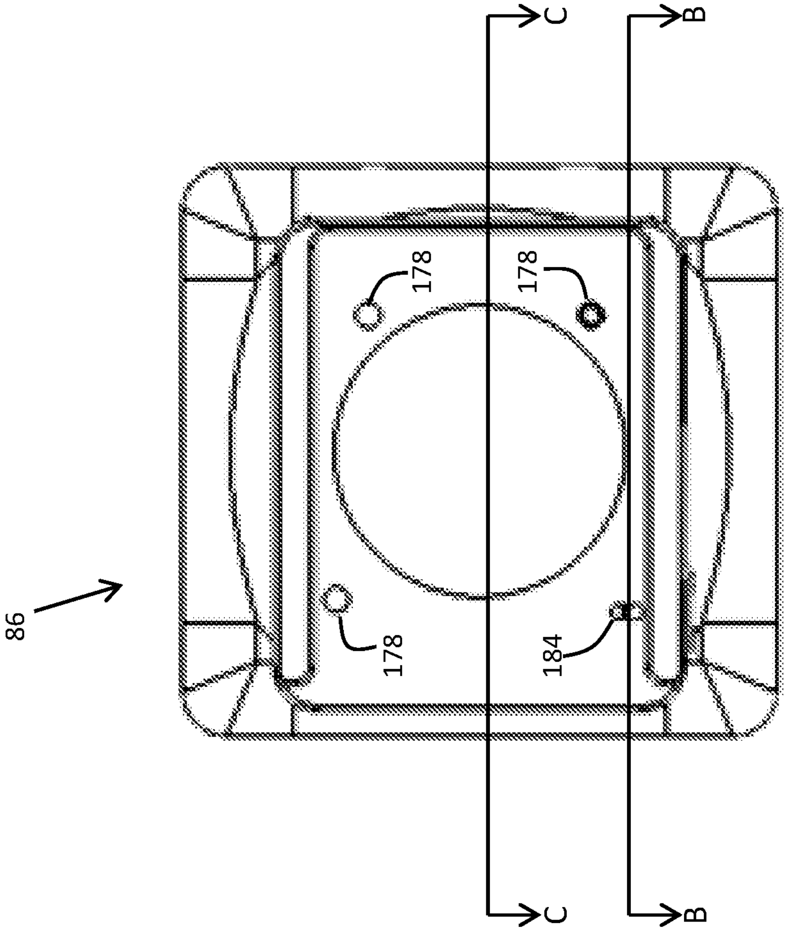
FIG. 22 shows a top view of the applicator of FIG. 11 wherein cross-section guides B-B and C-C are shown.
Figure 25:
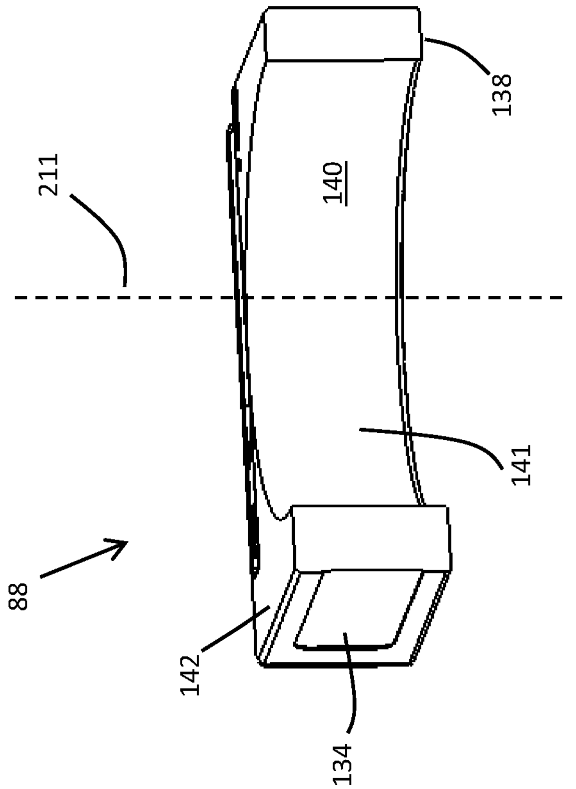
FIG. 25 is a side cross-section perspective view of the shield of FIG. 16 taken along line A-A.
Figure 24:
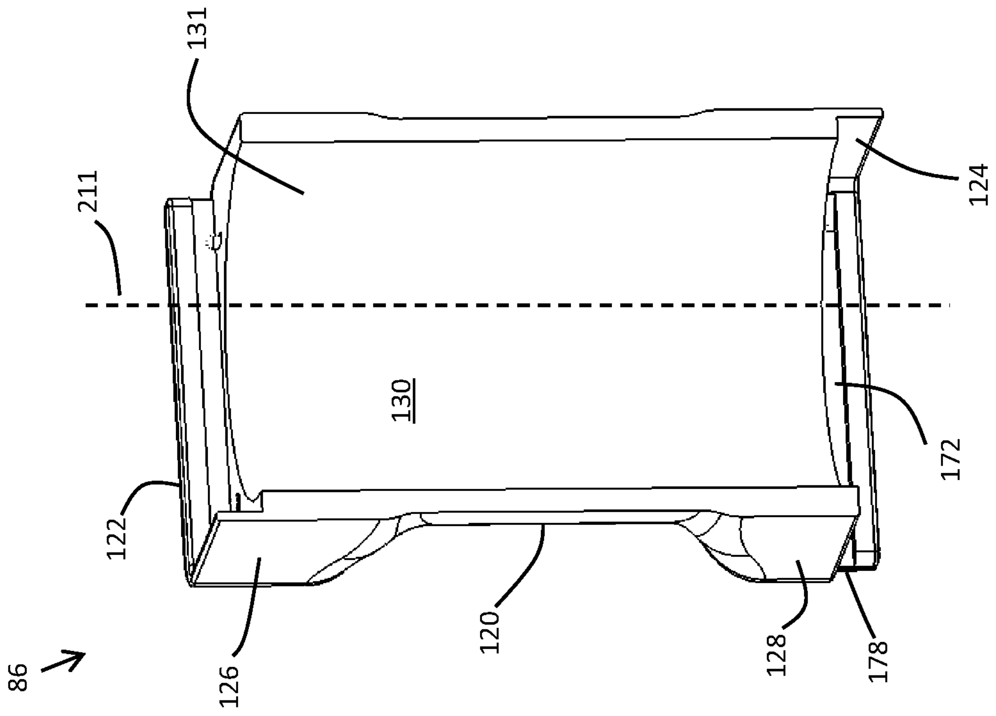
FIG. 24 is a side cross-section perspective view of the applicator of FIG. 22 taken along line C-C.
Figure 29:
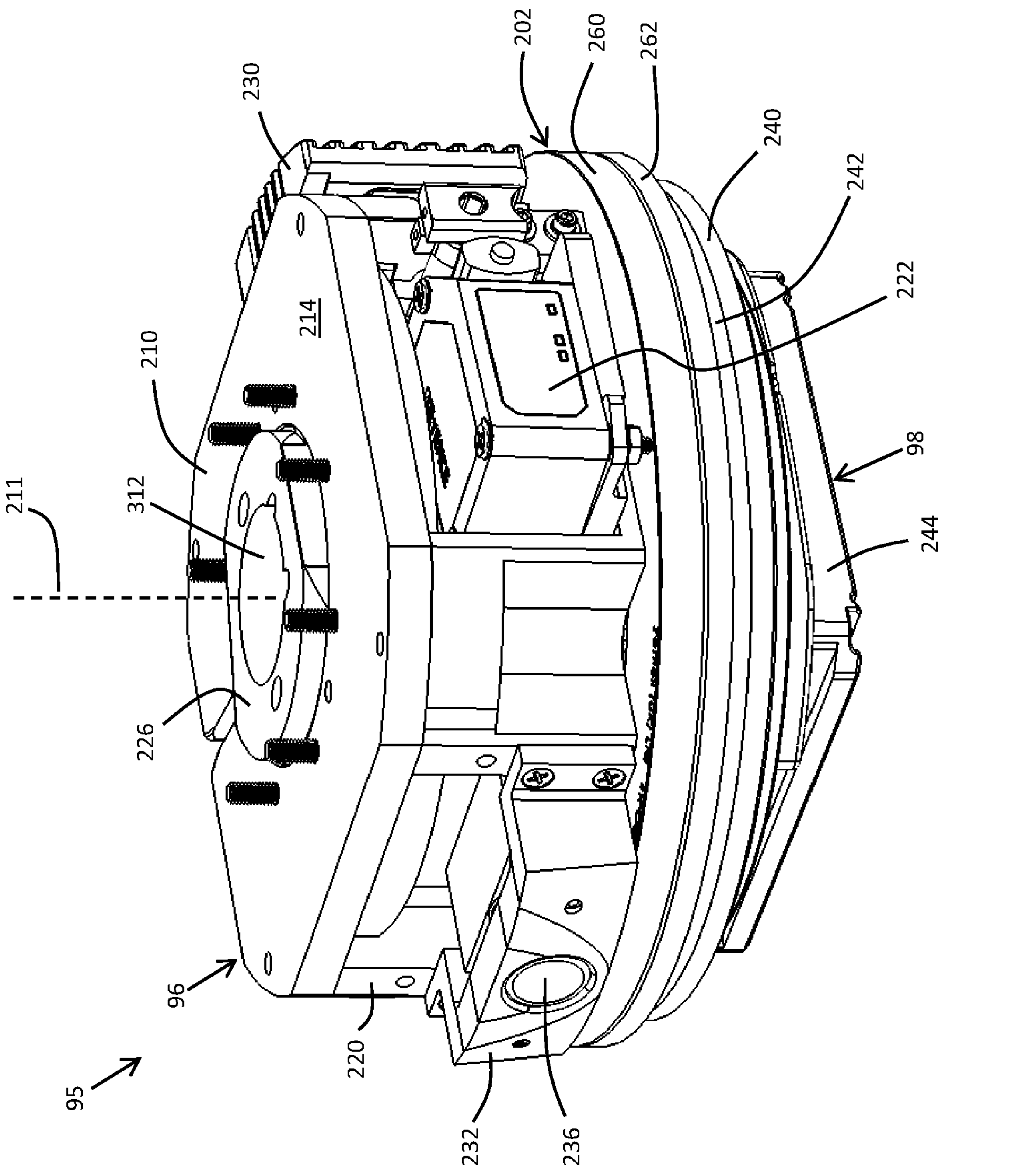
FIG. 29 shows a side perspective view of the rotary coupling system of FIG. 2 in more detail.
Figure 30:
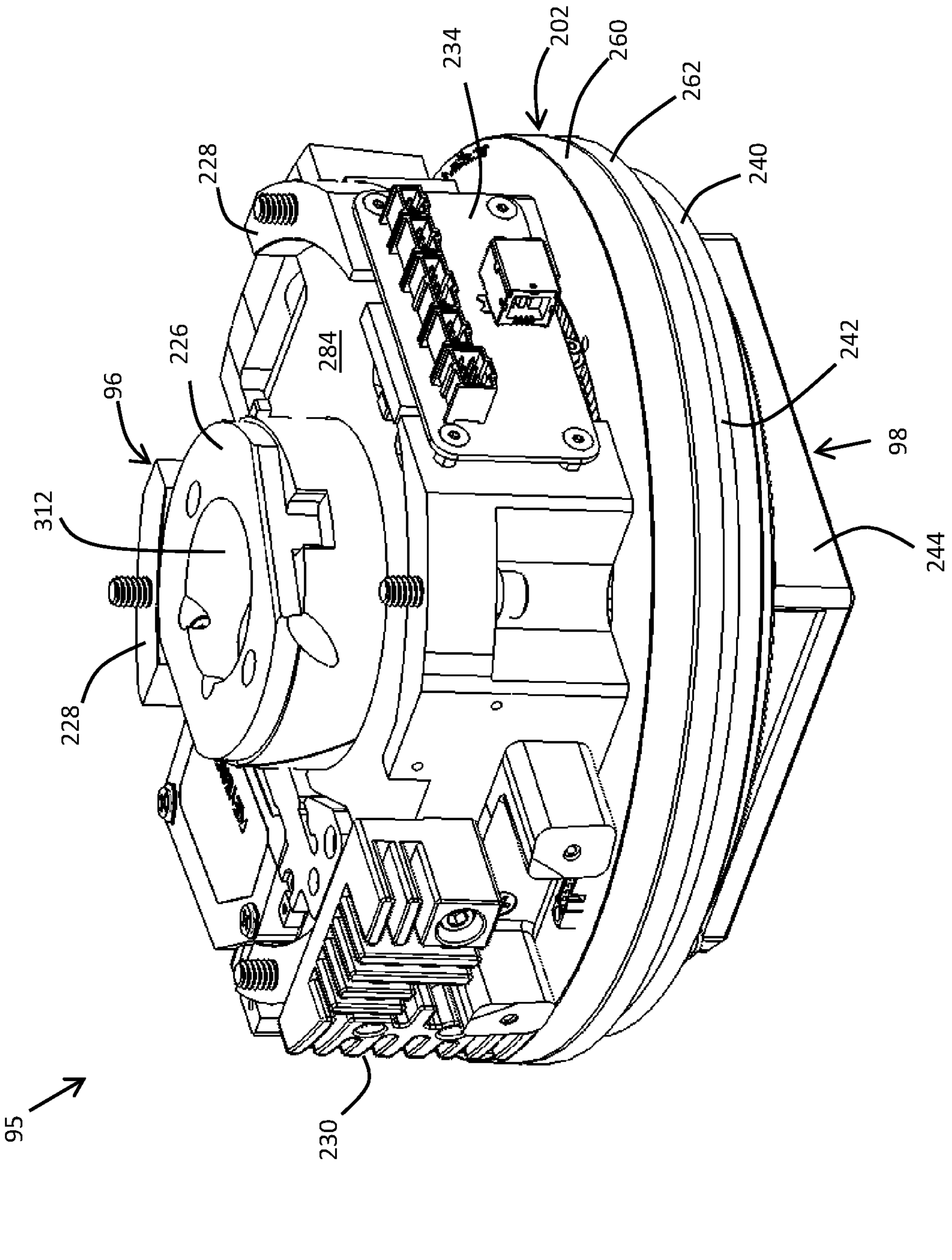
FIG. 30 shows another side perspective view of the rotary coupling system of FIG. 2 in more detail.
Figure 31:
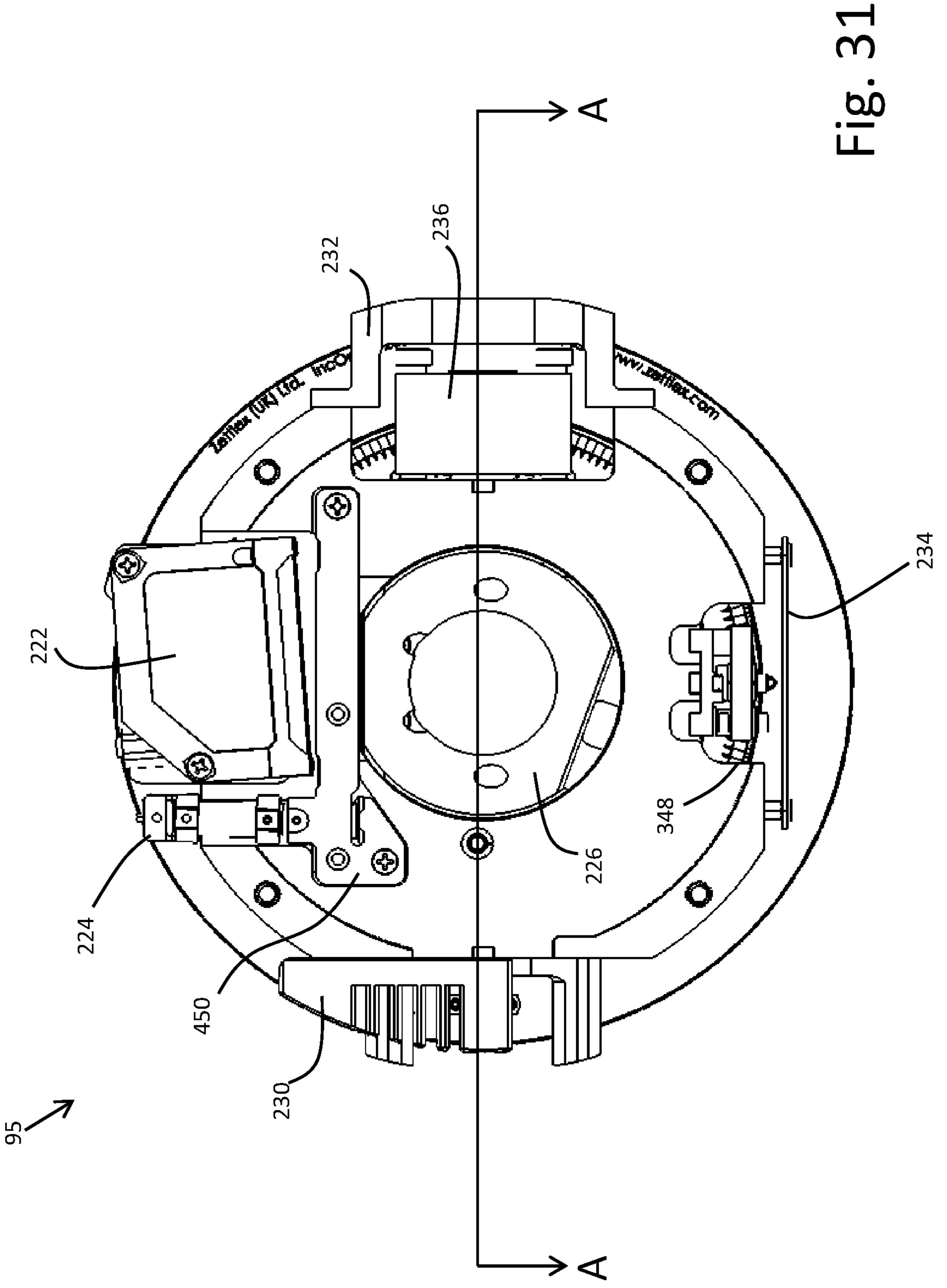
FIG. 31 shows a top view of the rotary coupling system of FIG. 29, wherein cross-a section guide is shown that provide the view of FIG. 35.
Figure 32:
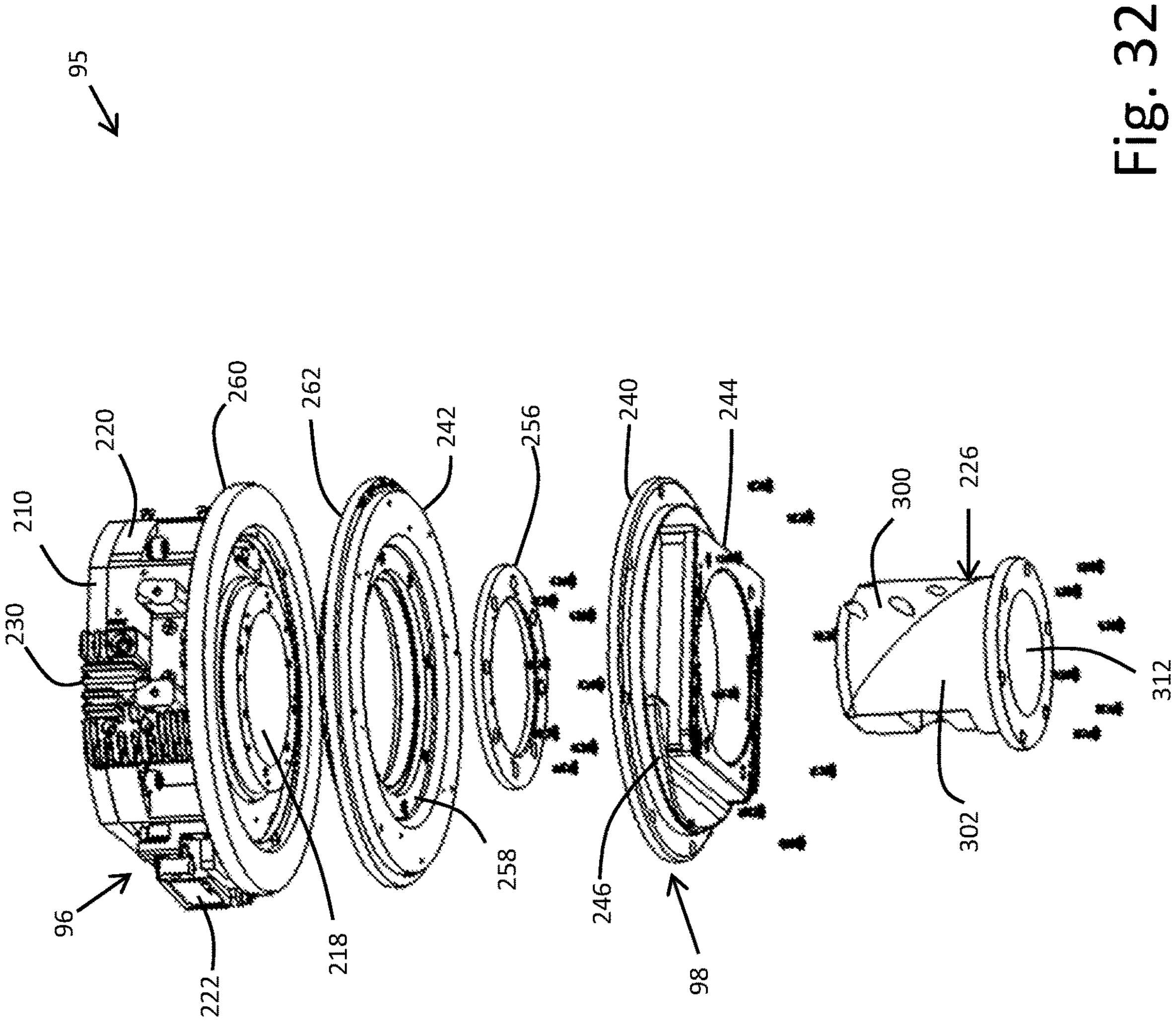
FIG. 32 is an exploded view of the rotary coupling system of FIG. 29, wherein an illustrative number of fasteners used to assemble the exploded components also are shown.
Figure 34:
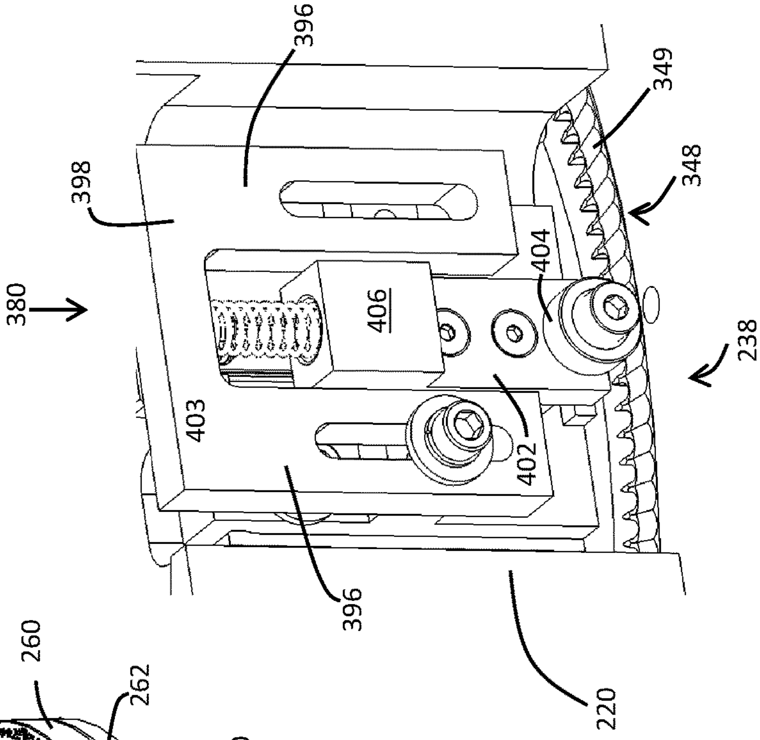
FIG. 34 is a close up perspective view of the rotary indexing components shown in FIG. 33.
Figure 33:
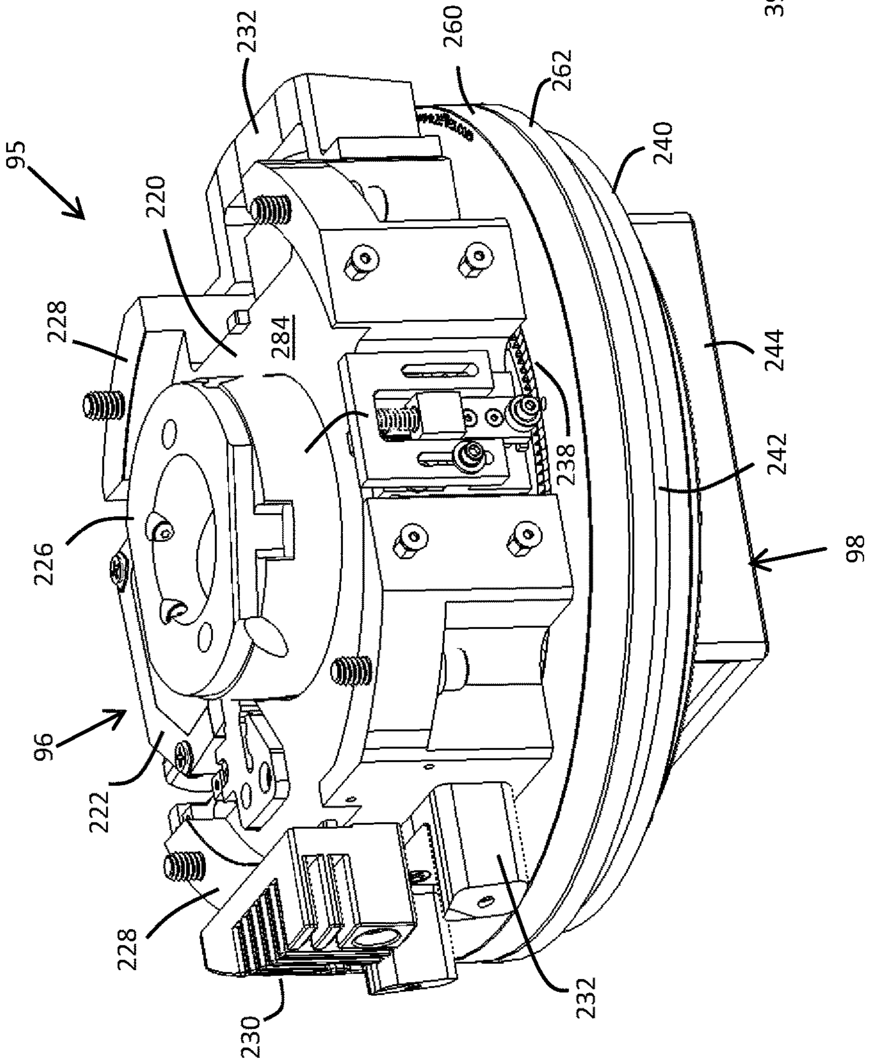
FIG. 33 is a side perspective view of the rotary coupling system of FIG. 29 with some components removed to show the underlying components of the rotary indexing system.
Figure 35:
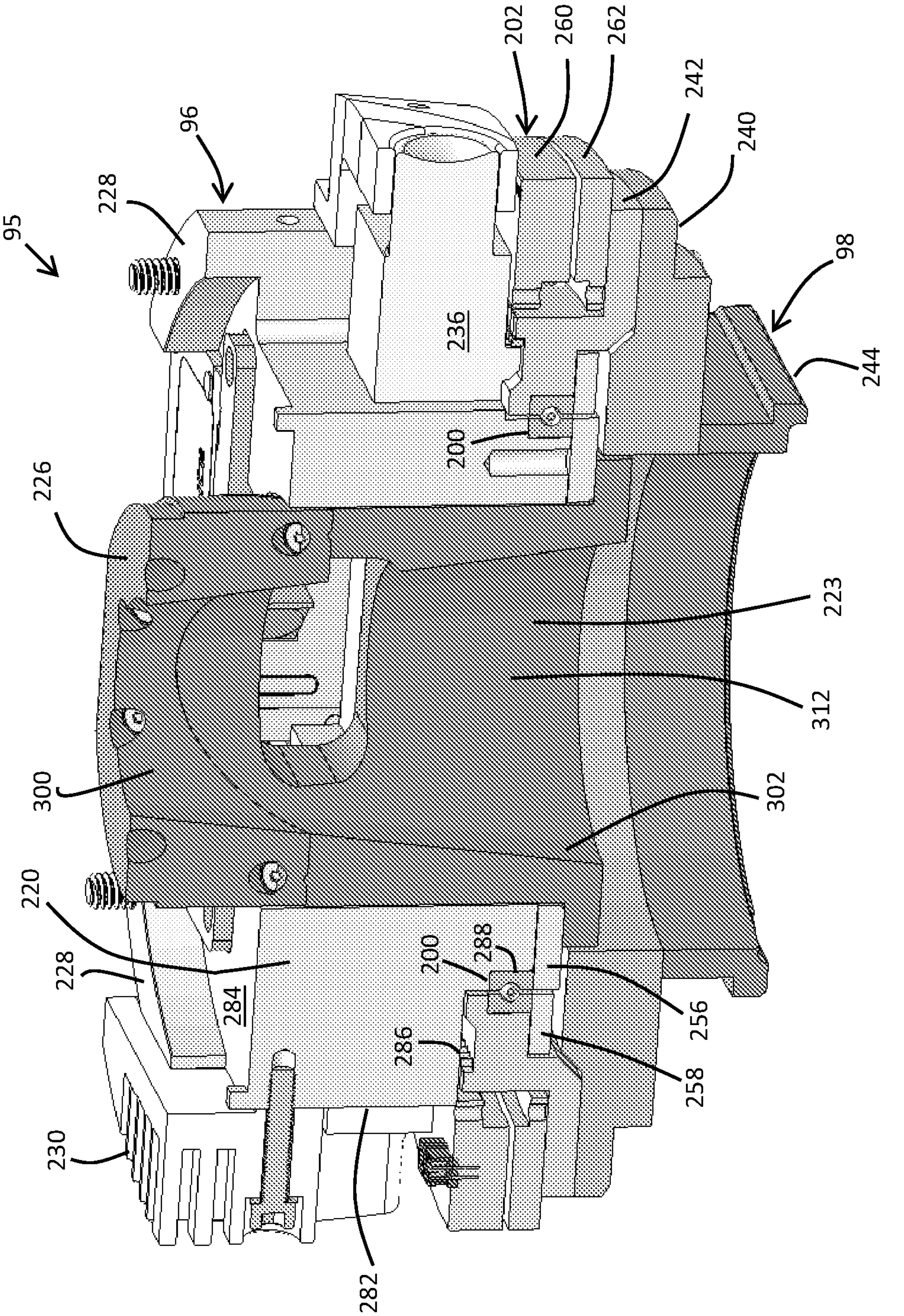
FIG. 35 shows a cross-sectional side perspective view of the rotary coupling system of FIG. 29 taken along line A-A of FIG. 31.
Figure 38:
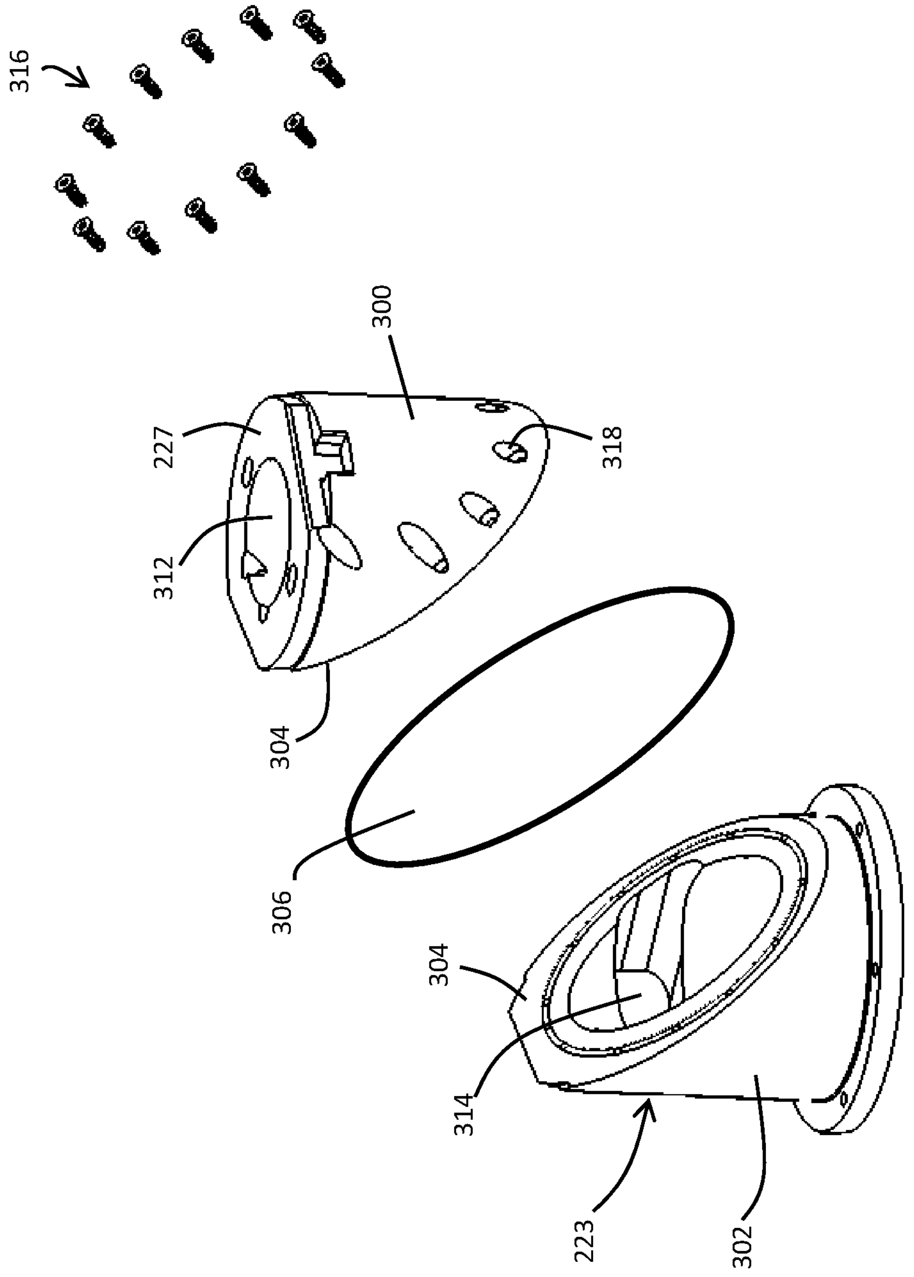
FIG. 38 is an exploded view of the central core and mirror assembly of FIG. 37, wherein an illustrative number of fasteners used to assemble the exploded components also are shown.
Figure 39:
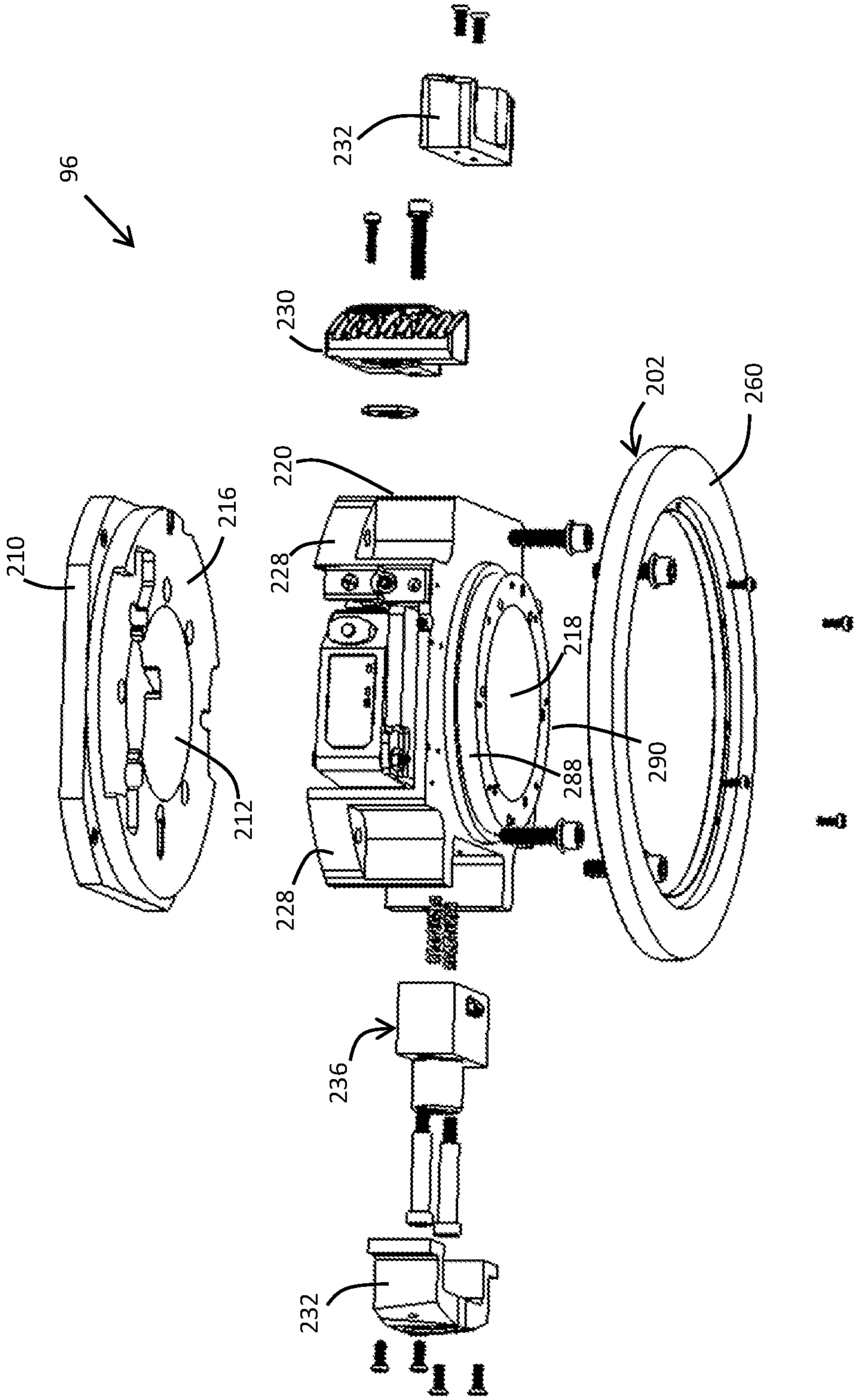
FIG. 39 is an exploded side perspective view of a portion of the upper sub-assembly of the rotary coupling system of FIG. 29, wherein an illustrative number of fasteners used to assemble the exploded components also are shown.
Figure 40:
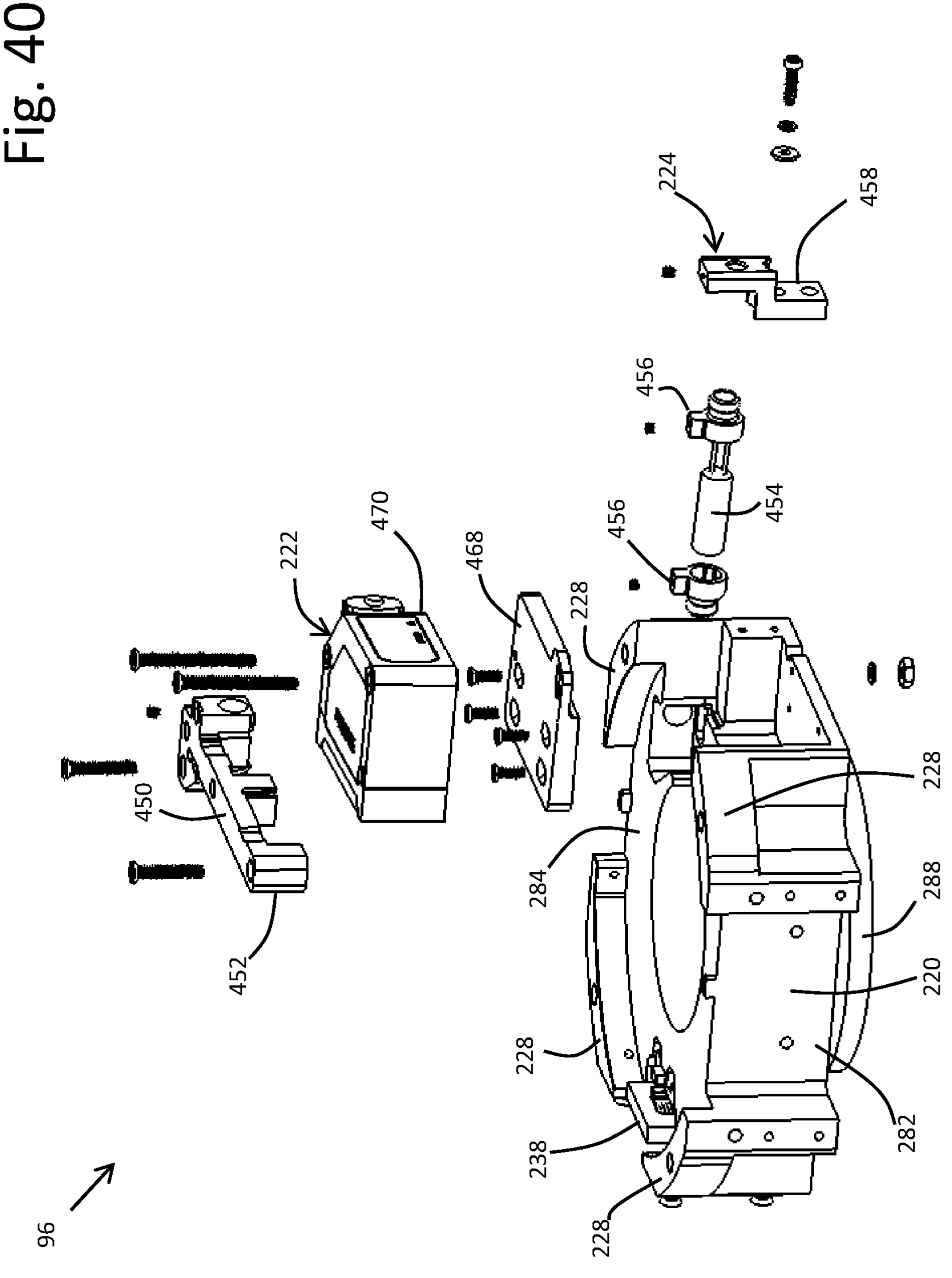
FIG. 40 is another exploded side perspective view of a portion of the upper sub-assembly of the rotary coupling system of FIG. 29, wherein an illustrative number of fasteners used to assemble the exploded components also are shown.
Figure 41:
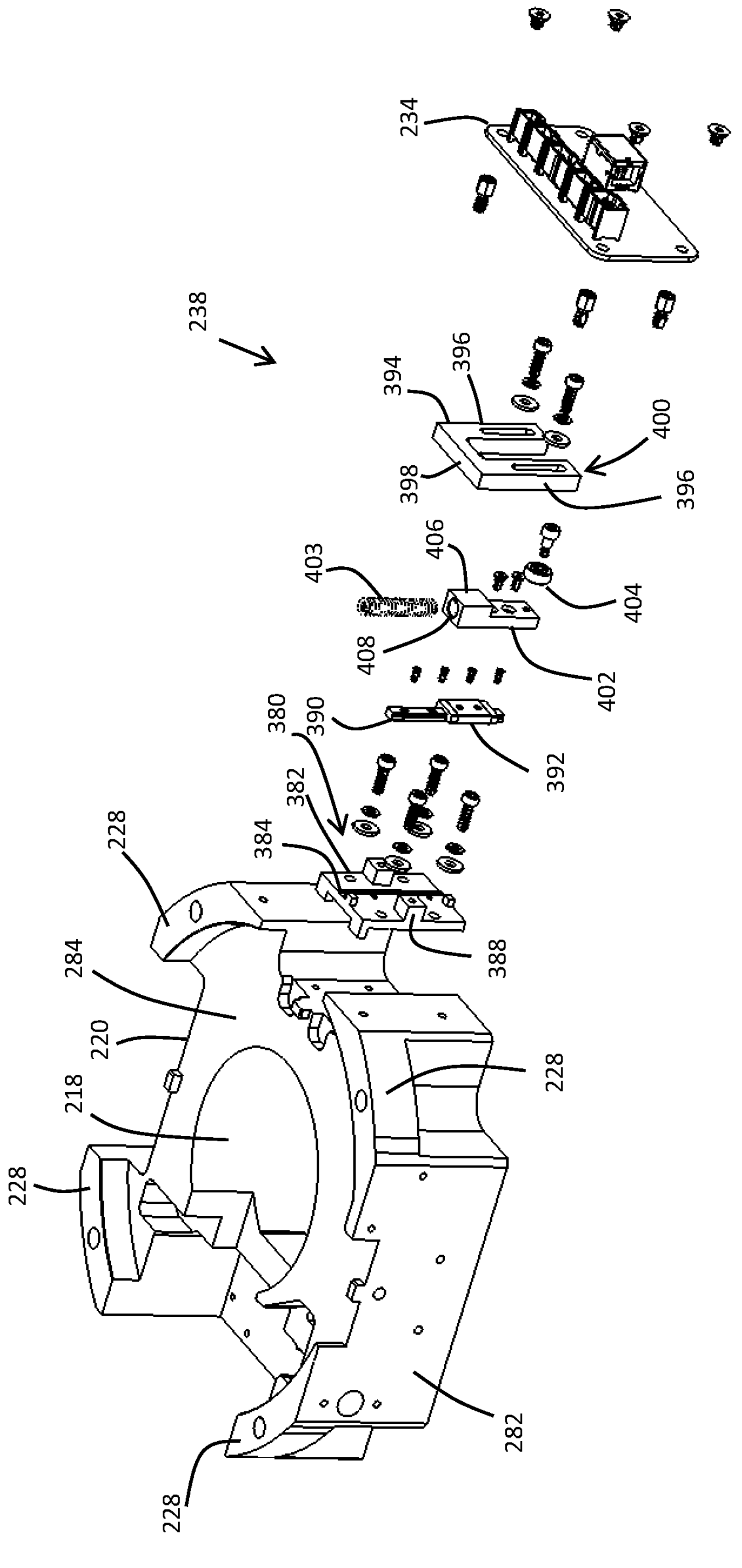
FIG. 41 is another exploded side perspective view of a portion of the upper sub-assembly of the rotary coupling system of FIG. 29, wherein an illustrative number of fasteners used to assemble the exploded components also are shown.
Figure 42:
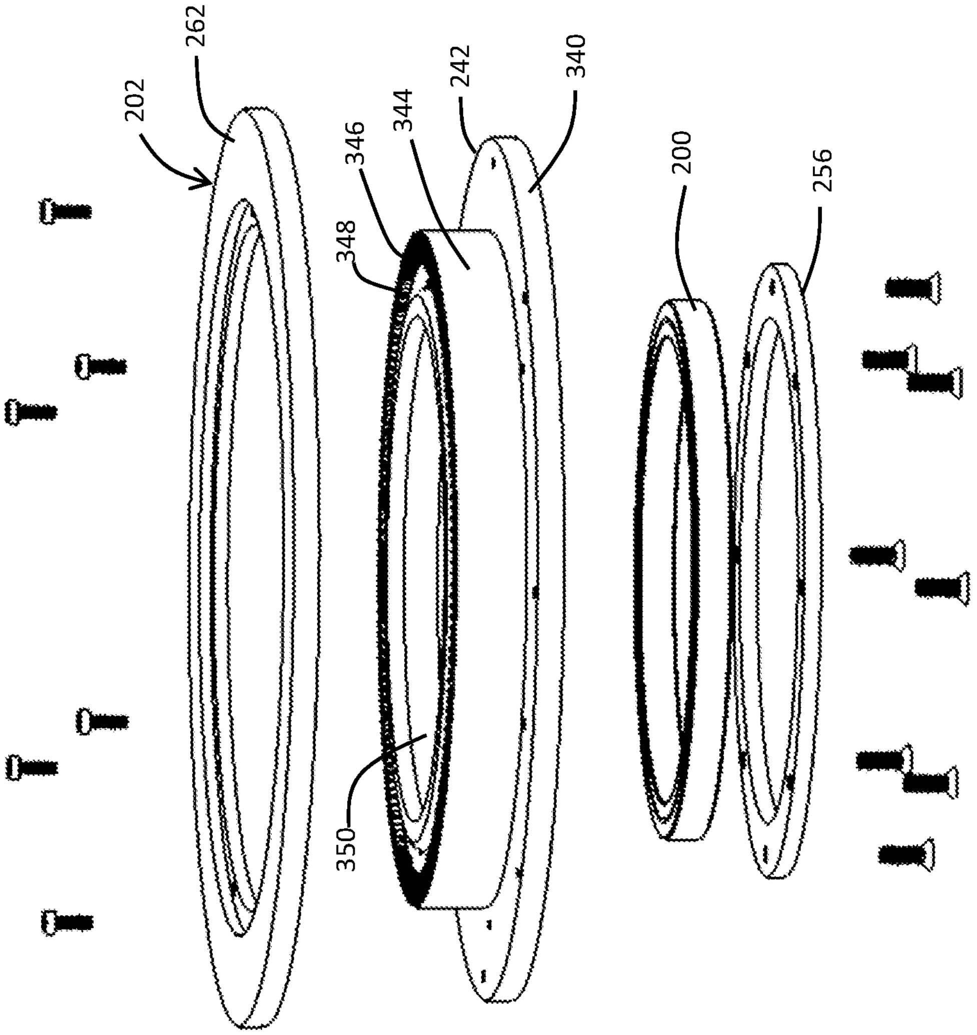
FIG. 42 is an exploded perspective view of a portion of the lower sub-assembly of the rotary coupling system of FIG. 29 shown in more detail, wherein an illustrative number of fasteners used to assemble the exploded components also are shown.
Figure 44:
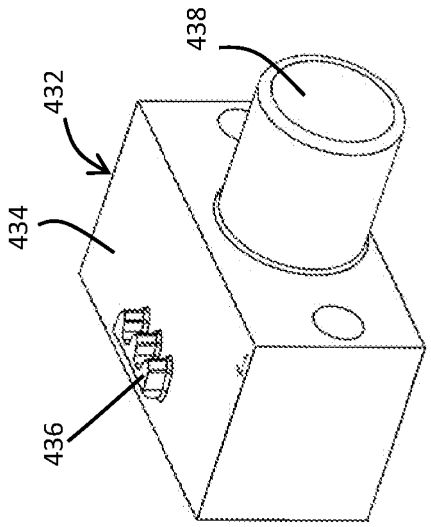
FIG. 44 is a bottom perspective view of the button actuated locking device of FIG. 43.
Figure 43:
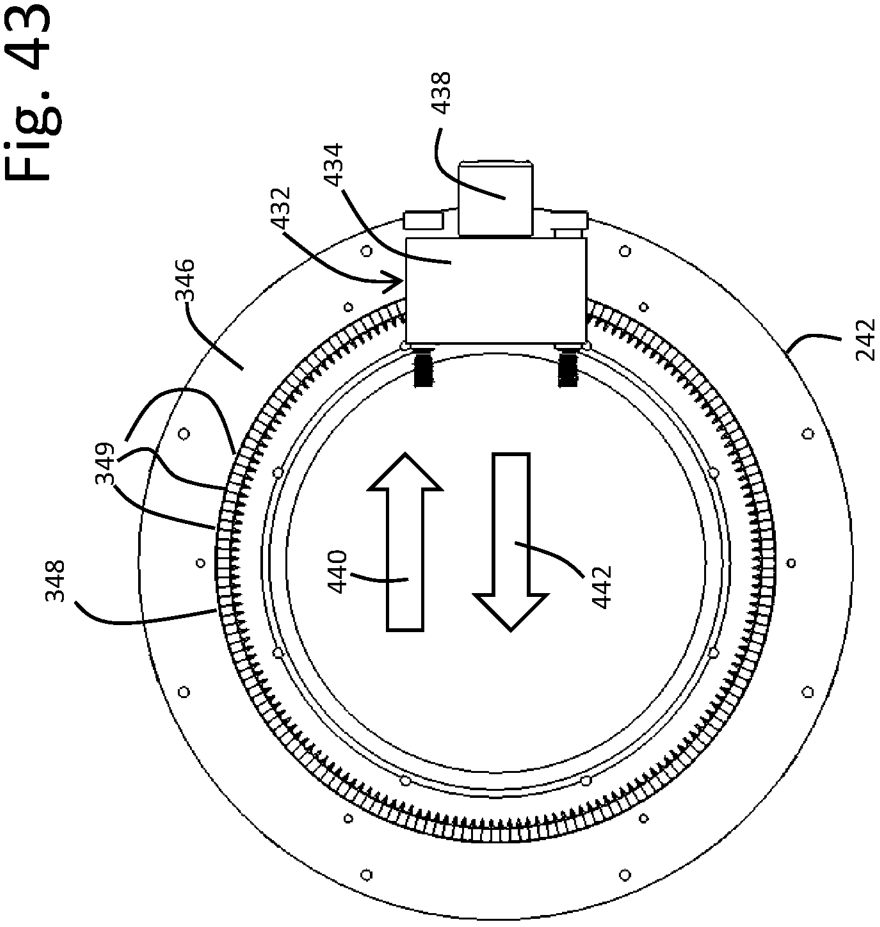
FIG. 43 is a top view of components of the rotary coupling system of FIG. 29 that provide rotary locking functionality.
Figure 45:
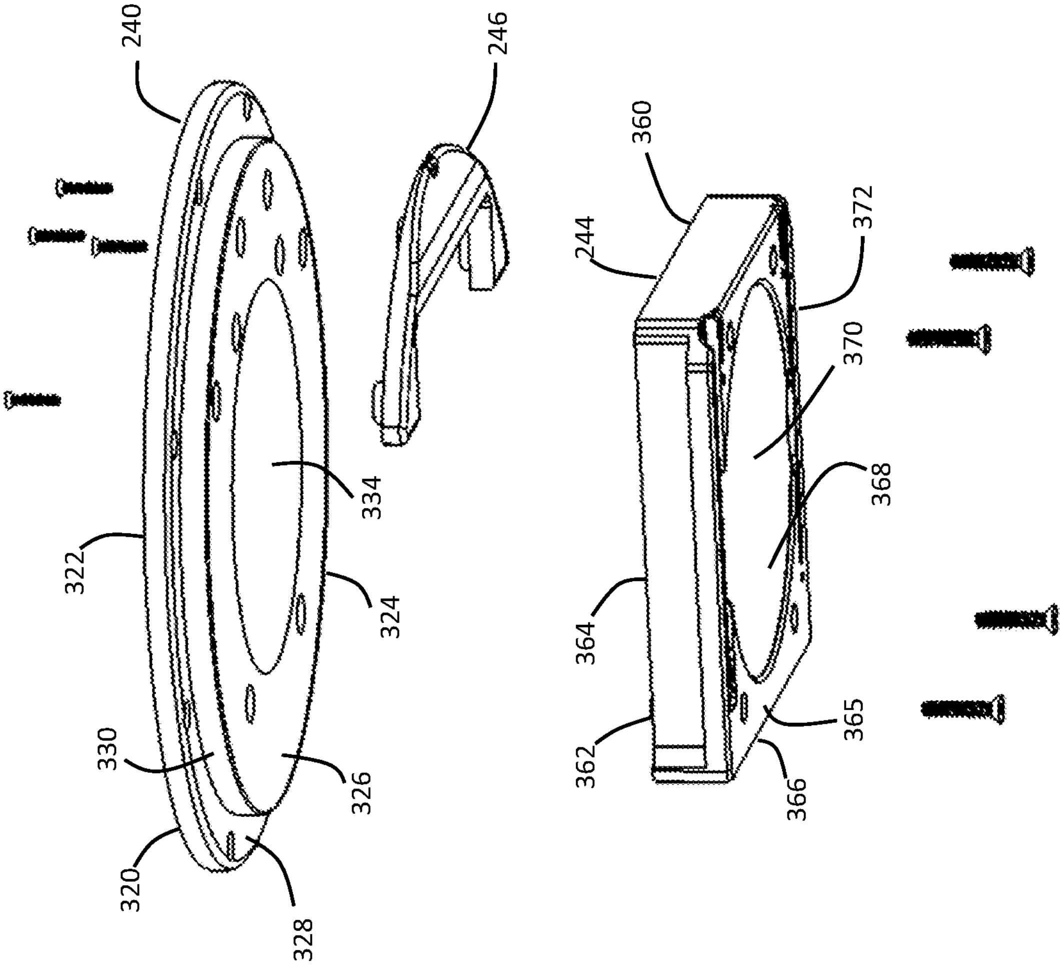
FIG. 45 is an exploded perspective view of a portion of the lower sub-assembly of the rotary coupling system of FIG. 29 shown in more detail, wherein an illustrative number of fasteners used to assemble the exploded components also are shown.

FIG. 21 schematically shows how system 10 of FIG. 1 may include a library 188 of absorbers and shields. Such a library may include two or more shields 194 and 196 and two or more applicators 190 and 192. Each type of applicator may be interchangeably attached to two or more different shields 194 and 196. In some modes of practice, different sized applicators 190 and 192 may be compatible with different sets of shields 194 and 196, respectively. The applicators 190 and 192 and shields 194 and 196 may differ in terms of a variety of characteristics such as material(s) of construction, length, diameter, geometry of the central aperture through which the ebeam travels, interior accessories, exterior accessories, and the like. The components of a library may include detection features so that system 10 can automatically detect which component is used and thereby provide custom interfaces or choices associated with the identified component.

For purposes of illustration, FIG. 21 shows library 188 including a small applicator 190 and a large applicator 192. One or more small shields 194 are associated with small applicator 190. One or more larger shields 196 are associated with the large absorber 192.

FIGS. 5-7, 12, and 29-45 provide an overview of the coupling system 95 and its main components. Coupling system 95 generally includes a first, upstream sub-assembly 96 that is rotatably coupled to a second, downstream sub-assembly 98. A rotary encoder 202 is incorporated into coupling system 95 so that the relative rotation between sub-assembly 96 and sub-assembly 98 can be automatically monitored and measured. System 95 includes a main central aperture 209 and a main central axis 211. Central aperture 209 provides a pathway for ebeam 16 (FIG. 1) to pass through from inlet 213 to outlet 215. Inlet 213 is coupled to upstream components of unit 26 (FIG. 1). Outlet 215 is coupled to applicator 86. Automated functionality (described below) for measuring distance to the target site 12 (FIG. 1) and automated functionality (described below) for aiming the ebeam 16 and illuminating the target site 12 are incorporated into the system 95.

First, upstream sub-assembly 96 generally includes an upper mounting plate 210 used to attach sub-assembly 96 to upstream components. Mounting plate 210 includes a central aperture centered about axis 211, an upper or upstream face 214, and a lower or downstream face 216. Mounting plate 210 is coupled to mounting bosses 228 on main body 220. Main body 220 includes a central aperture 218 that houses central core and mirror assembly 226. Central core and mirror assembly 226 in turn has central aperture 312 along central axis 211 through which the ebeam 16 (FIG. 1) travels.

Main body 220 incorporates many systems that provide several advantageous functions and capabilities. Distance detection system 222 and optical illumination system 224 are integrated with main body 220. Additionally, a rotary locking and release mechanism 236 and rotary indexing system 238 also are integrated with main body 220. Heat sink 230 is provided to help dissipate heat generated from the LED light source 460. A controller 234 is mounted to main body 220 as well.

A portion of the rotary encoder 202 is also mounted to main body 220. Rotary encoder 202 includes stator ring 260 and rotor ring 262. Stator ring 260 is mounted to main body 220, while rotor ring 262 is mounted to the second-subassembly 98. The rotary encoder 202 incorporates electronic capabilities so that the rotational position of stator ring 260 relative to the rotor ring 262 is easily monitored and measured. The result is that the relative rotation of the sub-assembly 96 relative to the sub-assembly 98 is easily and accurately monitored, such as to a fraction of a rotational degree if desired. In some embodiments, the rotary encoder 202 includes absolute encoder functionality so that the rotation position is known even if power is lost. Mounting features are used to help mount housing 83 (FIG. 11) onto coupling system 95. The main components and functions of first, upstream sub-assembly 96 are described in more detail below.

Lower, downstream sub-assembly 98 includes several main components as well. These include rotary base plate 240, rotor 242, mounting plate 244, and front plate 246. Rotor ring 262 of rotary encoder 202 is incorporated into sub-assembly 98 as well. Lower sub-assembly 98 includes central aperture 248 having central axis 211. The main components and functions of second, downstream sub-assembly 98 are described in more detail below.

Annular ring bearing 200 rotatably couples first, upstream sub-assembly 96 to second, downstream sub-assembly 98. This allows sub-assembly 96 to rotate relative to subassembly 98. In practice, sub-assembly 96 is attached to a larger assemblage of upstream components of unit 26 (FIG. 2), while second sub-assembly 98, the applicator 86, and shield 88 are rotatable on demand about axis 211. Ring bearing 200 includes inner race 250, outer race 252, and ball bearings 254. Inner race clamp 256 holds inner race 250 in place with respect to first sub-assembly 96. Outer race clamp 258 holds outer race 252 in place with respect to second sub-assembly 98.

Figure 5:
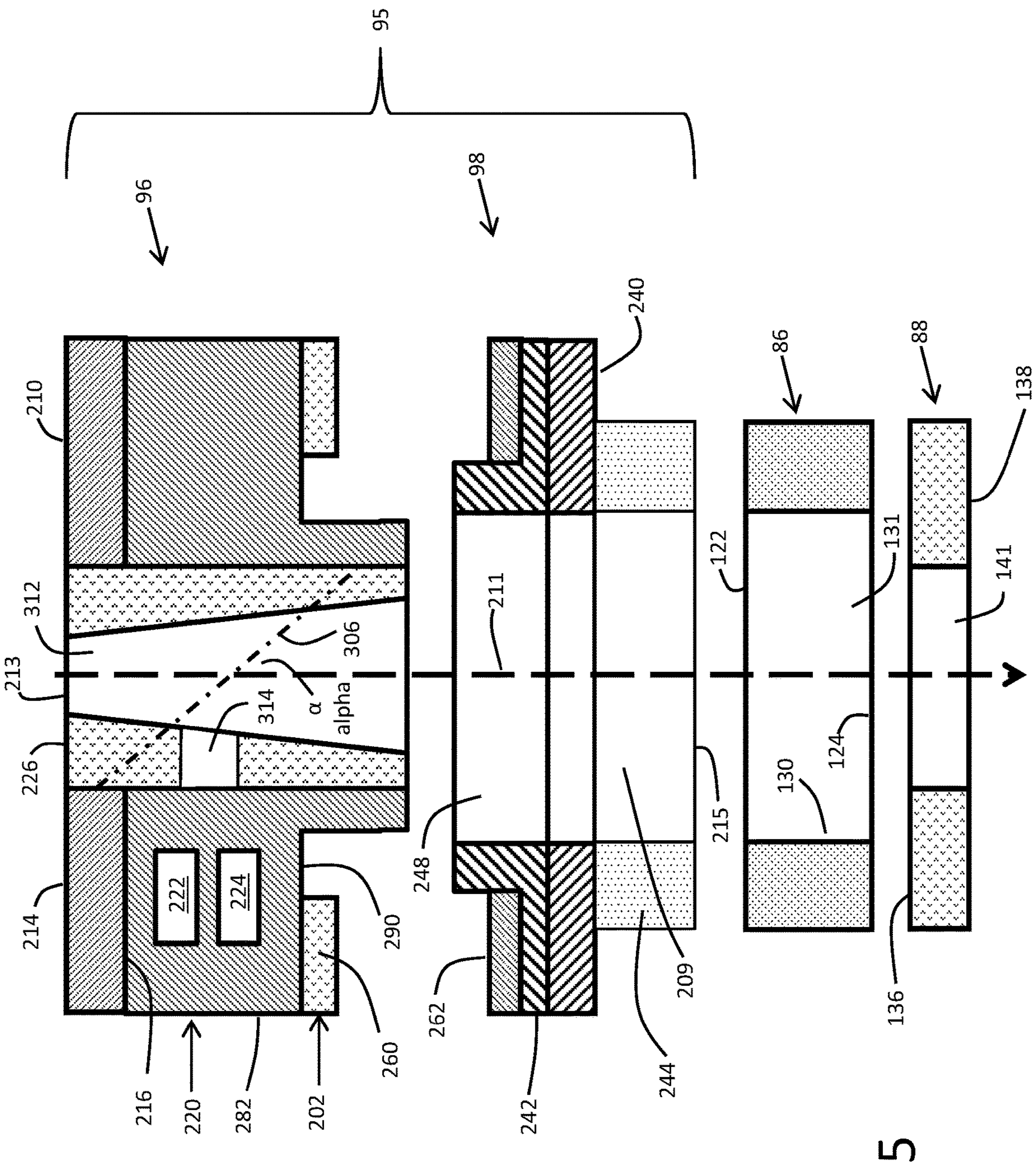
FIG. 5 schematically shows an exploded, side cross-section view of the rotary coupling system of the present invention of FIG. 2 in alignment with field defining members in the form of an applicator and a shield.
Figure 6:
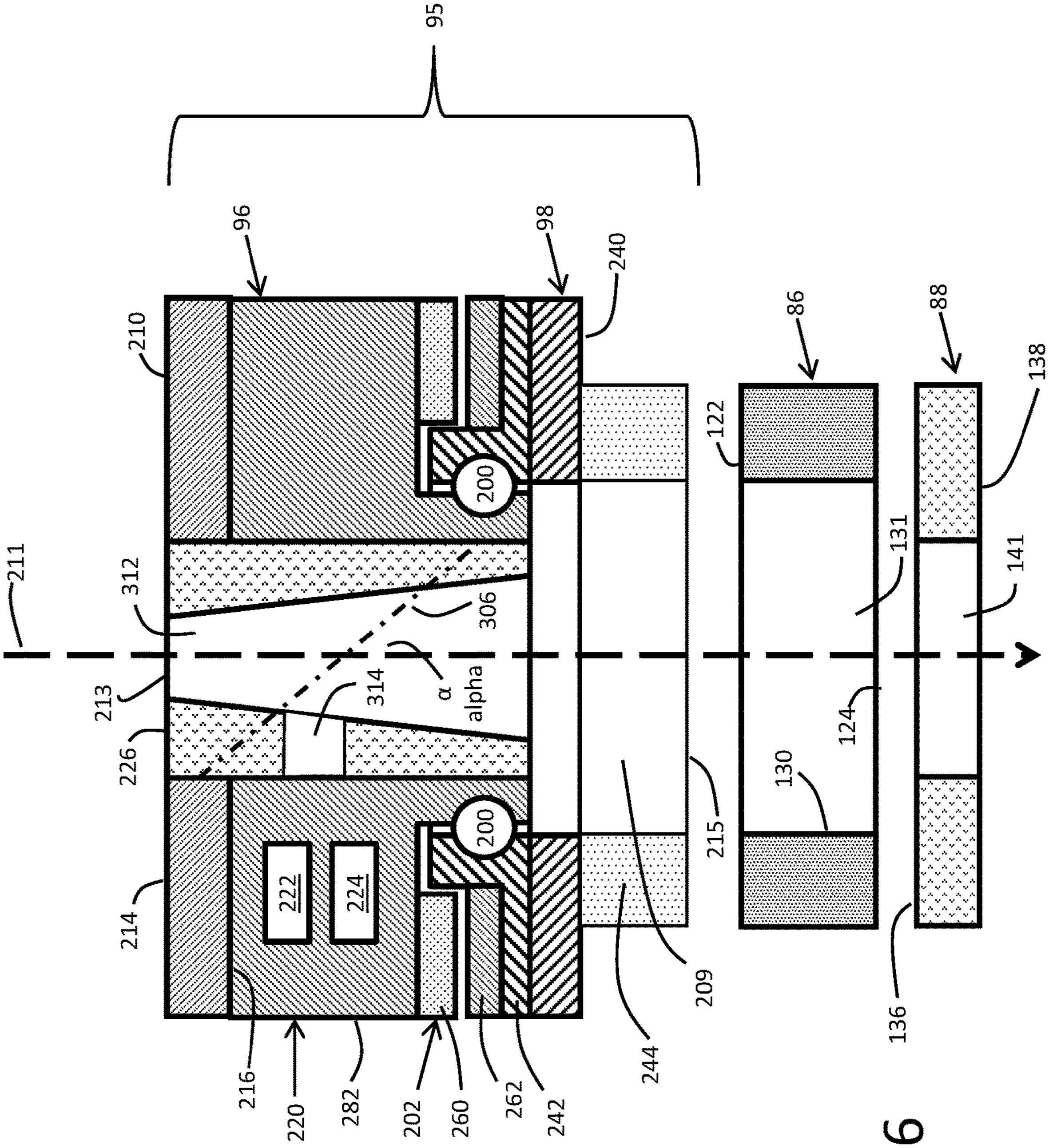
FIG. 6 schematically shows a side cross-section view of the rotary coupling system of the present invention of FIG. 2 in alignment with field defining members in the form of an applicator and a shield.
Figure 7:
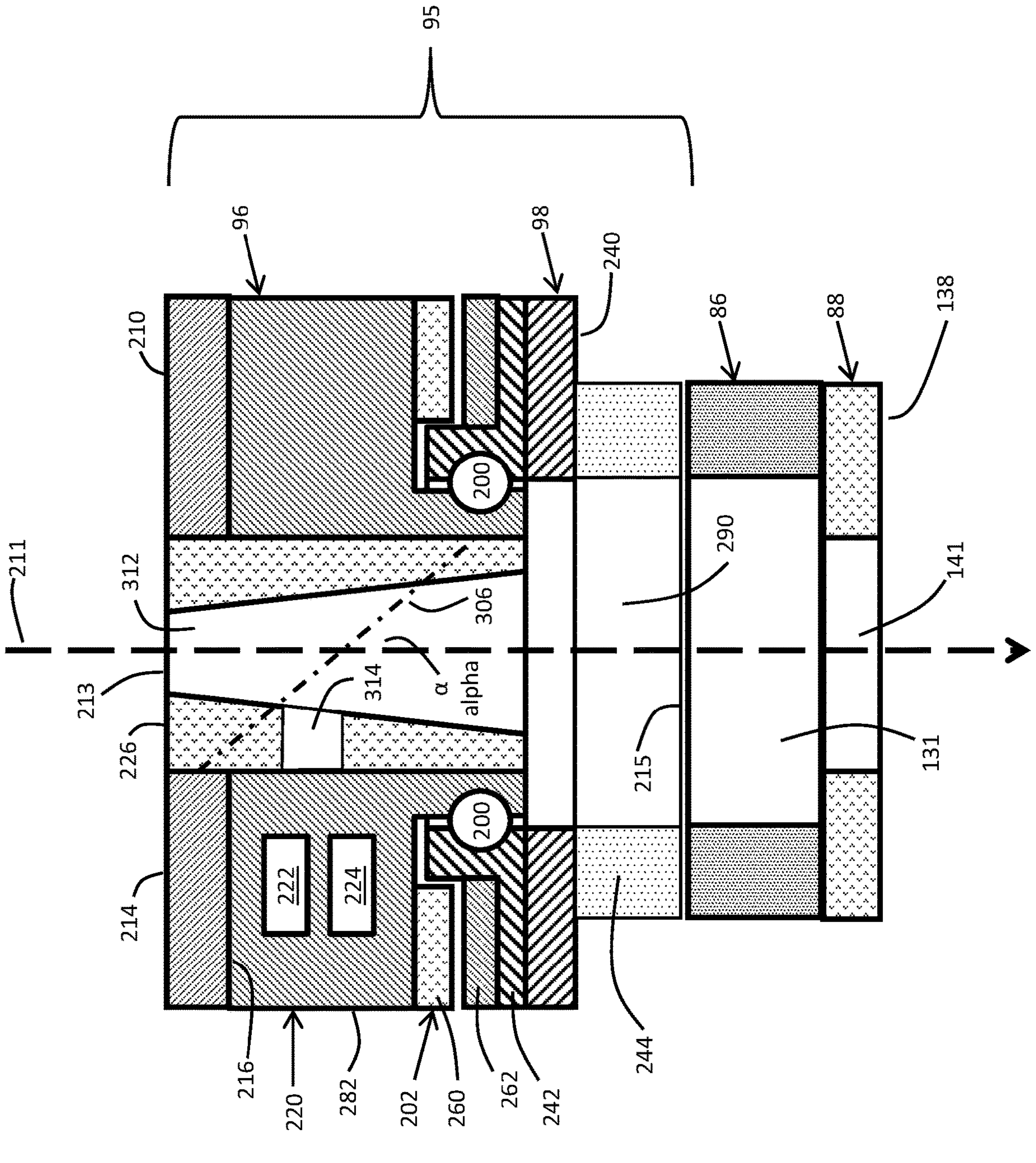
FIG. 7 schematically shows an exploded, side cross-section view of the rotary coupling system of the present invention of FIG. 2 with field defining members in the form of an applicator and a shield mounted to the rotary coupling system.

FIGS. 5 to 8 provide an overview of how the main components of the first sub-assembly 96, second sub-assembly 98, applicator 86, and shield 88 are assembled to provide the applicator 86 and attached shield 88 with rotational functionality. FIG. 5 shows the separate components 96, 98, 86, and 88 separately aligned on axis 211. In FIG. 6, the sub-assemblies 96 and 98 are rotatably coupled together by ring bearing 200. This assembly provides the coupling system 95. In FIG. 7, the applicator 86 is attached to the lower sub-assembly 98, and the shield 88 is attached to the applicator 86.

Figure 8:
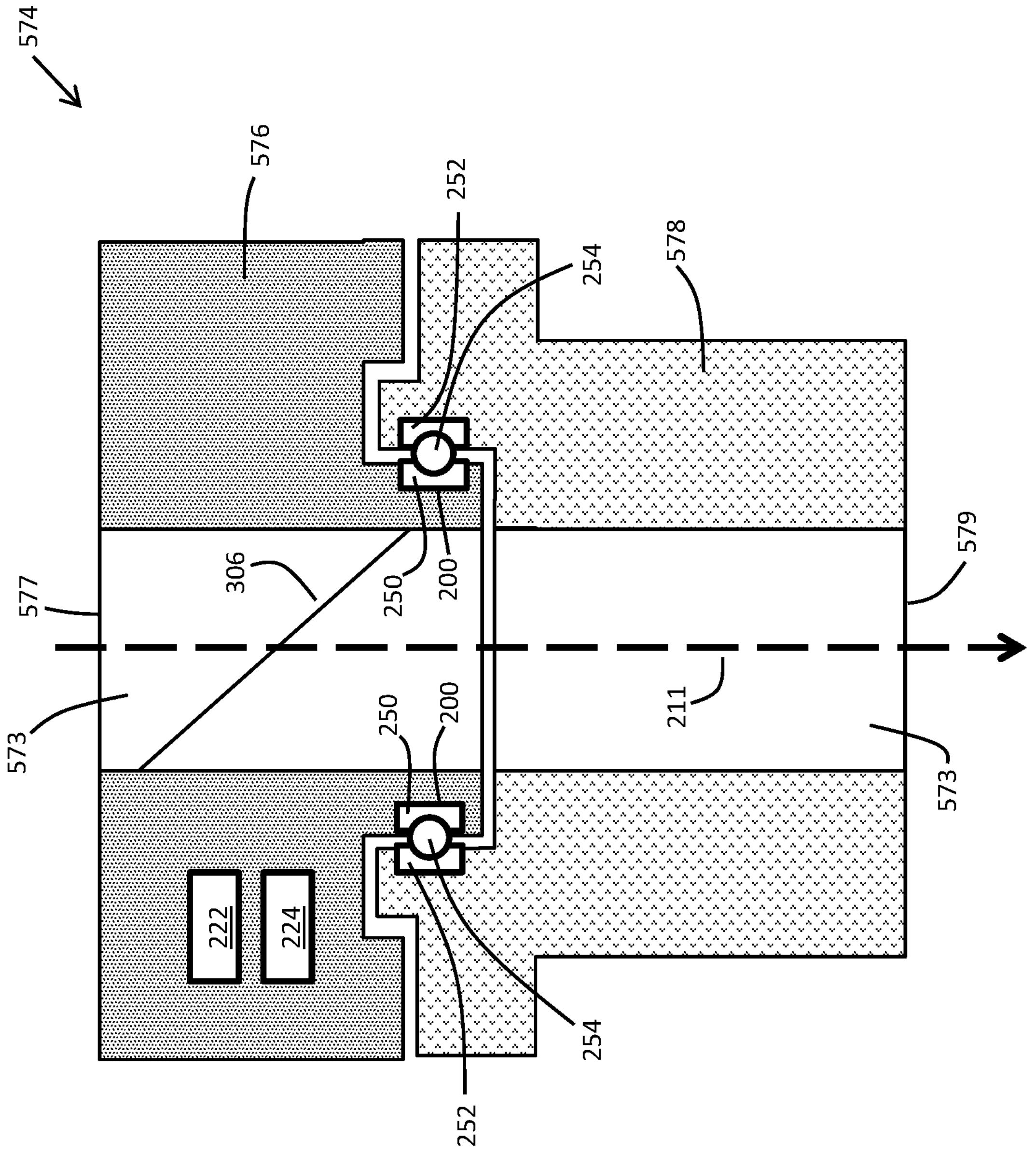
FIG. 8 schematically shows an alternative side cross section view of the assembled components of FIG. 7.

As shown in FIG. 8, the resultant assembly 574 can be viewed has having a first unit 576 rotatably coupled to a second unit 578. The first unit 576 corresponds to the first, upstream sub-assembly 96. The second unit 578 can be viewed as a singly assembly that corresponds to the assembled second, downstream sub-assembly 98, the applicator 86, and the shield 88. The assembly includes the main central aperture 573 having central axis 211 through which electron beam 16 (FIG. 1) passes from inlet 577 to outlet 579.

FIGS. 5-7, 29-33, 35-39, 40, 41 show the main body 220 in more detail. Main body 220 includes sidewall 282, top 284, shoulder 286, neck 288, and lower face 290. Mounting bosses 218 on the top 284 are used to attach the mounting plate 210. Central aperture having central axis 211 is provided to house the central core and mirror assembly 226.

FIGS. 5-7, 29-33, 35-38 show the central core and mirror assembly 226 in more detail. Central core and mirror assembly 226 has body 223 having a central aperture 312 extending along central axis 211. Central aperture 312 provides a pathway for ebeam 16 (FIG. 1) to pass from inlet 227 to outlet 229. Body 223 is provided by upper (upstream) member 300 and lower (downstream) member 302 that are joined at interface 304. Interface 304 provides clamping surfaces that clamp mirror 306 in place between member 300 and member 302. The interface is formed so that the mirror is held at a tilted angle relative to the central axis 211. The term "tilted" means that the mirror 306 is clamped so that its reflecting face(s) are non-orthogonal and non-parallel to central axis 211. Generally, as the mirror 306 is tilted relative to the central axis 211, one side of the mirror will have an acute angle alpha with respect to the axis 211. The angle alpha desirably is in a range from 10 degrees to 80 degrees, even 20 degrees to 70 degrees, or even 30 degrees to 60 degrees. In one embodiment, holding the mirror 306 at a tilted angle of 45 degrees would be suitable.

It can be seen that the mirror 306 is mounted at a tilted angle in the through aperture 312 of the central core and mirror assembly 226 that has a conical shape that progressively opens as the ebeam moves downstream through the assembly 226. At the same time, the assembly 226 is desirably formed from a polymer material that has ebeam absorbing characteristics. This helps to reduce stray radiation and x-ray production.

Mirror 306 advantageously is at least partially reflective to optical illumination (e.g., electromagnetic light includes one or more wavelength portions in a range from ultraviolet light (e.g., as low as about 200 nm) to infrared light (e.g., as high as about 2000 nm). More desirably, mirror 306 is at least partially reflective to visible light such as one or more wavelength bands in a range from 430 nm to 750 nm. An advantage of a mirror face that is partially reflective to such light is that it allows distance detection and illumination components to be housed outside of central core and mirror assembly 226 where these can laterally transmit light generally radially inward toward the central axis 211. Mirror 306 redirects the light downward along axis 211 to accomplish illumination and distance detection operations as described further below.

Because mirror 306 is clamped within central aperture 312 in the ebeam path, it is desirable that mirror 306 is at least partially transparent to the ebeam while still also being partially reflective with respect to the optical illumination. A mirror configuration will be deemed to be partially transparent to ebeam radiation if any portion of the electron beam incident on the upstream face of the mirror is able to reach the target site 12 (FIG. 1). Even though an ebeam can still be useful if the mirror 306 absorbs larger portions of the ebeam, it is desirable if the ebeam energy loss due to travel through the mirror 306 is as small as possible while still providing desirable reflective properties for incident light (e.g., light having a wavelength in one or more bands of the electromagnetic spectrum from 200 nm to 2000 nm). In many embodiments, it is desirable that the ebeam energy loss as a result of travel through the mirror 306 is less than 5%, desirably less than 2%, more desirably less than 1%, and even less than 0.5%.

Preferred embodiments of mirror 306 are in the form of thin polymer sheets with metallized coatings formed on one or both major faces. Illustrative polymer sheets may have a thickness in the range from 0.001 inches to 0.100 inches. Advantageously, such thin sheets have negligible impact on the ebeam energy while still being strong and durable and while providing excellent reflective properties. In contrast, thin metal sheets in this thickness range tend to be more fragile than might be desired, but still could be used. One suitable mirror embodiment is provided by a polyethylene terephthalate (PET) sheet having a thickness of 0.002 inches and bearing a sputtered aluminum layer on a surface to provide reflectivity.

In the practice of the present invention, one useful way to calculate the impact of a mirror upon ebeam energy is to use the following equation:

$$A = \left(\frac{D}{1.40}\right) \times \left(\frac{T}{1.38}\right) \times 99.8$$

wherein A is the percent of the ebeam absorbed by the mirror, D is the density of the sheet in g/ml at 25° C., and T is the sheet thickness in inches. Using the 0.002 inch PET sheet described above, its thickness is 0.002 inches×1.414=0.00283 inches as presented to the ebeam (the sheet is tilted at 45 degrees to the ebeam path), and its density is 1.39 g/ml. Therefore, A is 0.21% to show that such a thin, reflective mirror absorbs a negligible amount of the ebeam energy that pass through mirror 306.

Upper member 300 is secured to lower member 302 in any suitable fashion. According to one technique, using fasteners 316 is suitable. Complementary fastener holes 318 are provided in members 300 and 302 for this purpose. Lower member 302 includes optional window 314 through which optical signals may be projected into the central aperture 312 and redirected by mirror 306 toward the target site 12 (FIG. 1). Using a window 314 is one useful way to provide optical access to the mirror 306. Other strategies are available. For example, the mirror 306 could be mounted to an underside of the assembly 226 where the walls of the assembly 226 would not block optical access to the mirror 306. However, packaging the mirror 306 in the central aperture 312 using window 314 to provide access allows the overall height of the rotary coupling system 95 to be more compact.

FIGS. 5-7, 13-14, 29-30, 32-34, and 45 show the rotary base plate 240 in more detail. Rotary base plate includes upper rim 320 and lower rim 324. Top face 322 is at upper rim 320 and lower face 326 is at lower rim 324. Rotary base plate 240 has shoulder 328 and neck 330. Inner cylindrical wall 332 helps to define central aperture 334 having the common central axis 211 in the assembled coupling system 95. Rotary base plate 240 serves as a main support and mounting member for other components of the second sub-assembly 98.

FIGS. 5-7, 29-30, 32-33, 35, and 42-43 show the rotor 242 in more detail. Rotor 242 includes base 340. Base 340 attaches rotor 242 to the rotary base plate 240. At rotor 242, neck 344 projects upward from base 340. Rotor ring 262 is mounted onto rotor 242 around neck 344. A ring 348 of detent features 349 is formed in top surface 346. Ring 348 is part of rotary indexing and rotary locking systems described further below. Rotor 242 includes recess features to house the outer race 252 of ring bearing 200 as well as the outer race clamp 258. Rotor 242 includes central aperture 350 having the common central axis 211 through which the ebeam 16 (FIG. 1) passes.

FIGS. 5-7, 13-14, 29-30, 32-34, and 45 show the mounting plate 244 in more detail. Mounting plate 244 includes body 360 extending from top rim 362 to bottom rim 366. Top surface 364 is at top rim 362. Top surface 364 is attached to the lower face 326 of the rotary base plate 240. Interior, cylindrical wall 368 defines central aperture 370 having the common central axis 211 through which the ebeam 16 (FIG. 1) travels. The lower face 365 of mounting plate 244 includes rails 372 and slot features (not shown) similar to those on shield 88 in order to couple mounting plate 244 to the head 126 of applicator 86.

FIGS. 30-31, 33-34, and 41 show the rotary indexing system in more detail formed from plunger assembly 380 mounted on the upper sub-assembly 96 and ring 348 and detent features 349 formed on the rotor 242 of lower sub-assembly 98. Plunger assembly 380 includes a main support plate 382 that is attached to main body 220. Support plate 382 includes a slot 384 in which linear rail 390 is mounted. A carriage 392 rides back and forth along linear rail 390. Mounting holes are used to attach plate 382 to main body 220. Mounting bosses 388 are used to attach guiding frame 394 to the plate 382.

Guiding frame 394 has legs 396 connected at one end by crosspiece 398. Open slot 400 is formed between legs 396 underneath crosspiece 398. Bearing support 402 is attached to sliding carriage 392, and thus can move linearly up and down with the carriage 392. Roller bearing 404 is mounted to the lower end of the bearing support 402. Roller bearing 404 rides in the detent features 349 of detent ring 348. Head 406 of the bearing support 402 fits in the slot 400 to help guide the roller bearing 404 up and down as the bearing 404 rides around ring 348. A spring 403 pushes downward against pocket 408 of bearing support 402 as well as upward against the crosspiece 398 in order to bias roller bearing 404 to be pushed down against the ring 348 while still allowing bearing 404 to move up and down to accommodate the ups and downs of the detent features 349.

In use, the rotary indexing system helps the upper and lower sub-assemblies 96 and 98 to rotate relative to each other in indexed increments corresponding to the number of detent features 349 incorporated into ring 348. Generally, a greater number of detent features 349 provides a greater number of indexed rotational positions as compared to using a lesser number of detent features 349. In one embodiment, using a ring 348 including 180 detent features 349 allowed rotation in two-degree increments.

FIGS. 29, 31, 35, 39, and 42-44 show the rotary locking and release mechanism 236 in more detail. Mechanism 236 includes button actuated locking device 432 mounted onto main body 220 of upper sub-assembly 96 and the ring 348 and detent features 349 on the lower sub-assembly 98. The ring 348 and detent features 349 thus play a role both for indexed rotation as well as for rotational locking functionality.

Device 432 includes a housing 434. Slideable locking teeth 436 project from the underside of the housing 434 that faces the ring 348. Housing 434 is deployed so that the slideable locking teeth 436 engage or disengage from ring 348 on demand. The teeth 436 have a sliding range of motion in which the teeth 436 engage with detent features 349 of ring 348. In this configuration, the engaged teeth 436 prevent relative rotation between the sub-assemblies 96 and 98. In effect, rotation of the applicator 86 and shield 88 are locked in this configuration. The slideable locking teeth 436 have a further range of motion in which the teeth 436 can slide radially inward to disengage from the detent features 349 of ring 348. In this configuration, the sub-assemblies 96 and 98 are unlocked and able to rotate relative to each other. In effect, the applicator 86 and shield 88 can rotate in this configuration.

The slideable locking teeth 436 are actuated by pressing or releasing button 438 that is coupled to the locking teeth 436. In an un-pressed, released configuration, the teeth 436 are biased to be engaged with the detent features 349 to lock the rotation. In effect, a locked rotational configuration is the default. A spring or other suitable device can be used to provide the bias to keep the teeth 436 engaged with the detent features 349 when the button 438 is not pressed.

Pushing the button 438 also pushes the teeth 436 radially inward at the same time. This causes the bias against the teeth 436 to be overcome. The teeth 436 slide radially inward to become disengaged from the detent features. This unlocks the rotation, allowing the applicator 86 and shield 88 to be rotated about axis 211. The inward movement of teeth 436 to unlock rotation is shown by arrow 442. Releasing the button 438 allows the bias to push the button 438 outward and the teeth 436 radially outward back into engagement with the detent features 349. The outward move of the teeth 436 back to a locking position is shown by arrow 440. The positioning of teeth 436 is calibrated so that the teeth 436 engage the detent features 349 when the relative rotation of the sub-assemblies 96 and 98 is in an indexed rotational configuration.

FIGS. 5-7, 10, 29-31, 33, 36-37, and 39-40 show the optical illumination system in more detail. The optical illumination system includes at least two illumination functions. First, an illumination source is used to create illumination that is redirected along the ebeam pathway 90 (FIG. 2) in order to illuminate the target site 12 to make it more easily viewed. Second, an illumination source is used to generate a reference mark, such as cross hairs, that is redirected along the ebeam pathway 90 (FIG. 2) along central axis 211 in order to precisely show where the ebeam 16 is aimed. The reference mark is thus projected onto the patient, and a deviation between the projected reference mark and the target site 12 can be compared. This allows the unit 26 to be precisely adjusted to overcome the deviation so that the reference mark is aimed properly at the target site 12.

A support arm 450 serves as a base for the components. Support arm 450 includes mounting bosses 452 for attaching to the main body 220. Laser mounts 456 help to mount laser 454 to the support arm 450. Laser 454 is configured to emit a laser output in the form of a reference mark that can be projected to the target site 12 (FIG. 1). A laser-aiming fixture 458 allows the laser output to be calibrated so that the reference mark is projected to the target site along the center axis 211. An illumination source, such as an LED illumination source 460, generates illumination that also is projected to the target site 12 along the center axis 211. Projecting these along the center axis 211 helps to ensure that projection accuracy is maintained through a suitable range of treatment distances between the end of the shield 88 and the target site 12.

The laser 454 and the illumination source 460 generate optical output from different directions. However, it is helpful to align these so that common components can be used to project the light outputs down to the target site 12. Desirably, the optical signals from the laser 454 and illumination source 460 are redirected accurately down the central axis 211. The combination of the optical signals desirably is accomplished so that the reference marks remain visually observable at the target site 12 rather than being substantially homogenized into a composite illumination in which the reference marks are optically washed out. To this end, optical manifold 476 is provided to receive the illumination and laser reference marks from different directions and then to output the two types of illumination in a common direction.

In one mode of practice, a conventional beam splitter is used in reverse to function as a beam combiner. A beam splitter includes a partially reflective/partially light transmissive element deployed at a 45 degree angle. From one direction, and incident signal can pass straight through the element with only part of that beam being lost to reflection. At the same time, a second signal can enter at 90 degrees from a second direction. Since the surface is partially reflective, a portion of this second signal will be redirected at 90 degrees as an output. The result is that the input signals arrive at the element from two directions but are emitted in the same direction.

For example, consider a beam splitter having a 70R/30T specification. This means that 70% of incident light is transmitted while 30% is reflected. In a desired mode of practice, the LED illumination is aimed so that it enters and leaves the element on a liner path. This means that 70% of the illumination passes through to be projected to the target site 12. In the meantime, the laser signal carrying the reference mark enters the element at a right angle relative to the output direction. This means that 30% of the laser signal is reflected to be projected to the target site 12. The other 70% of the laser signal passes through the element and is blocked with a suitable component such as a neutral density optical filter. This strategy is desired because the laser signal as emitted from the laser is concentrated enough to scatter and create artifacts that could show up at the target site. The strategy described here reduces these scatter and artifact effects.

The optical illumination system also includes an auxiliary mirror 478 on the support arm 450. This auxiliary mirror 478 helps to guide the combined optical signals radially inward with respect to the central core and mirror assembly 226 through the window 314 and toward the mirror 306 so that the light signals can be projected by the mirror 306 downward along the central axis 211 to the treatment site 12. Auxiliary mirror helps to make the overall deployment of the systems 222 and 224 more compact so that the optical signals developed by these systems can be effectively transmitted through window 314 to the mirror 306 and so that the image capturing sensor 474 can appropriately observe the mirror 306 through the window 314.

Figure 10:
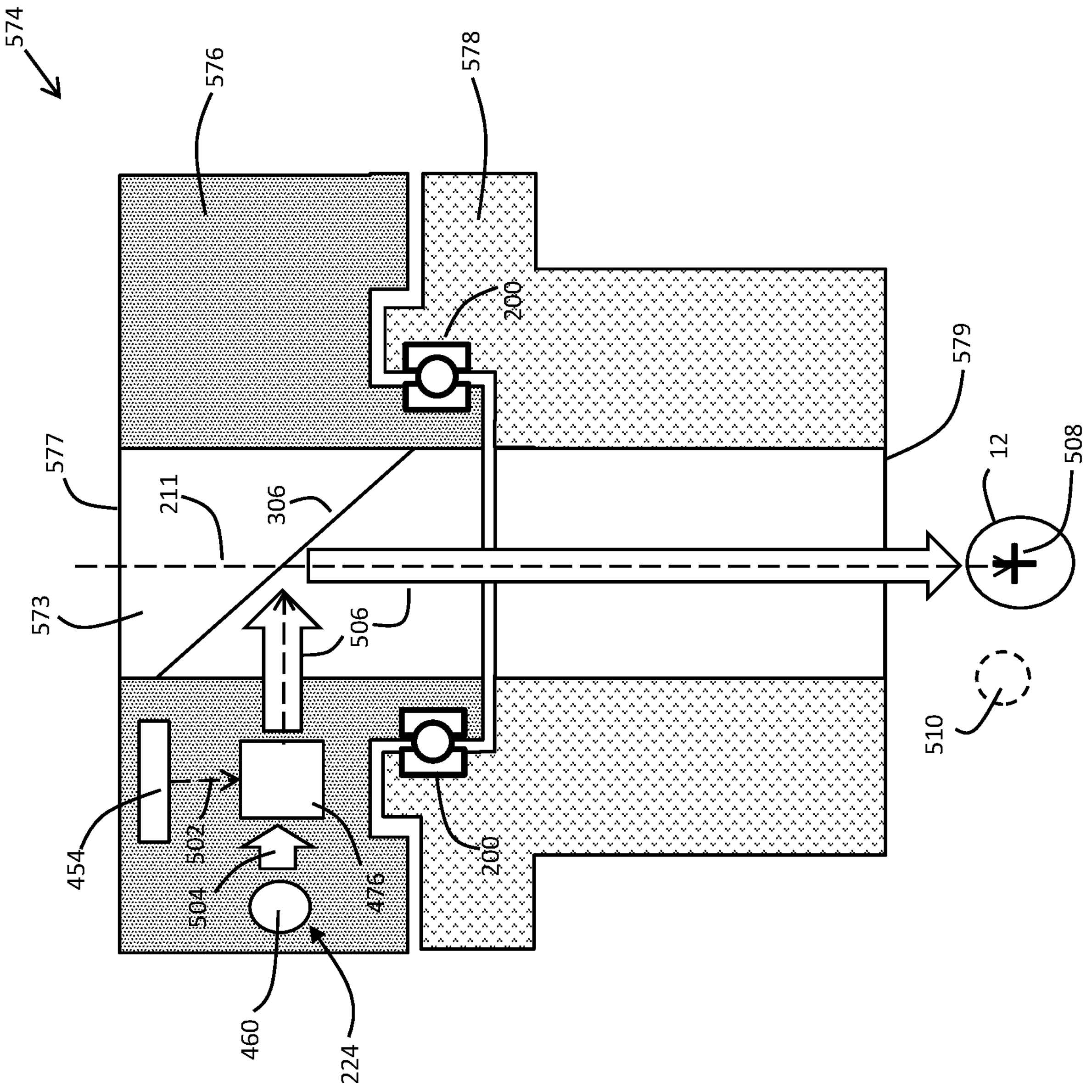
FIG. 10 schematically shows how components to automatically illuminate and project reference marks onto a target site can be incorporated into the assembled components of FIG. 8.
Figure 11:
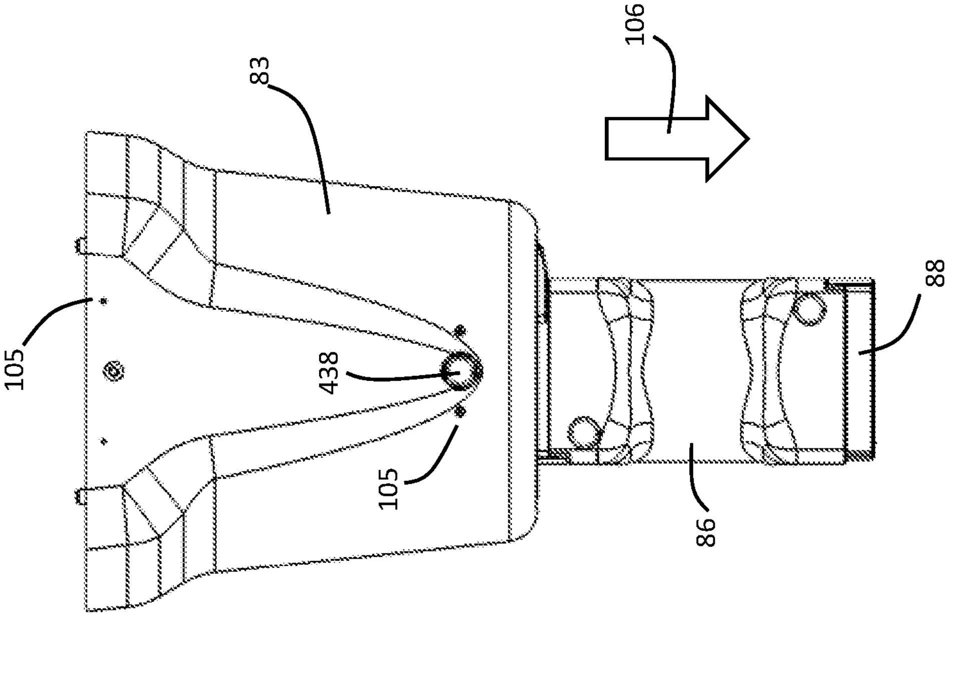
FIG. 11 shows a side view of the assembled components of FIG. 8 in more detail.

FIGS. 10 and 36-37 schematically how the optical illumination system works. Laser 454 outputs an optical signal 502 that provides a reference mark such as an optical crosshair. One convenient output generates the reference mark from green laser light. An advantage of doing this is that green laser light is easily seen on a variety of different skin tones. Other colors of laser light may be difficult to see for some skin tones. The optical signal 502 of laser 454 is aimed at the optical manifold 476. The optical manifold 476 redirects and emits a portion of the laser optical signal 502 in an output direction that is at 90 degrees relative to the input direction. At the same time, illumination source 460 outputs an illumination signal 504 toward the optical manifold 476. The optical manifold 476 allows a portion of the illumination signal 504 to be emitted in the same output direction as the laser optical signal 502. For purposes of illustration, the two signals transmitted by optical manifold 476 are shown as the optical signal 506. FIG. 10 schematically shows how optical signal 506 is emitted by optical manifold 476 toward the mirror 306. In the more detailed Figures such as FIG. 40, it can be seen that an auxiliary mirror 478 also is used to help direct optical signal 506 to the mirror 306. Mirror 306, being partially reflective to optical illumination, redirects at least a portion of the optical signal 506 along the central axis 211 toward the target site. The result is that an optical reference mark shown as crosshair 508 is projected onto the target site 12 to accurately show where the ebeam 16 is aimed. At the same time, target site 12 is bathed in illumination from the optical signal 506. If the crosshair 508 is not projected onto the target site 12, such as if it shows up as cross hair 510 away from the target site 12, this indicates that ebeam 16 is not properly aimed at target site 12. The visual feedback allows the aim to be easily corrected until the crosshair 508 is in the desired location.

FIGS. 5-7, 9, 10, 29-31, 33, 36-37, and 39-40 show details of the automated detection system. Mounting plate 468 serves as a base for distance sensor 470. Distance sensor 470 is mounted to plate 468. Plate 468 in turn is mounted to main body 220. Distance sensor 470 incorporates a laser source 472 that outputs a laser signal. Distance sensor 470 also incorporates an image capture sensor 474, such as a CMOS sensor.

Figure 9:
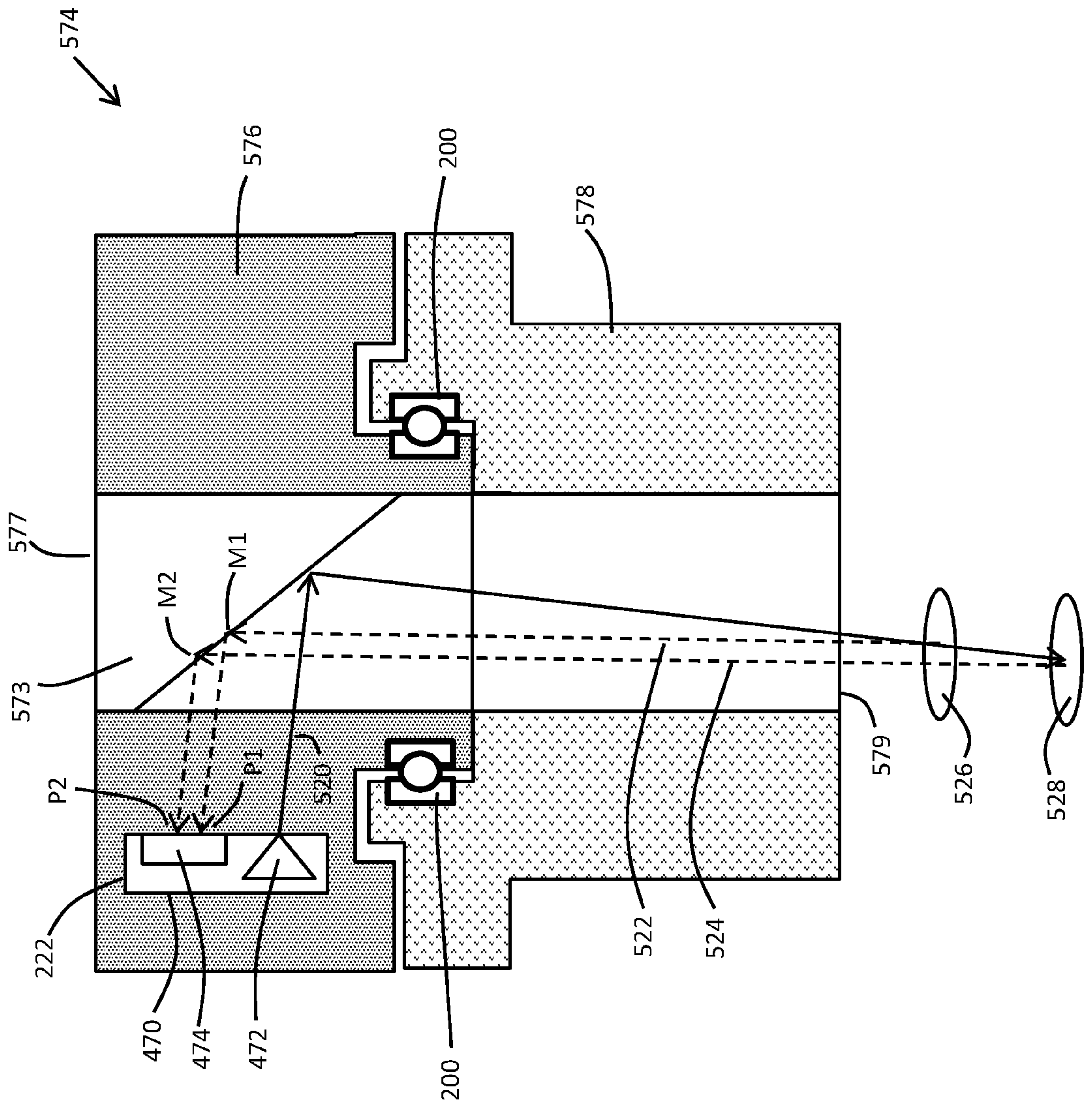
FIG. 9 schematically shows how components to automatically measure distance can be incorporated into the assembled components of FIG. 8.

FIGS. 9, and 36-37 schematically show how the automated distance detection system works. The laser emits an output laser signal 520 through window 314 to mirror 306. Mirror 306 reflects the signal 520 downward to the patient surface. At the surface, the laser signal 520 is reflected back up to mirror 306 along a path such as paths 522 or 524. The path of the reflected beam, whether it is path 522, path 524, or another path is a strong function of the distance to the surface generating the reflected beam. For example, path 522 results if the beam 520 is incident upon a relatively close surface 526. In contrast, path 524 results if the beam 520 is incident upon a relative more distant surface 528. In each case, the path 522 or 524 is reflected back onto the mirror 306 at a point M1 or M2 whose location is a function of and is correlated to the distance to the surface 522 or 524, as the case may be. The imaging sensor 474 observes the mirror 306 and captures images of the points M1 or M2, as the case may be, on the image plane as points P1 or P2. The location of P1 or P2 on the image plane differs as a function of distance and is highly correlated to distance. Accordingly, the detection system can use the captured image information to determine the location of the reflected beam in the captured image information and use an appropriate correlation to convert the location into a distance. The distance detection is quite accurate, wherein resultant distance determinations would be accurate to within +/−1 mm or even more accurate such as to +/−0.5 mm or better.

The distance may be computed as between the surface being irradiated and a suitable distance reference on unit 26. One suitable distance reference is to compute the detected distance with respect to the outlet of the scattering foil system 82 (FIG. 2) incorporated into collimator 80. Other locations on unit 26 also may be used as a distance reference if desired. For example, the outlet of window 78 (FIG. 2) may serve as the distance reference. Other alternatives include the outlet of the applicator 86 or shield 88, the outlet of the mounting plate 244, or the like.

FIG. 46 shows an alternative mode of practicing the invention. FIG. 46 is identical to FIG. 7, except that only a single field defining member in the form of shield 88 is attached to the sub-assembly 98 of rotary coupling system 95. Applicator 86 (FIG. 7) is not used. As another difference, the mounting plate 244 is lengthened to help shape the electron beam in the absence of applicator 86.

FIG. 47 shows another mode of practicing the invention. FIG. 47 is identical to FIG. 7 except that only a single field defining member in the form of applicator 88 is attached to the sub-assembly 98 of rotary coupling system 95. Shield 88 (FIG. 7) is not used.

Note that moving the equipment into position with respect to a patient in order to carry out a treatment is referred to in the industry as docking. In uses of the ebeam radiation systems described herein, at least a portion of the system and/or the patient will be moved relative to each other during docking, treatment, and/or undocking such as to accurately position the equipment for irradiation of the target site 12 (see, e.g., FIG. 1). In one example, a patient is placed in a fixed or stationary location, such as on a treatment bed or chair, and then the system 10 is moved toward the patient to administer treatment. In another example, the system 10 is in a relatively fixed position and the patient is moved toward the system to administer treatment. In yet another example, both the patient and the system 10 are moved relative to each other to achieve the desired positioning to administer treatment. In one example, a patient is supported on a suitable patient support structure, such as on a treatment bed or chair, and then the system 10 is moved toward the patient to dock the equipment in the desired position and to administer treatment. The patient supporting structure also may be moveable in order to help achieve and maintain the desired docking position. Hard docking occurs when the equipment is in physical contact with the target site. Soft docking occurs when the equipment and the target site are spaced apart.

Figure 48:
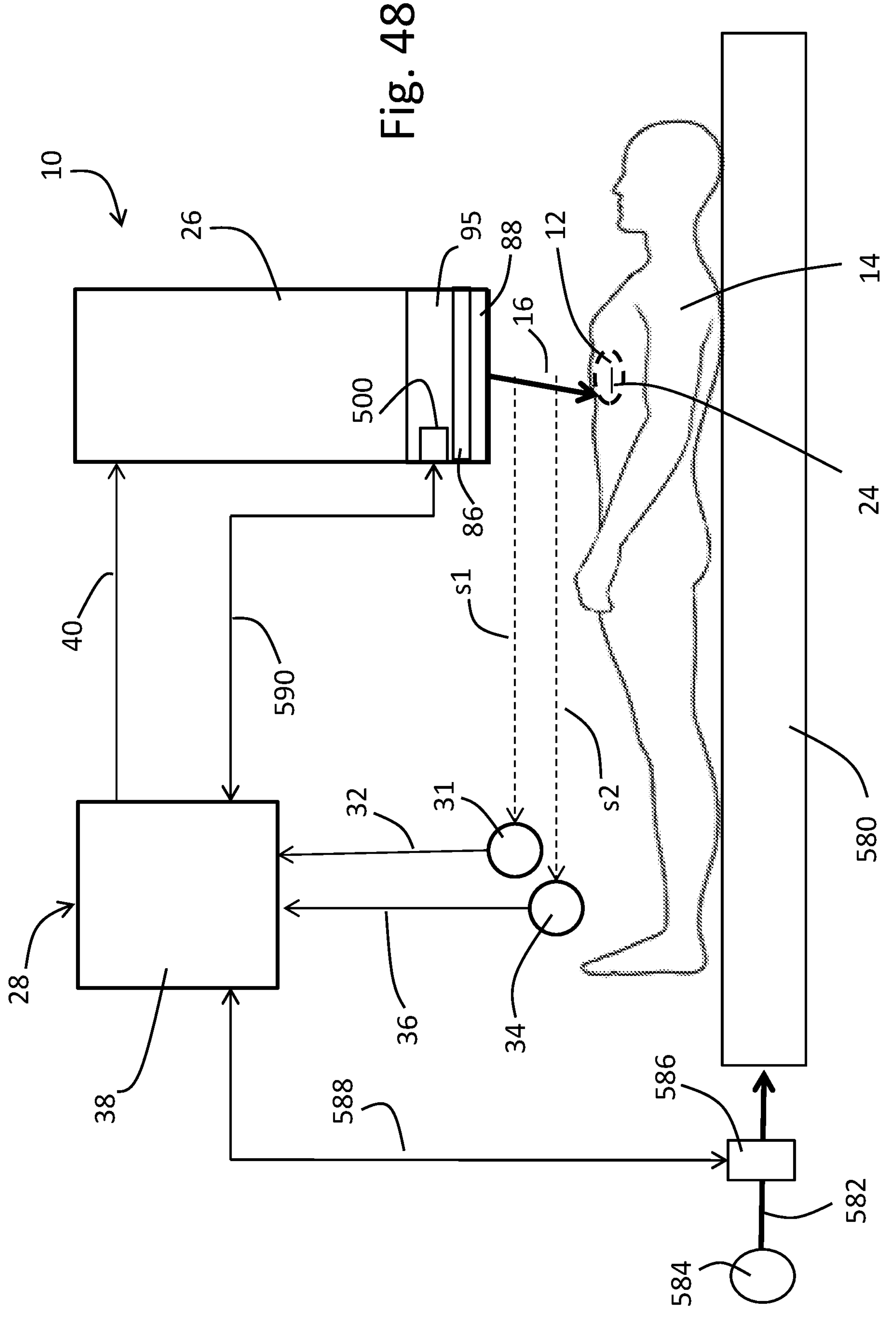
FIG. 48 schematically shows the electron beam radiation system of FIG. 1 being modified to incorporate additional features to provide collision detection functionality.
Figure 49:
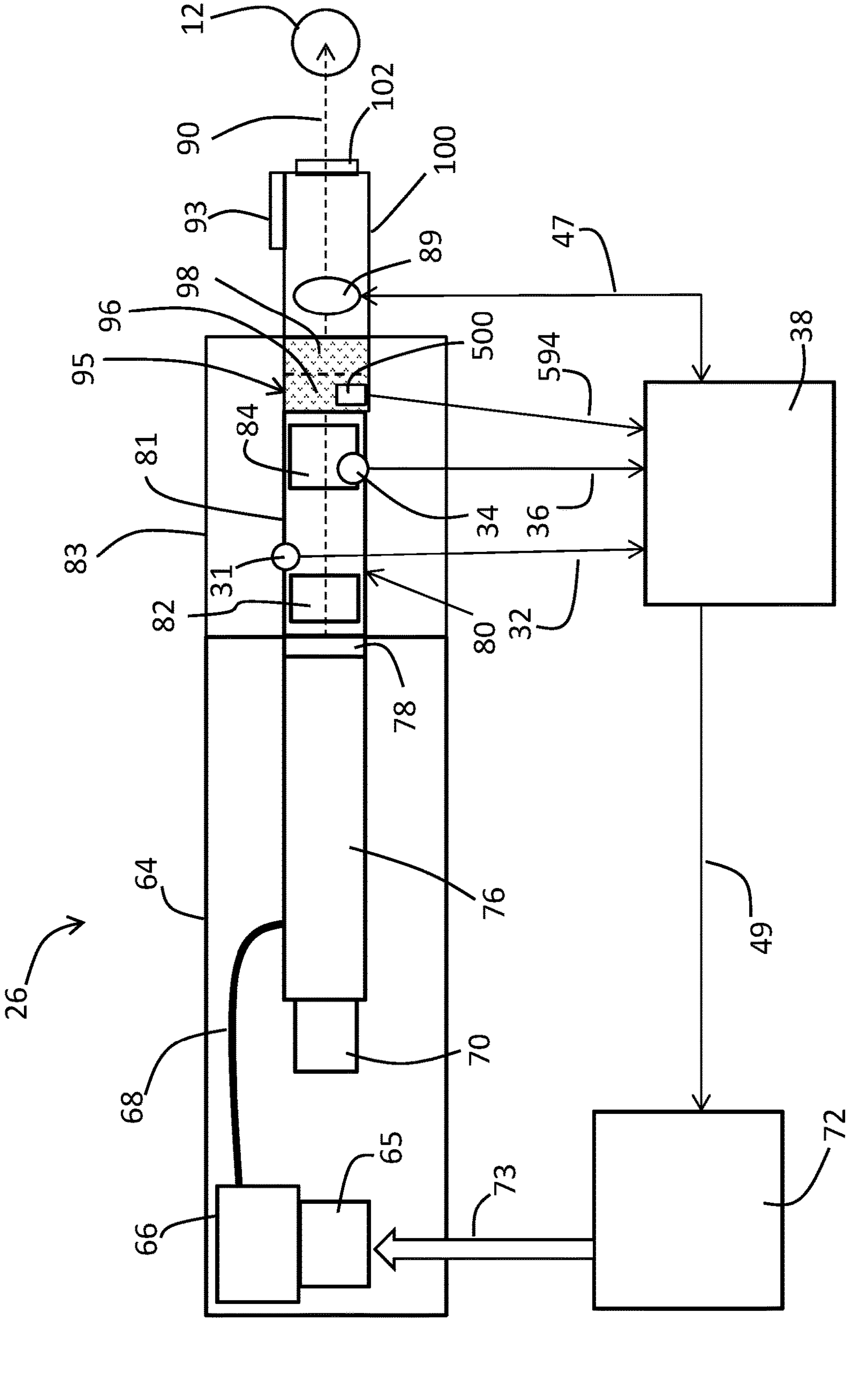
FIG. 49 schematically shows how the electron beam generation unit used in the electron beam radiation system of FIGS. 1 and 2 is modified to include collision detection functionality.

The fact that the equipment, patient, and/or patient support structure may move or be moved during docking, during the course of a treatment, or after a treatment so that the patient can leave means there are risks of collision between the equipment and other elements of the operating arena such as the patient, treatment personnel, the patient support structure, other equipment, and the like. FIGS. 48 and 49 schematically show how the system 10 of FIGS. 1 and 2 may be modified in order to allow automatic detection of collisions. Automatic or manual follow up action can then be taken responsive to detection of a collision event or to circumstances indicating that the collision event has passed.

System 10 of FIGS. 48 and 49 are identical to system 10 of FIGS. 1 and 2 except for including additional features to allow automatic collision detection and follow up. Features of FIGS. 48 and 49 that are the same as those in FIG. 1 are identified by the same reference number. FIG. 48 differs from FIG. 1 in a first respect by showing the patient 14 supported on patient supporting structure 580. Patient supporting structure 580 is shown as a table or bed, but in practice the supporting structure 580 can be another type supporting structures such as a chair, recliner, or the like. Patient support structure 580 is moveable to help properly position the supported patient 14 for the desired treatment. The patient support structure 580 can be moved to a desired position prior to docking, during docking, during the treatment to help accommodate patient movement, and/or after the treatment to facilitate undocking and the patient leaving the support structure 580. The support structure 580 may be capable of various types of movement including ranges of pavement on one or more of the x, y, z, pitch, roll, or yaw axes.

A power feed line 582 supplies electrical power to the patient support structure 580 from a suitable power source 584. The power source 584 may be a utility or a local source of power such as a battery pack, generator, or the like. Power controller 586 allows the power feed to the support structure 580 to be powered on, powered off, or modulated. In some instances, for example, it may be desirable to cut the power to the patient support structure 580 in the event a collision is detected. Power controller 586 is coupled to the controller 38 by communication pathway 588 so that signals may be transferred between power controller 586 and controller 38 as desired.

As an additional component used to help provide collision detection functionality, a sensor 500 is coupled to the electron beam generation unit 26. For purposes of illustration, the sensor 500 is integrated onto the coupling system 95. This location is advantageous, as many times it is a component of the coupling system 95 or accessories attached to this, such as the applicator 88, that are involved in a collision. Sensor 500 is configured to include a capability to detect force and/or torque encountered by the electron beam generator unit 26. Sensor 500 is coupled to controller 38 by communication path 590. This allows the sensor readings of sensor 500 to be transmitted to controller 38 over time. Path 590 also allows controller 38 to transmit control signals to sensor 500 as well.

In some embodiments, sensor 500 detects readings at a suitable sampling rate and transmits these in real time to controller 38. In controller 38, the readings may be stored in a memory. A hardware processor in controller 38 is configured to execute steps in one or more procedures according to instructions that use the readings to evaluate whether a collision is detected or whether the system is in a normal state. In some embodiments, sensor 500 detects torque readings. In other embodiments, sensor 500 detects force readings. In some embodiments, both torque and force readings are sensed. Detecting both force and torque readings is advantageous as there could be circumstances in which a collision might only cause one of the rate of change profiles of these to exceed a specification in a manner to indicate a collision. Hence, monitoring both kinds of readings helps to minimize the risk that a collision is missed.

The rate of change of torque or force generally is based on any suitable evaluation indicative of how one or more most current values of sensed torque or force are changing relative to one or more earlier values of force or torque. Because torque and force readings typically are associated with some degree of noise causing the sensed values to fluctuate up and down (see, e.g., the values of torque in the time period from t0 to t1 in FIG. 58*a*), it is desirable to smooth the values used to determine the rate of change values. In other words, it is desirable to obtain rate of change values indicative of the first derivative of the data over a suitable time period. For example, a ratio or other comparison of a rolling average of 3 or more values the previous average of 3 or more values may be used to determine the rate of change at desired time intervals. In other instances, a moving average of 2 or more values may be determined and then the slope of 2 or more of these values may be calculated to provide the rate of change at desired intervals. As still another technique, using the Savitzky-Golay filter or similar filter can provide smoothed data for purposes of providing information indicative of the average first derivative over a suitable time period.

Advantageously, system 10 of FIGS. 48 and 49 use information indicative of the rate of change of the sensed torque and/or force readings to help evaluate collision status. A sudden change in magnitude of the rate of change, which can be an increase or a decrease, in the rate of change of one or both of these readings indicates a collision occurred. It has been found that using the rate of change of the force and/or torque readings provides much more sensitive, accurate, reliable, and/or rapid detection of collisions as compared to merely using force or torque readings alone without a time component that evaluates how the sensed property or properties change with time.

As between torque and force, information indicative of the rate of change of torque readings are more sensitive to collision status under many circumstances. The ability to use the rate of change of torque readings to detect collision status is further enhanced by an off-center mounting of the sensor 500 and its distance from the tip of the applicator as described below. Accordingly, in a preferred aspect, at least information indicative of the rate of change of torque readings is used to evaluation collision status. However, there are some collisions in which the rate of change of force is more sensitive to collision status than the rate of change of torque. For example, the rate of change of force is more sensitive to collisions that are substantially coincident with the main axis of the sensor 500. Accordingly, in another preferred aspect information indicative of the rates of change of both torque and force readings are used to evaluate collision status.

Advantageously, principles of the present invention allow the rates of change associated with readings of the force/torque sensor to be used in order to detect the collision status of system 10, such as detecting when a collision occurs between the unit 26 and the surface of a patient or some other surface as well as detecting when a collision event is over as well as detecting so-called false collisions (explained below). A collision event may occur at any time during docking, treatment, or post treatment movements. When a collision is detected, follow up action may be automatically implemented and/or manual follow up by an operator or the like may occur. For example, if a collision is detected, an alarm may be triggered. In parallel, controller 38 may send out control signals that at least temporarily stop the relative motion between the unit 26 and the patient 12. The stoppage may involve stopping movement of the unit 26 and/or patient support structure 580, for example. Such a control signal to stop movement of support structure 580 may be transmitted along pathway 586 to the power controller 584. Such a signal may cause power controller 584 to cut off the power supply to the support structure 580 (as illustrated), or such a signal may be sent to controllers in the support structure 580 to disable movement until the collision event is cleared.

Figure 50:
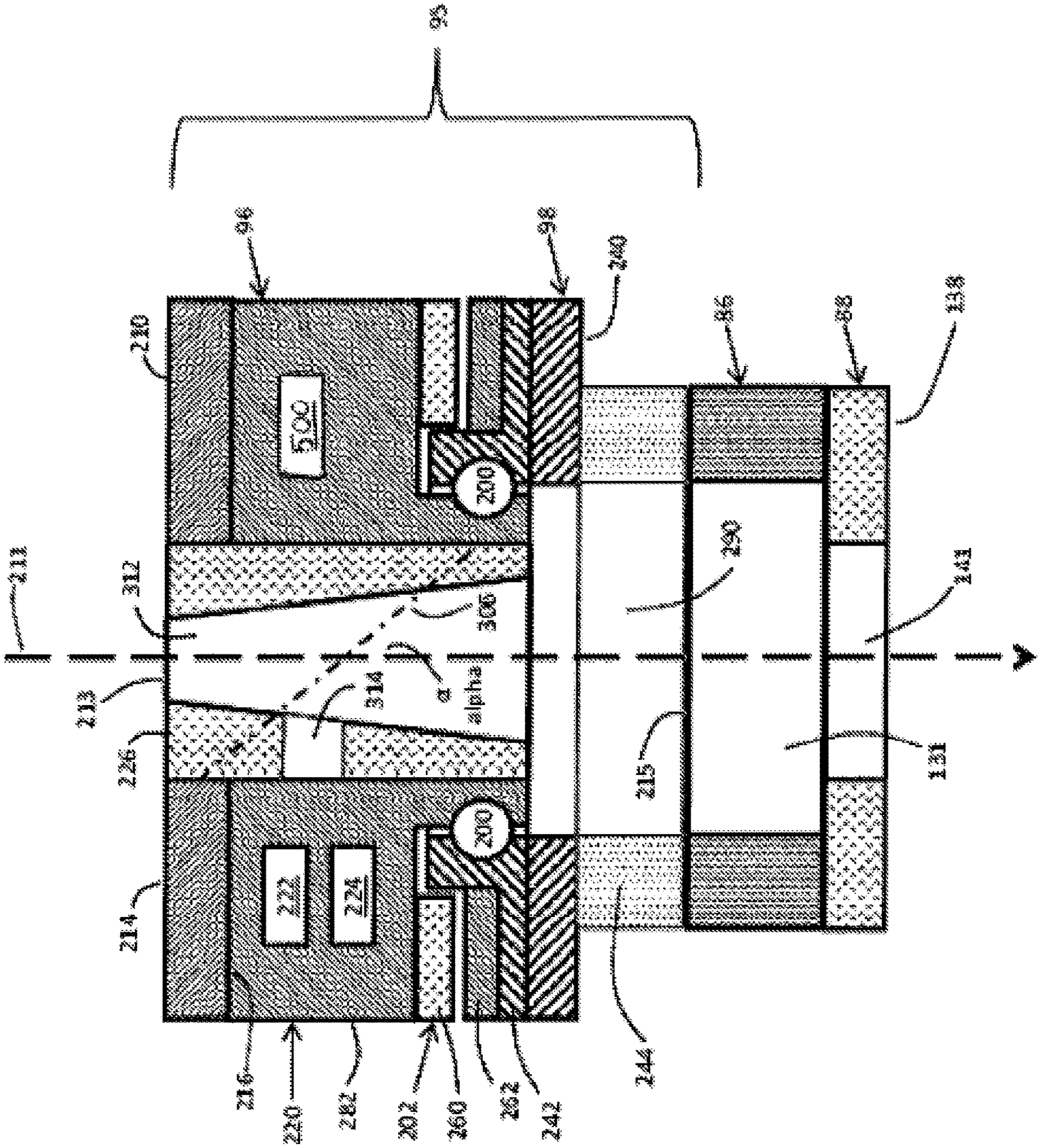
FIG. 50 schematically shows a side cross-section view of the rotary coupling system of FIG. 2 in alignment with field defining members in the form of an applicator and a shield, and including a force/torque sensor.

FIGS. 50 to 56 show how sensor 500 is incorporated into coupling system 95 in more detail and how coupling system 95 is modified to integrate sensor 500. FIG. 50 schematically illustrates an exemplary embodiment of the rotary coupling system 95 similar to that illustrated in FIG. 7 that incorporates sensor 500. In addition to the distance detection system 222 and optical illumination system 224 that are integrated in the main body 220, as described above, main body 220 also incorporates at least one sensor 500 to sense force and/or torque. Even though sensor 500 may sense one or both of force and/or torque, sensor 500 may be referred to herein as a force/torque sensor 500 for simplicity.

Figure 51:
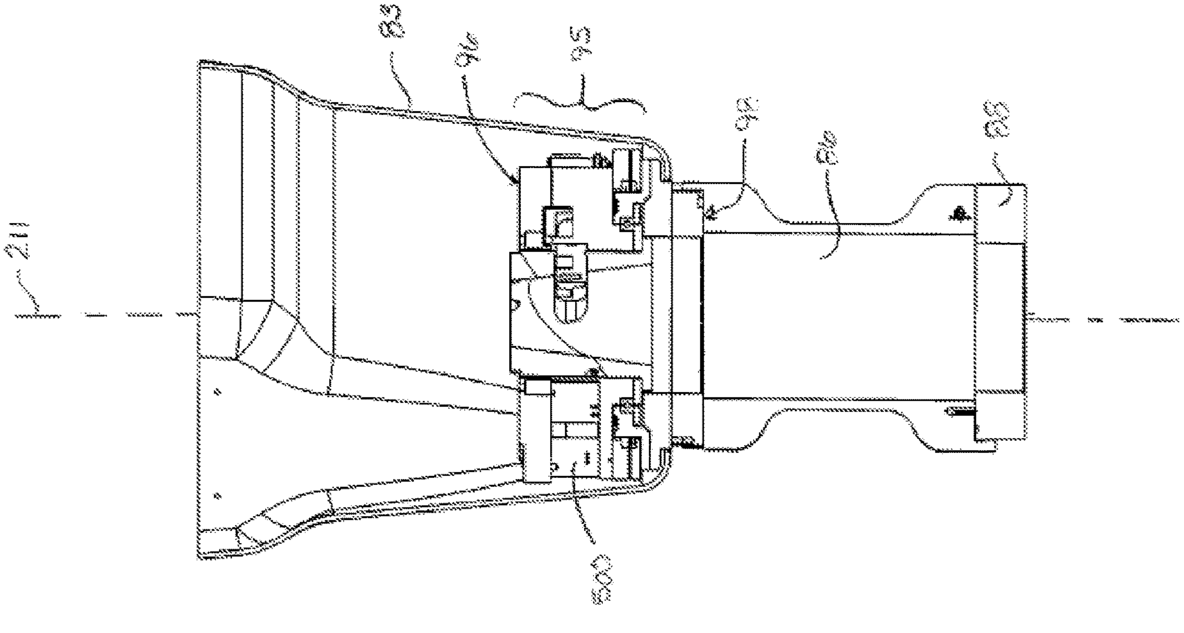
FIG. 51 is a further side view of the components of FIG. 48 showing the applicator and shield (attached to the outlet of the applicator) mounted to the rotary coupling system that includes a force/torque sensor and a housing surrounding the rotary coupling system.
Figure 52:
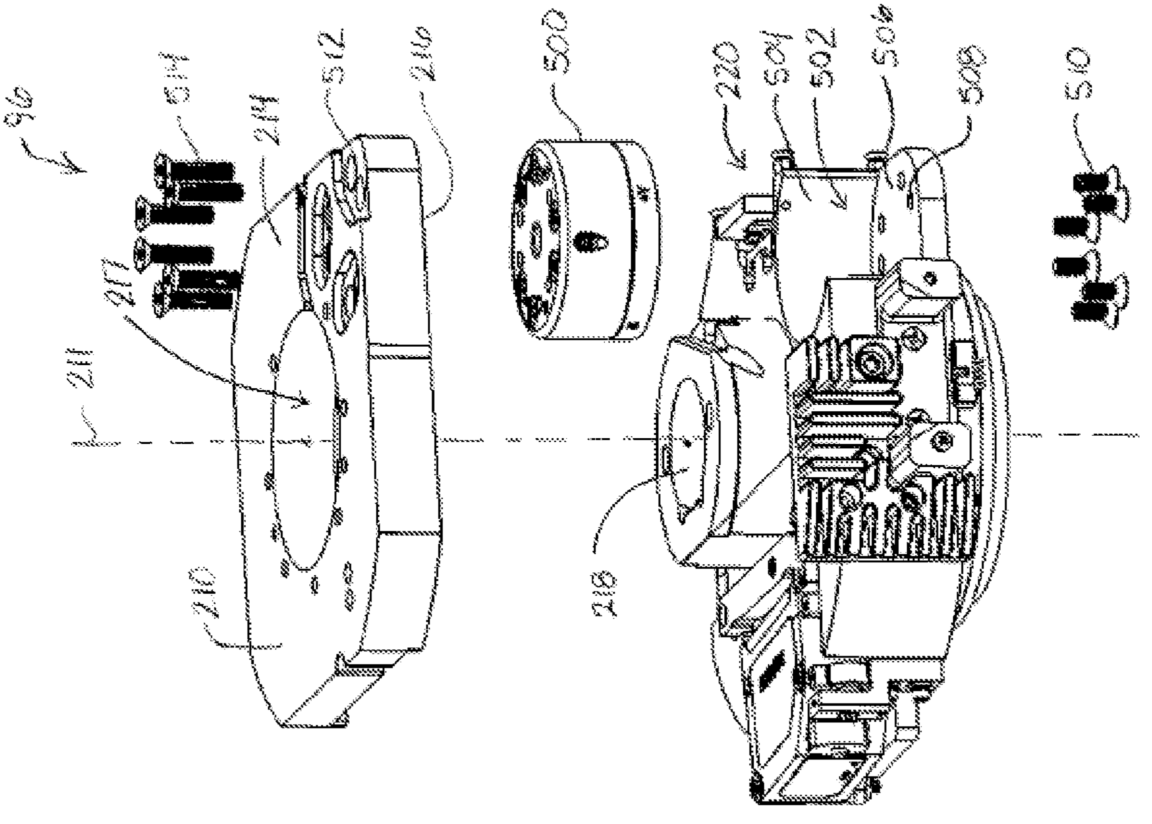
FIG. 52 is an exploded perspective view of the rotary coupling system of FIG. 49, including a force/torque sensor.
Figure 53:
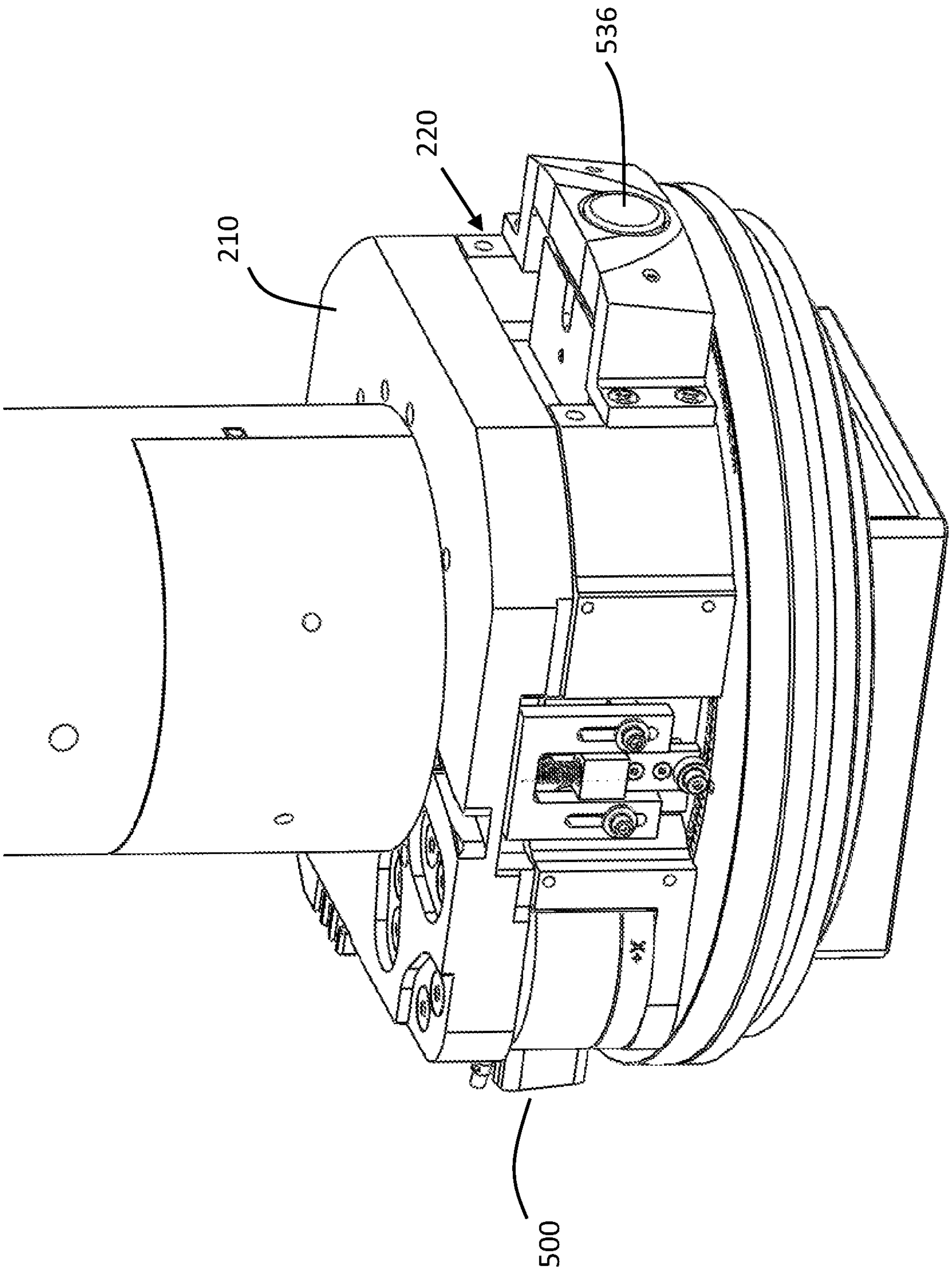
FIG. 53 is a side perspective view of the rotary coupling system of FIGS. 49 and 50, and including a rotary lock button assembly including a switch.
Figure 54:
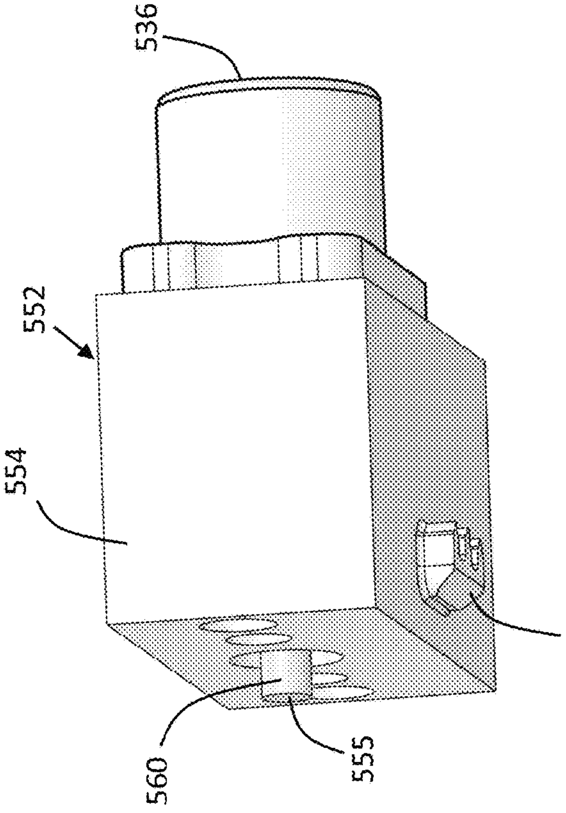
FIG. 54 is a bottom perspective view of the rotary lock button assembly of FIG. 51.
Figure 55:
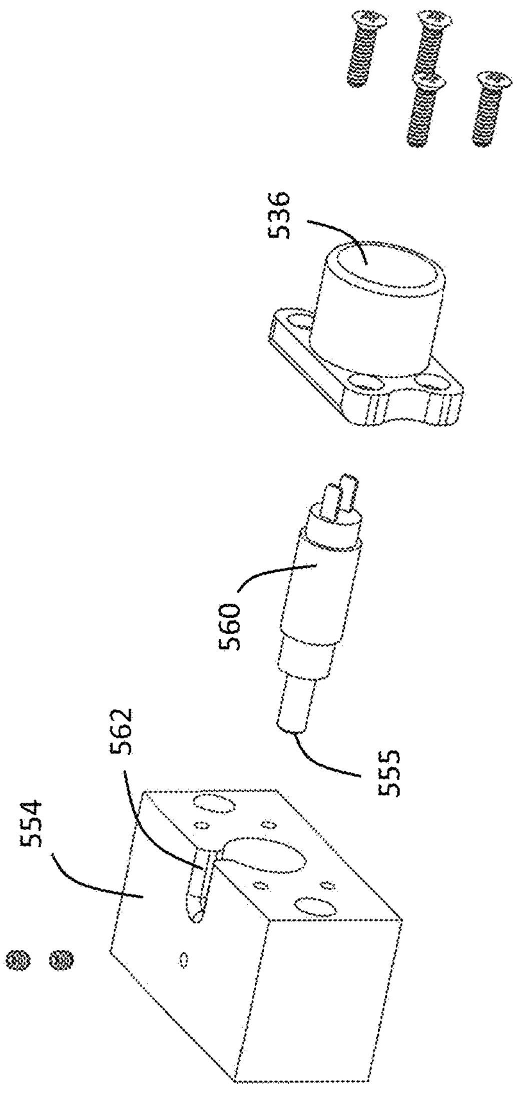
FIG. 55 is an exploded perspective view of the rotary lock button assembly of FIGS. 51 and 52.
Figure 56:
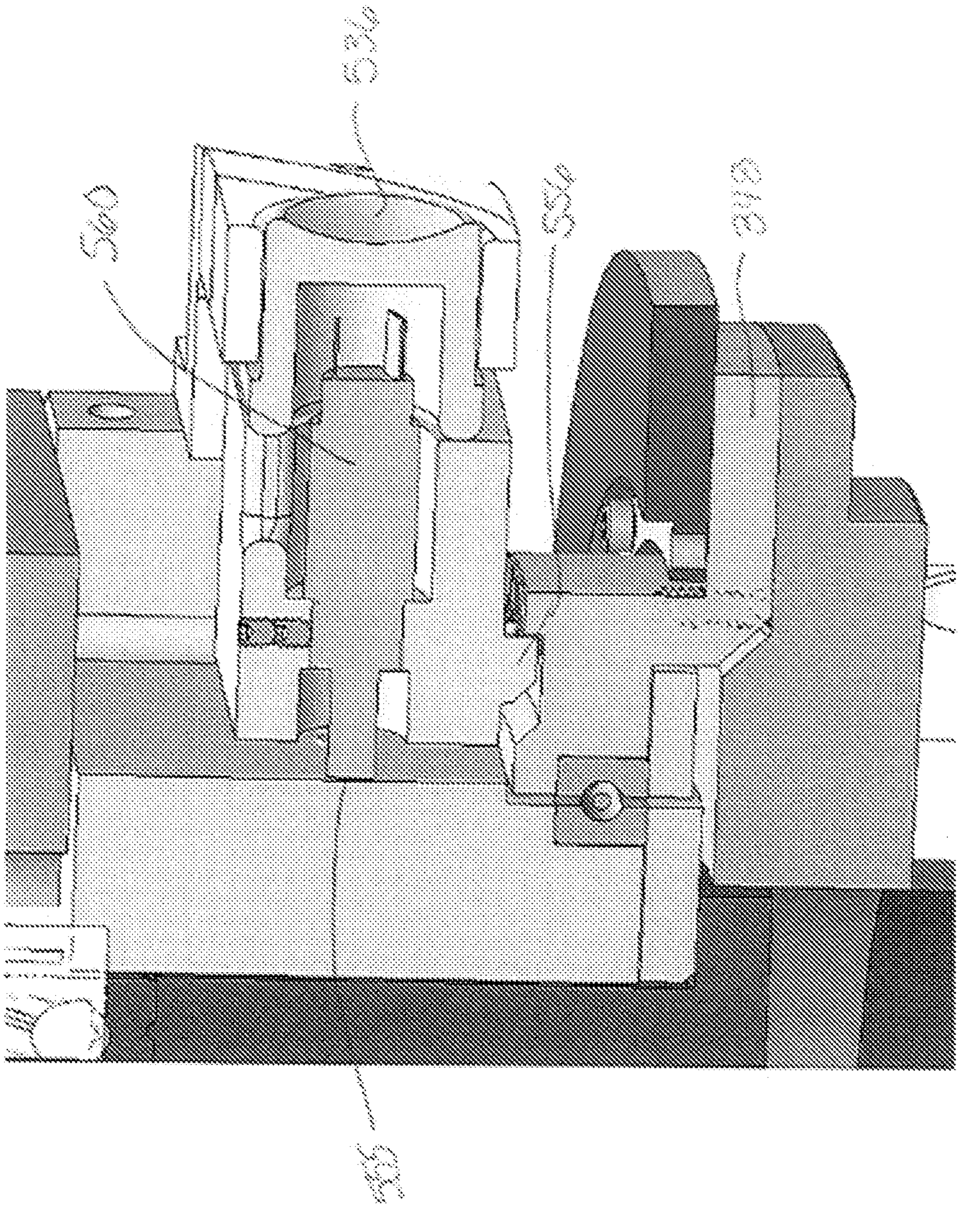
FIG. 56 is a cross-sectional front view of a portion of the rotary coupling system of FIG. 50, including a rotary locking button assembly with a switch.

FIGS. 51-53 illustrate coupling system 95 and its main components in more detail. Coupling system 95 generally includes a first, upstream sub-assembly 96 that is rotatably coupled to a second, downstream sub-assembly 98, wherein relative rotation between sub-assembly 96 and sub-assembly 98 can be automatically monitored and measured during use of the associated electron beam radiation system. Automated functionality (e.g., functionality described above) for measuring distance to the target site 12 (FIG. 1) is incorporated into the system 95.

The system of FIG. 51 also illustrates a housing 83 that is mounted to the coupling system 95, which can be mounted or removed, as desired. Housing 83 is mounted over the coupling system 95 using any of a wide variety of fasteners. The applicator 86 and shield 88 are accessible below the housing 83.

Force/torque sensor 500 is incorporated into the structure of the main body 220. In particular, force/torque sensor 500 is incorporated into the sub-assembly 96 of rotary coupling system 95. Sub-assembly 96 includes a recessed area or pocket 502 in order to provide a place to accommodate the force/torque sensor 500. The force/torque sensor 500 is offset from a central axis 211 of the main body 220, as shown in the figures. The off-center mounting provides several functions. First, it allows the sensor 500 to be mounted outside the electron beam pathway so that the electron beam is not obstructed. Further, the off-center mounting helps to accentuate torque readings, so that sensor 500 is able to sense variations in torque values with enhanced sensitivity.

FIG. 52 is an exploded view of sub-assembly 96 of FIG. 49. Sub-assembly 96 generally includes an upper mounting plate or output flange 210 used to attach sub-assembly 96 to upstream components. Mounting plate 210 includes a central aperture 217 centered about axis 211, an upper or upstream face 214, and a lower or downstream face 216.

Main body 220 includes a central aperture 218 that can house a central core and mirror assembly through which the ebeam 16 (FIG. 1) travels. Main body 220 further includes a recessed area or pocket 502 in which the force/torque sensor 500 is mountable. Recessed area 502 includes a curved support wall 504 and a base portion 506. Base portion 506 further includes multiple apertures 508 configured to accept fasteners 510 that will extend from an underside of base portion 506 into corresponding holes in the bottom of force/torque sensor 500 to secure the force/torque sensor 500 to the main body 220 from the bottom. The upper mounting plate 210 may similarly include multiple apertures 512 configured to accept fasteners 514 that will extend from an top side of upper mounting plate 210 into corresponding holes in the top of force/torque sensor 500 to secure the force/torque sensor 500 to the upper mounting plate 210 from the top.

Other features of the coupling system 95 described above relative to embodiments described herein can likewise be included in this embodiment that includes at least one force/torque sensor 500. For example, the coupling system 95 can include a stator ring mounted to main body 220 and a rotor ring mounted to the second subassembly 98. A rotary encoder may be incorporated into coupling system 95 so that relative rotation between sub-assembly 96 and sub-assembly 98 can be automatically monitored and measured. In addition, coupling system 95 can include an annular ring bearing that rotatably couples sub-assembly 96 to sub-assembly 98, which allows sub-assembly 96 to rotate relative to sub-assembly 98. In practice, sub-assembly 96 is attached to a larger assemblage of upstream components of unit 26 (FIG. 2), while second sub-assembly 98, the applicator 86, and shield 88 are rotatable on demand about axis 211.

In general, the force/torque sensors 500 used for a particular application for the devices described herein include an electronic device that is designed to monitor, detect, and/or read force and/or torque associated with the rotary coupling system 95 and hence the system 10. In some modes of practice, the force/torque sensors used with embodiments described herein may include a transducer that can communicate with interface electronics via electronic connections (e.g., cables). The force/torque sensors may include electronics integrated into the body of the device, and/or may include external hardware. The force/torque sensors may utilize strain gages to sense forces, such as silicon strain gages. Certain force/torque sensors can be designed to provide noise immunity and/or allow high overload protection. Suitable force/torque sensors can include those that are commercially available from ATI Industrial Automation of Apex, North Carolina, for example.

FIG. 57 schematically shows an illustrative method 600 of using System 10 of FIGS. 48 to 56 to detect a collision. In step 602, sensor 500 is provided that is coupled to the electron beam radiation system in a manner effective to sense readings indicative of at least one of force and/or torque encountered by the electron beam system. The sensor 500 measures at least one of torque and or force and transmits the torque and/or sensor readings to controller 38. The torque and/or force data can be read at any suitable rate. In some embodiments, data is read at a rate of 2 Hz to 200 Hz, preferably 2 Hz to 200 Hz, more preferably 2 Hz to 120 Hz. The data may be read during all or a portion of the time during the course of docking, treatment, and post treatment until the patient has left. Desirably, the data is read continuously during the course of docking, treatment, and patient leaving the treatment station. Data desirably is read during the normal state (no collision detected), at the time of collision detection, after the collision has occurred while the system 10 is still in a collision state, and post-collision (if any) after the system 10 has returned to a normal (non-collision state). In some instances, a treatment may be stopped only temporarily if a collision is detected at least until normal status is restored and the treatment continues. In such a case, data gathering may continue without interruption to help identify when a normal state is restored. In other instances, data gathering may be stopped if a collision is detected.

A hardware processor (not shown) in controller 38 is configured to execute steps to follow instructions stored in at least one controller memory. Overall, these steps allow controller 38 to detect collisions and to direct appropriate follow up action. In step 603, the collision status is set to "No," meaning that the system is in normal operating mode. This is the starting collision status in this particular mode of practice. In other modes, the initial collision status can be set to YES until a collision free status is confirmed.

In step 604, the instructions cause controller 38 to receive the data readings and store them in at least one memory (not shown). In some modes of practice, the gathered data may be stored in at least one memory. The historical data may be stored for archival purposes and/or to be used in comparisons to help evaluate collision status. The mode of practice shown in FIG. 57 makes such comparisons after a collision is detected. The amount of historical data to use for a comparison can vary over a wide range. Generally, fewer historical data points are less accurate due to factors such as noise that may cause a fluctuation in a rate of change profile. A greater number of historical data points could be used, but this can be more accurate, but this may require more memory and/or may smooth data too much so that detection is not as rapid as might be desired. Balancing these concerns, using historical data including from at least 10 to 10,000, preferably 20 to 500, more preferably 50 to 200, and even more preferably about 100 data readings would be sufficient. In some embodiments, a useful historical data window to be used for comparisons spans data points obtained in a time period from 0.5 to 10 seconds, preferably 1 to 5 seconds, or even about 2 seconds.

For example, in a typical docking operation, the electron beam generation unit 26 of a system 10 and a target site 12 (e.g., treatment surface of a patient) are moved relative to each other to achieve proper docking, e.g., so that the end of an applicator 86 and/or field defining shield 88 is positioned at a predetermined distance from a target site 12 (soft docking) or in contact with the target site 12 (hard docking) to allow for treatment of the patient.

In step 606, the instructions cause controller 38 to use the readings to determine profile information that is indicative of the rate of change of the sensed readings as a function of time. Depending on whether the sensed readings include torque and/or force data, the profile information may be indicative of the rate of change of the corresponding, sensed torque or force readings.

In step 608, the instructions cause controller 38 to use the profile information in an evaluation to evaluate a collision status of the system 10. The collision status includes one or more determinations relating to whether the system 10 is in a normal state or whether a collision occurred. If no collision is detected, then the collision status remains "No" as shown by step 614. Path 618 shows that the system continues to follow steps 604, 606, 608, 610, and 614 so long as the collision status remains "No." If the evaluation in step 608 shows that the collision has occurred or is still in a "Yes" state, then the collision status is set or maintained, as the case may be, as "Yes" in step 612.

As a consequence of the system being in a "Yes" state, pathway 616 shows that at least three sets of instructions are carried out. First, the system continues to practice steps 604, 606, and 608 to take readings and evaluate collision status. In parallel, follow up action responsive to a detected collision is taken in step 620. Also in parallel, program instructions compare the current readings of force and/or torque to the historical, pre-collision values of force and torque to determine if the current readings match the historical readings. If the current readings sufficiently match the historical readings in step 626, the system determines that the collision event has ended and returns the system to step 614 and changes the system collision status to "No." Additionally, the program instructions cause the system to take desired follow up action in step 630 as appropriate to the collision event being over. Such follow up can include a signal sent to an operator, restoration of the docking or treatment procedure, or the like. If the current readings remain sufficiently different from the historical readings, then the system determines that the collision event is ongoing in step 619 and the system is returned to pathway 616.

The cycles of steps in method 600 are repeated to continuously monitor, process, evaluate, and take follow up action as appropriate during one or more desired time periods. Advantageously, method 600 uses the rate of change of force and/or torque to help detect a collision event as well as actual force and/or torque values to help evaluate whether a collision event is ongoing or has ended.

Figure 58A:
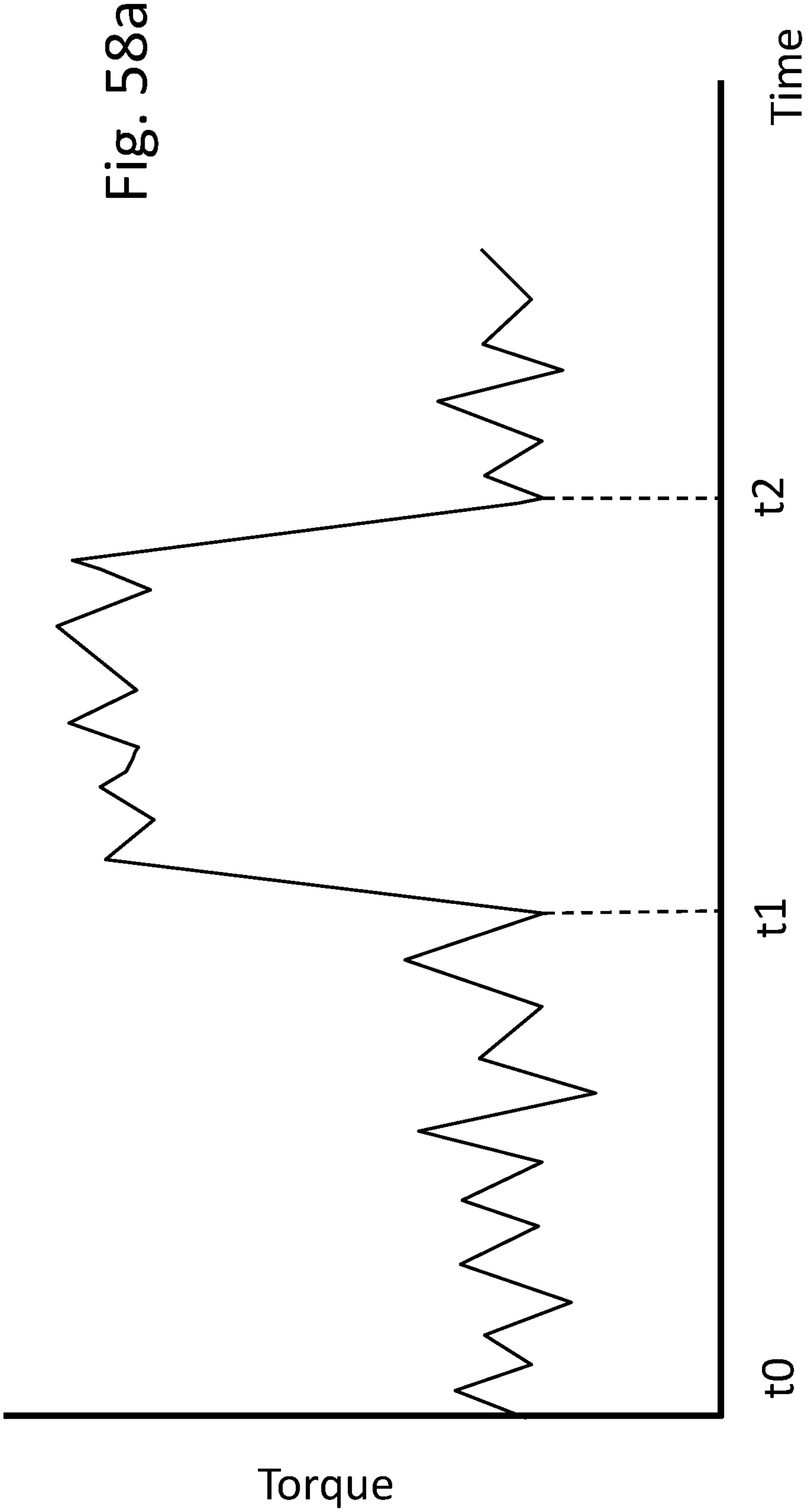
FIG. 58*a* schematically shows how torque readings can change over time regardless of whether a collision has occurred, showing that relying only on actual force and torque values is not an accurate way to detect collisions under a wide range of circumstances.

FIG. 58*a* schematically shows how torque readings can change over time regardless of whether a collision has occurred, showing that relying only on actual force and torque values is not an accurate way to detect collisions under a wide range of circumstances FIG. 58*a* shows this profile in the context of a hard docking procedure. The same torque characteristics also could be observed with respect to soft docking procedures. At the time t0, docking begins. Torque is monitored starting at time t0. In the time interval between t0 and t1, the torque readings are at a relatively low level. The torque readings have some up and down variation due to signal noise, which is normal. At time t1, the torque values suddenly increases to a higher level and continue at that higher level until time t2. At time t2, the torque values drop to a lower level substantially matching the values in the time period from t0 to t1.

Unfortunately, the torque profile in FIG. 58*a* is not useful on its own to detect collision status. For example, it cannot be determined if one or both of the elevation in torque values at time t1 or the drop in torque values at time t2 is associated with a collision or not. The changes in the profile also could be due to a change in orientation of the equipment rather than a collision.

Figure 58B:
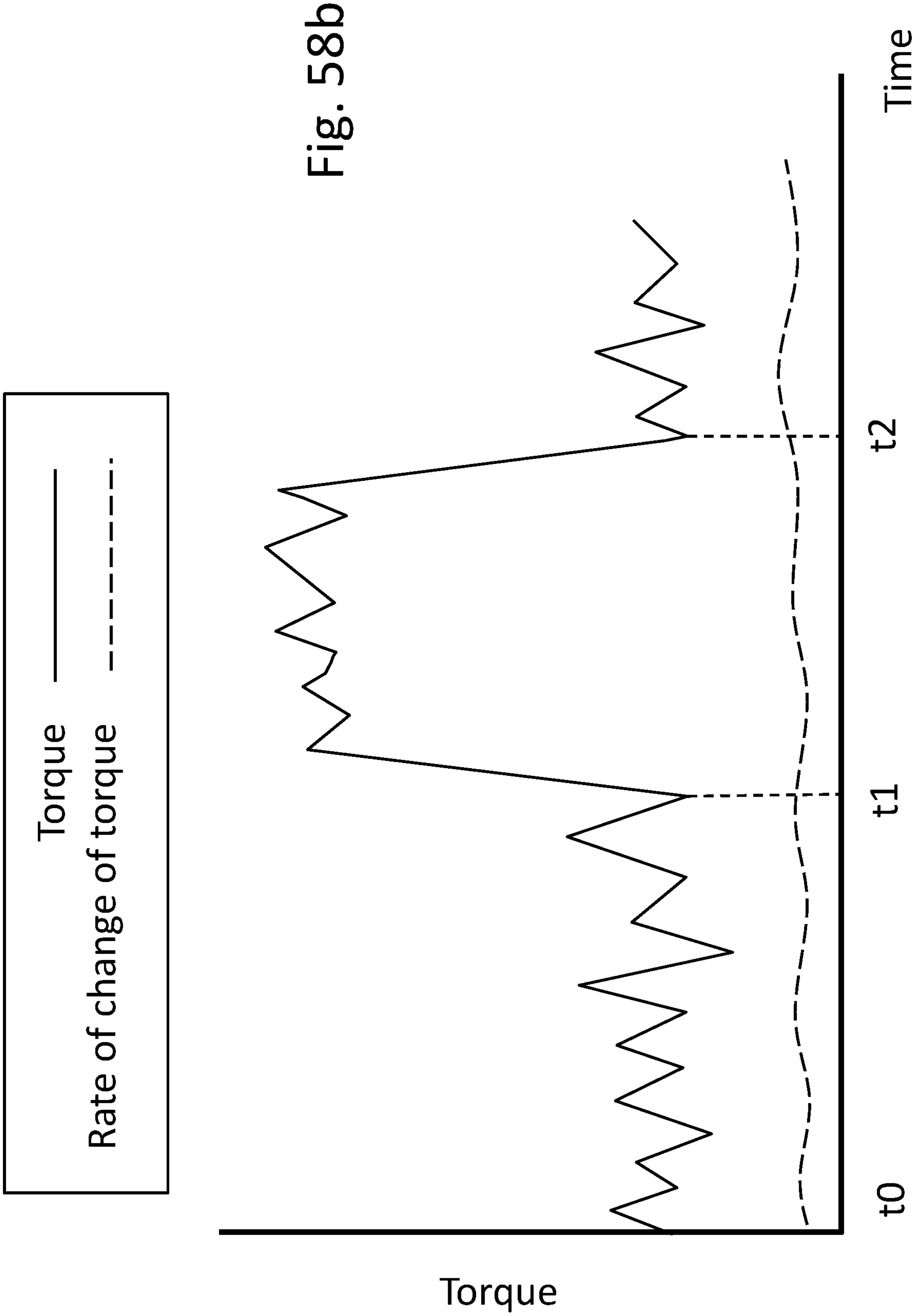
FIG. 58*b* schematically shows how rate of change of torque values superposed on the force and/or torque readings of FIG. 58*a* confirms that no collision has occurred.

FIG. 58*b* schematically shows how rate of change of torque values (dT) superposed on the force and/or torque readings of FIG. 58*a* confirms that no collision has occurred in FIG. 58*a*. The rate of change profile for torque is low and relatively steady and does not show any positive or negative spikes at any time, including at times t1, t2, or other times.

Figure 58C:
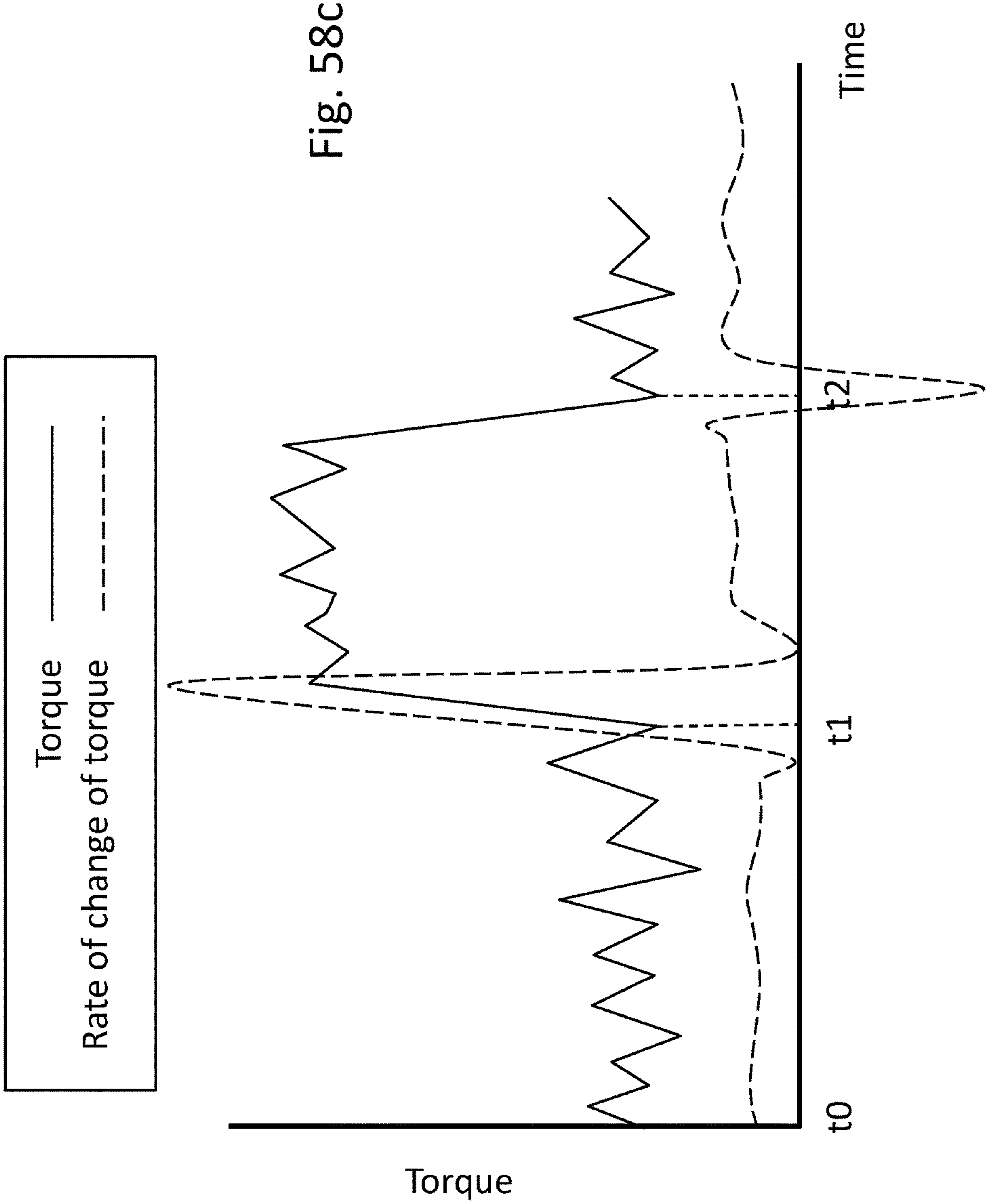
FIG. 58*c* schematically shows how rate of change of torque values superposed on the force and/or torque readings of FIG. 58*a* confirms that a collision has occurred.

FIG. 58*c* schematically shows an alternative scenario where the rate of change of torque values (dT) superposed on the force and/or torque readings of FIG. 58*a* confirms that a collision has occurred at time t1. FIG. 58*c* shows how the rate of change profile is relatively low from time t0 to time t1. At time t1, a sharp upward spike in the rate of change profile occurs to signal a collision occurred. In combination with the spike in the rate of change profile, the elevated values for torque from time t1 to time t2 indicate that the collision event is still occurring up to time t2. A comparison of the torque values from the period t1 to t2 to those in the time period from t0 to t1 confirms that the torque values are elevated. At time t2, the rate of change value shows a negative spike after which torque values are a substantial match for the pre-collision torque values. This indicates that the collision event ended at time t2 and appropriate follow up can be taken, e.g., system operations can be restored.

The specification for when a positive or negative spike in the rate of change profile signals a collision can be defined in a variety of ways. According to one approach, the specification is in the form of a normal state range defined as a such that a rate of change profile of torque above or below the range indicates a collision. A collision is detected generally when there is an abrupt elevation or reduction in the rate of change associated with the measured force and/or torque values. At the same time, the actual values of force and torque monitored after a collision is detected can be compared with historical values to evaluate whether a collision is still occurring. When current measurements exceed the historical values by a suitable specification, an ongoing collision is indicated. Similarly, when current measurements are consistent with pre-collision, historical values according to a suitable specification, a restoration to the non-collision state is indicated.

In response to the collision detection, controller 38 can take a variety of follow up actions. Follow up action may include a variety of automated and/or manual responses such as one or more of stopping motion of the electron beam machine, issuing a collision alarm to an operator, reversing motion of the machine, stopping motion of the patient support structure, stopping power supply to the patient support structure, continuing to monitor the rate of change profile to detect if and when the collision status changes again, and taking follow up action of the collision state changes again.

FIGS. 58*b* and *c* show how the force or torque readings are still read during the collision state from t1 to t2 and afterward in order to continue to monitor the rate of change profile and the actual values of the torque and/force. This allows the system to evaluate information such as when the collision state ends, whether the collision state gets worse such as if the rate of change profile elevates again, or the like. Also, the sensed readings and rate of change information may be stored in a suitable memory of the system so that the historical readings may be accessed to compare to later or even other historical readings. Such comparisons with respect to later readings can be used to help determine whether the collision state is maintained or has ended. Such comparisons also may be made to determine if a real collision has occurred or not. Such comparisons may be made among historical readings to review a historical procedure.

In FIG. 58*c*, note that the rate of change profile increased significantly at time t1 as compared to the pre-collision state from time period t0 to t1. When a collision is detected at time t1, controller 38 desirably generates and transmits control signals causing the motor(s) (or other translation mechanisms) moving the patient and/or the electron beam generation unit to stop. In a situation where a patient is positioned on a motorized table, for example, controller 38 will output control signals that cause the table structure 580 to stop. The motion of the patient supporting structure 580 that is stopped may include one or more of vertical motion (z axis), horizontal motion (x and/or y motion), angled motion (pitch, roll and/or yaw), and/or other directional motion as needed for proper patient positioning. It is alternatively or additionally possible that a detected collision event will cut the power provided to the supporting structure 580 to stop the motion.

Often, therefore, controller 38 would cause the system 10 to physically stop moving upon detecting a collision, yet until the stop signal is acted upon, the machine is still being driven in an attempt to continue with the movement occurring up to the collision. This continued driving could cause the sensed torque and/or force readings to remain high. Hence, the force and/or torque generally do not restore to normal levels upon a collision unless the driving force causing the collision is stopped.

FIGS. 59 to 62 show data from experiments in which the rotary coupling system of an IntraOp Mobetron electron beam machine is fitted with an off-center force and torque sensor. Force and torque data was sensed as the machine was caused to have lateral or gantry collisions. If the x-y plane is defined as the horizontal plane, the y-axis is defined as the horizontal axis from the front to the back of the machine, the x-axis is defined as the horizontal axis side to side, and the z axis is the vertical axis perpendicular to the horizontal plane, then a lateral collision refers to a collision occurring as the machine is moved laterally parallel the x-y plane. A gantry collision refers to a collision occurring as the machine rotates about the y-axis, e.g., between a vertical position and a horizontal position. The effect of gantry rotation is to affect the angle at which the main axis of the machine is angled with respect to the vertical and horizontal planes.

Figure 59:
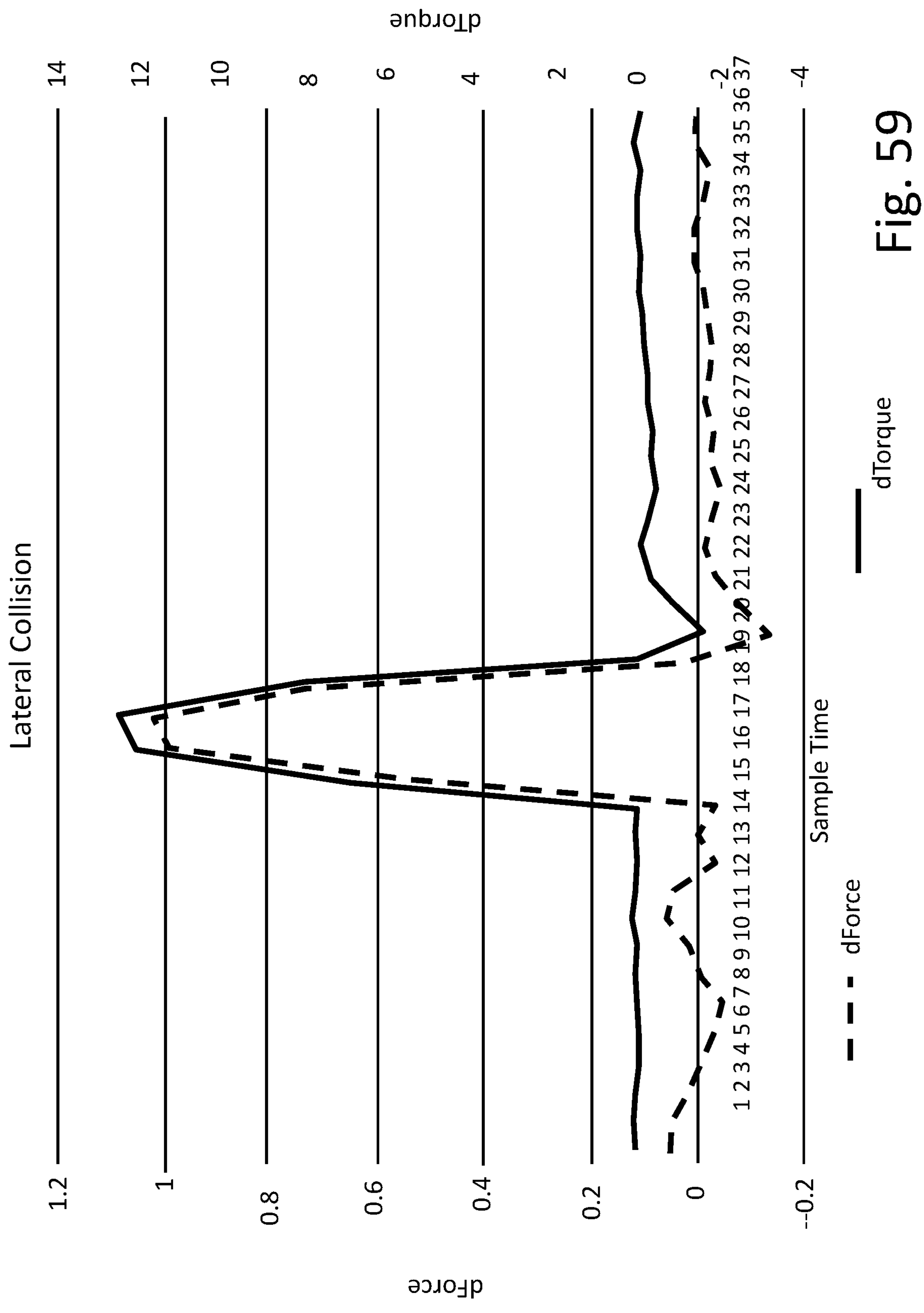
FIG. 59 illustrates how spikes in the rates of change of force (dF) and torque (dT) occur upon a lateral collision.

FIG. 59 illustrates an experiment in which force and torque data is collected as the electron beam machine is caused to experience a lateral collision. The corresponding magnitudes of the rate of change of force (dF) and torque (dT) are plotted as a function of time. FIG. 59 illustrates how spikes in the rates of change of force (dF) and torque (dT) occur upon a lateral collision. Note that both rate profiles show a significant upward spike at the same time to provide a signal that a collision has occurred. In this example, both profiles detect a collision event at the same time, showing comparable sensitivity to sensing a collision. Each profile provides a strong signal in the form of a spike that is easy to distinguish from the pre-collision state. After the collision is detected, the spike quickly dissipates. This does not necessarily mean that the collision event is over. As described herein, the post-collision force and torque values can be compared to historical values to help determine when the collision event has ended. Specifically, post-collision values that substantially match the pre-collision values indicate the end of a collision event.

Figure 60:
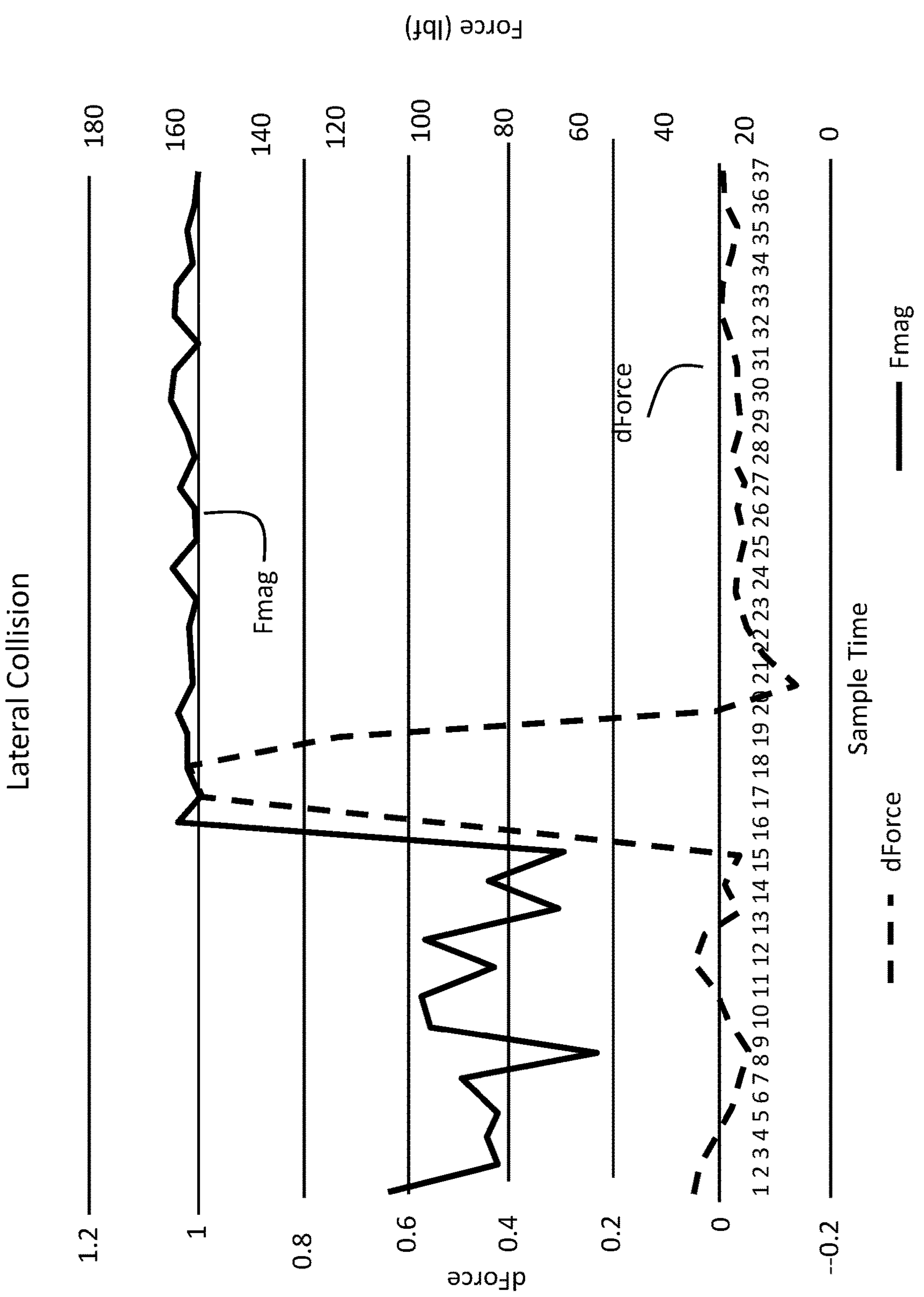
FIG. 60 shows how the rate of change of force (dF) and the magnitude of sensed force (Fmag) are affected by a collision event that continues for a period of time after the start of the collision, wherein the elevated force values after the collision stay elevated relative to the pre-collision values to indicate that the collision event is ongoing.

FIG. 60 illustrates an experiment in which force data is collected as the electron beam machine is caused to experience a lateral collision and the corresponding force values and rate of change values continue to be monitored after the onset of the collision. The force values (Fmag) and the corresponding magnitude of the rate of change of force (dF) are plotted as a function of time. FIG. 60 shows how the rate of change of force (dF) and the magnitude of sensed force (Fmag) are affected by a collision event that continues for a period of time after the start of the collision. A large spike in the rate of change profile signals a collision event. At the same time, the force values (Fmag) also elevate at the time of the collision. The post-collision, elevated force values remain elevated relative to the pre-collision values to indicate that the collision event is ongoing. In this case, both the rate of change values and the actual values of force help to evaluate the collision status over time.

Figure 61:
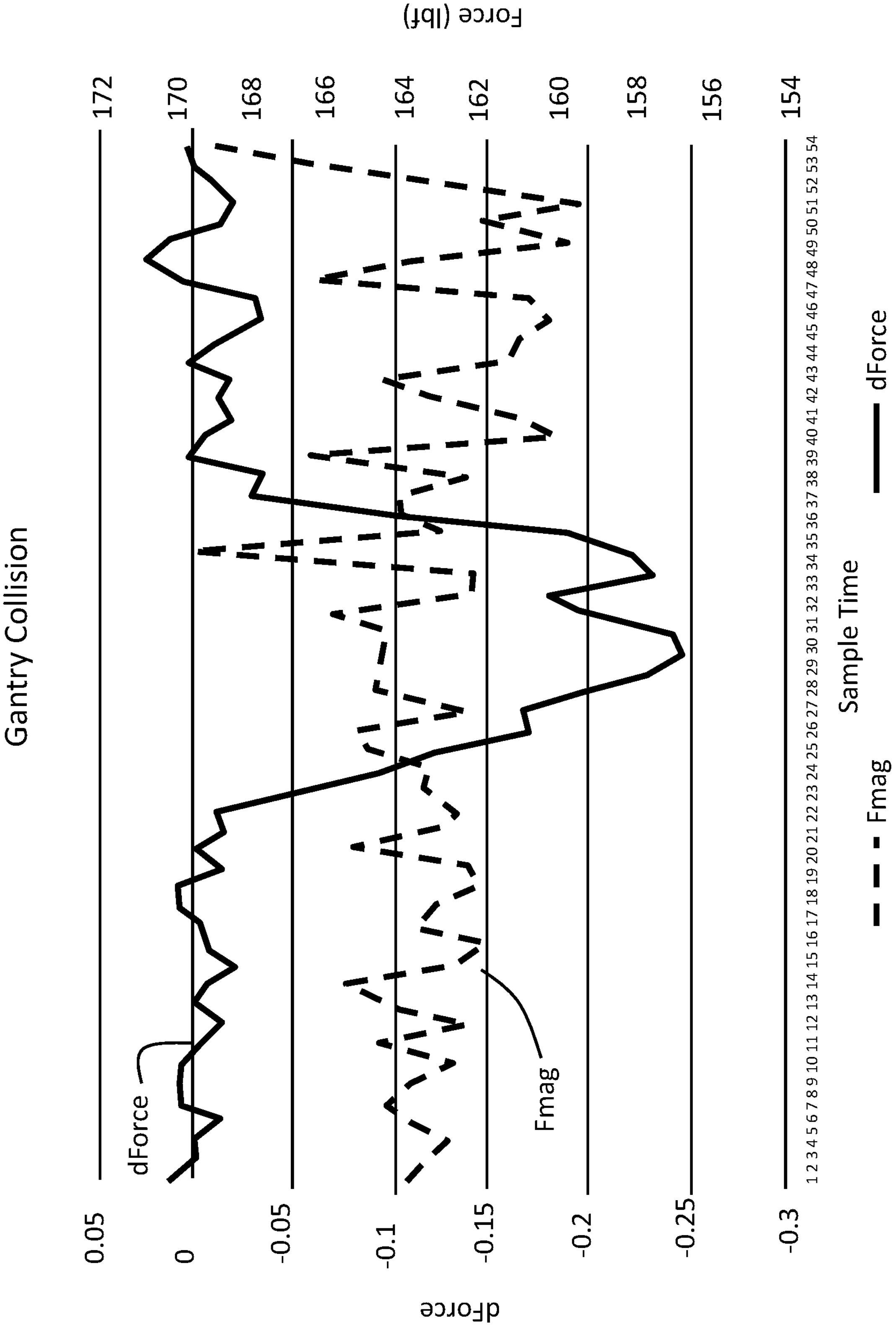
FIG. 61 shows how a negative spike in the rate of change of force (dF) shows that a collision occurred even though the magnitude of force values (Fmag) do not show a collision.

FIG. 61 illustrates an experiment in which force data is collected as the electron beam machine is caused to experience a gantry collision and the corresponding force values and rate of change values continue to be monitored after the onset of the collision. The force values (Fmag) and the corresponding magnitude of the rate of change of force (dF) are plotted as a function of time. FIG. 61 shows how a negative spike in the rate of change of force (dF) shows that a collision occurred even though the magnitude of force values (Fmag) do not show a collision. This shows how actual values of force or torque may not be helpful to detect some kinds of collisions, yet the rate of change profile is quite sensitive to the collision. Also, this illustrates a collision for which the collision caused a downward spike in the rate of change profile. This occurs, for example, where the collision might lift the equipment to reduce the force of gravity.

Figure 62:
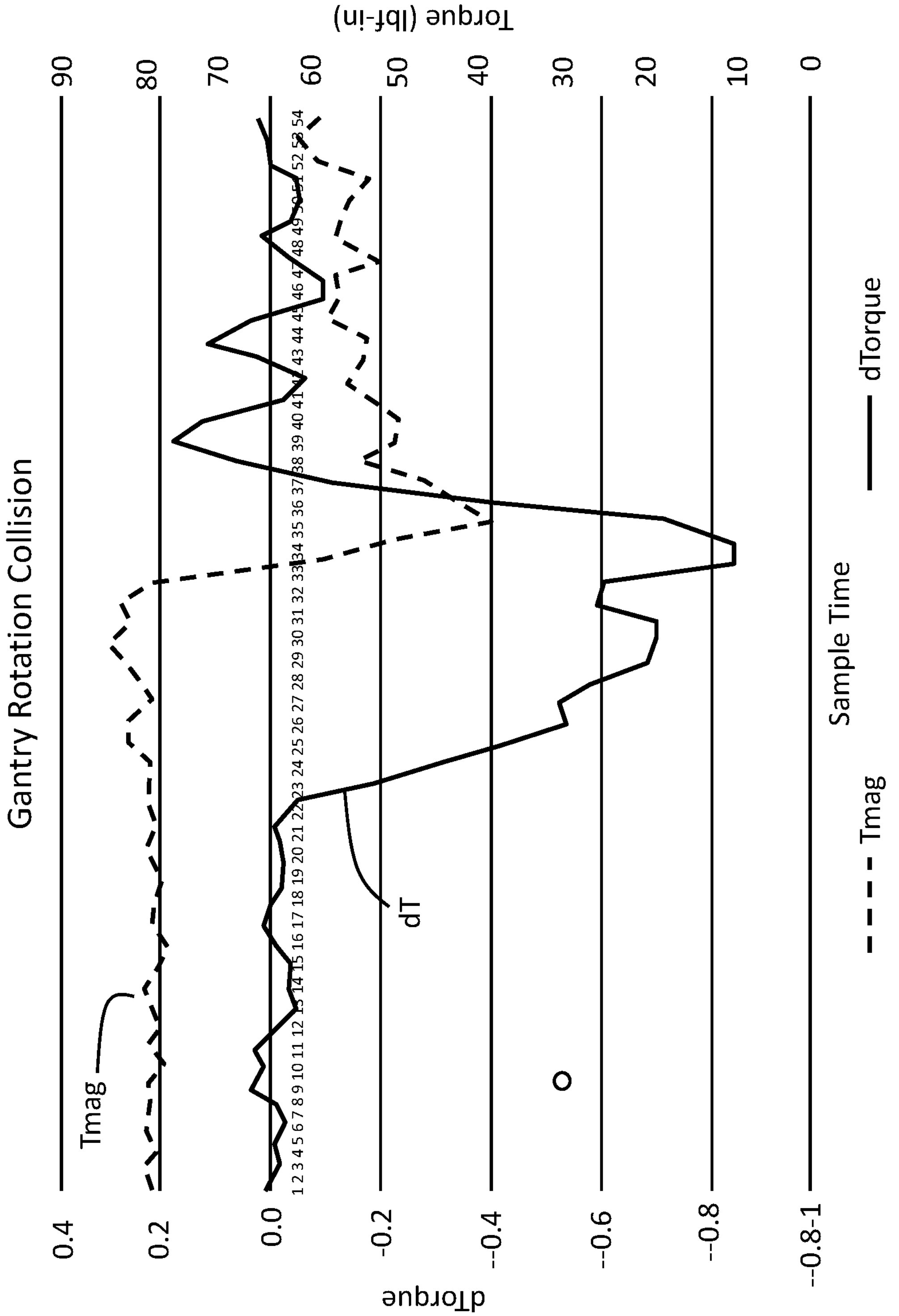
FIG. 62 shows how both the rate of change of torque (dT) and the magnitude of torque values are affected by a collision, but the rate of change of torque profile provides an earlier and larger collision signal.

FIG. 62 illustrates an experiment in which torque data is collected as the electron beam machine is caused to experience a gantry collision and the corresponding torque values and rate of change values continue to be monitored after the onset of the collision. The torque values (Tmag) and the corresponding magnitude of the rate of change of torque (dT) are plotted as a function of time. FIG. 62 shows how both the rate of change of torque (dT) and the magnitude of torque values are affected by the collision, but the rate of change of torque profile provides an earlier and stronger collision signal. In this circumstance, both the rate of change and the actual values of torque provide a collision signal. However, the discussion above explains and shows how actual values of torque or force might fail to give a signal upon a collision event, whereas the rate of change profile is a more reliable and more sensitive indicator of a collision.

As an aspect of the present invention, it has been discovered that changing the applicator 86 and/or shield 88 also can cause positive or negative spikes in the rate of change profiles of force or torque to occur. It would be desirable to be able to swap, maintain or otherwise service components without triggering a collision alarm. Fortunately, the spikes occurring when components are changed, maintained, or otherwise serviced are much higher than the spikes associated with a collision. The collision spikes associated with components, therefore, are easy to distinguish from collision spikes based on the significant difference in their respective magnitudes. Consequently, a collision alarm can be based on a spike being large enough to exceed a threshold and yet small enough to be distinguished from component servicing spikes. In short, a collision could be indicated if a rate of change spike exceeds the threshold but is smaller than a ceiling set so that the magnitudes of the component spikes are above the ceiling.

To summarize, monitoring information indicative of the rate of change of at least one of force and torque provides accurate, fast detection of a collision event. If the rate of change profile shows a sudden increase up or down, then an event impacting collision status is detected.

As discussed above, a variety of follow up responses may be taken responsive to detection of a collision event. Some responses to a collision may cause a power cut off or other actions for which it might take some time to reverse and restore operation status when a collision state has ended. Yet, there are some proper modes of operation that cause the rate of change of force and torque readings to elevate even though a collision has not occurred. It would be desirable for the system to recognize such proper mode of operation to avoid the delay associated with restoring operation status after a true collision detection. One such proper mode of operation occurs when the switch is activated (manually or automatically) to unlock and allow the rotary coupling system to rotate. It would be highly desirable to recognize activation of this switch so that the machine, the table, or other equipment is not stopped, powered off, or otherwise change in a way that would cause undue delay to continue docking, treatment, or other process.

System 10 shown in FIGS. 48-56 includes optional but preferred functionality to allow switch activation to be detected in order to avoid a collision alarm. In certain embodiments discussed above, a rotary locking and release mechanism 236 and rotary indexing system 238 are integrated with the main body 220. As described with regard to exemplary FIGS. 29, 31, 35, 39, and 42-44, the rotary locking and release mechanism 236 includes button actuated locking device 432 mounted onto main body 220 of upper sub-assembly 96 and the ring 348 and detent features 349 on the lower sub-assembly 98. The ring 348 and detent features 349 play a role both for indexed rotation as well as for rotational locking functionality. However, when such a rotary locking and release mechanism 432 is incorporated into the main body 220 of the embodiment of FIGS. 48-50, it is possible that actuating the button actuated locking device 432 and/or the associated rotation of the rotary coupling system 95 could cause the force/torque sensor 500 to measure an elevation in the rate of change of at least one of force or torque. The elevated rate of change profile(s) could exceed the normal state threshold so falsely indicate that a collision has occurred. This would then cause collision follow up action to be taken, such as causing the movement of a patient and/or electronic beam generation unit relative to each other to be stopped, even though an actual collision has not occurred.

In order to prevent the force/torque sensor 500 from registering a collision caused by the activation of the actuating the button actuated locking device 432 or associated rotation of rotary coupling system 95, an alternative embodiment of a rotary locking and release mechanism 552 as is illustrated in FIGS. 53-56 may be mounted onto the main body 220 in place of the mechanism 436.

As shown in these Figures, mechanism 552 includes a housing 554 and locking teeth 556 projecting from the underside of the housing 554. Teeth 556 function in the same manner as teeth 436 described above. Mechanism 552 further includes button mechanism 536. Switch 560 is at least partially positionable within the housing 554 and the button mechanism 536. The switch 560 can include wires (not shown) that extend through a groove 562 in housing 554 for communication with control 38 The wires would carry a signal to indicate when the locking device 552 is actuated to unlock the rotary coupling system 95 to allow rotation. A proximal end 555 of the switch 560 extends from the housing 554. Proximal end 555 is in the form of a plunger that is depressed if the switch 560 is pressed against an adjacent surface. The switch 560 may be deployed within the housing 554 in such a way that the distance it needs to move to be activated (i.e., the trigger distance) can be adjusted. In one example, the outer surface of the switch 560 has a threaded surface that mates with a threaded inner surface of the housing. This helps hold the switch 560 in position relative to the housing 554 so that pressing the button mechanism 536 causes proximal end 555, in view of its plunger configuration, to be depressed.

In use, pushing the button mechanism 536 accomplishes at least two functions. First, button actuation causes the teeth 556 to disengage from the ring 348 (discussed above with respect to locking mechanism 432). This unlocks the rotary coupling mechanism 95, allowing rotation to occur. Second, in one mode of practice, button actuation presses the proximal end 555 of the switch 560 against an adjacent surface such as a surface of the main body 220. When the proximal end 555 of switch 560 presses against this surface, proximal end 555 in the form of a plunger is depressed. This activates the switch 560 to send a signal to the control system 38 to indicate that button actuation has occurred. Control system 38 includes program instructions that receive the button actuation signal and use that to provide an evaluation that no collision exists and therefore no collision follow up action should be taken.

The foregoing detailed description has been given for clarity of understanding only. No unnecessary limitations are to be understood therefrom. The invention is not limited to the exact details shown and described, for variations obvious to one skilled in the art will be included within the invention defined by the claims.

What is claimed is:

1. An electron beam radiation system that emits an electron beam, comprising:

a) an electron beam unit having a unit outlet, wherein the electron beam unit produces the electron beam and emits the electron beam from the unit outlet to a target site;

b) at least one sensor capable of sensing at least one of force and torque, wherein the sensor is coupled to the electron beam unit in a manner effective to detect at least one of force and/or torque readings associated with the electron beam unit; and c) a control system comprising at least one hardware processor operatively coupled to at least one memory, wherein the hardware processor is configured to execute steps comprising the following instructions stored in the at least one memory:

i) receiving the force and/or torque readings from the sensor;

ii) smoothing the force and/or torque readings;

iii) using the smoothed force and/or torque readings to determine rate of change information indicative of a rate of change of at least one of the force and/or torque readings as a function of time; and iv) using the rate of change information to determine a collision status of the electron beam unit.

2. The system of claim 1, wherein the electron beam unit is an electron beam linear accelerator (LINAC) machine, and wherein the electron beam has a linear electron beam pathway.

3. The system of claim 2, wherein the electron beam unit is self-shielded.

4. The system of claim 2, wherein the at least one sensor is mounted outside the linear electron beam pathway.

5. The system of claim 1, wherein the electron beam unit comprises a collimator and a rotary coupling system downstream from the collimator, and wherein the sensor is incorporated into the rotary coupling system.

6. The system of claim 5, wherein rotary coupling system includes an upstream sub-assembly and a downstream sub-assembly rotatably coupled to the upstream sub-assembly, and wherein the sensor is incorporated into the upstream sub-assembly.

7. The system of claim 1, wherein the at least one sensor senses torque readings.

8. The system of claim 1, wherein the at least one sensor senses force readings.

9. The system of claim 1, wherein the at least one sensor senses torque and force readings, and wherein the instructions stored in the at least one memory further comprise smoothing each of the force and torque readings.

10. The system of claim 1, wherein the electron beam unit has a central axis, and wherein the at least one sensor is offset from the central axis.

11. The system of claim 1, wherein the instructions further comprise, if a collision is detected, controlling the power of a support structure.

12. The system of claim 11, wherein the instructions further comprise, if a collision is detected, stopping relative motion between the support structure and the electron beam unit.

13. The system of claim 1, wherein the instructions further comprise storing the sensed readings in a memory.

14. The system of claim 1, wherein the smoothed force and/or torque readings comprise a moving average of 3 or more sensed torque or force readings, respectively.

15. The system of claim 1, wherein the instructions of c(iv) comprise using a Savitzky-Golay filter.

16. The system of claim 1, wherein the instructions of c(iv) comprise using a change in a magnitude of the rate of change information to determine that a collision occurred.

17. The system of claim 1, wherein the at least one sensor is configured to sense force and/or torque readings at a rate in the range from 2 Hz to 200 Hz.

18. The system of claim 1, wherein the instructions further comprise:

i) storing pre-collision, sensed torque and/or force readings in a memory to provide historical readings of force and/or torque readings;

ii) after detecting a collision, comparing sensed torque and/or force readings to the historical readings of torque and/or force; and iii) after detecting the collision, using the comparison to determine if the collision has ended.

19. The system of claim 1, wherein the instructions of c(iv) comprise determining if the rate of change information is in a normal range.

20. The system of claim 19, wherein a collision is detected in the instructions of c(iv) when the rate of change information is above or below the normal range.

21. The system of claim 1, wherein the instructions of c(i) comprise sensing torque readings, and wherein the instructions further comprise, after a collision is detected:

i) continuing to perform step c); and ii) comparing a plurality of sensed torque values to a plurality of historical torque values to help determine if the collision has ended.

22. The system of claim 1, wherein the instructions of c(i) comprise sensing force readings, and wherein the instructions further comprise, after a collision is detected:

i) continuing to perform step c); and ii) comparing a plurality of sensed force values to a plurality of historical force values to help determine if the collision has ended.

23. The system of claim 1, wherein the target site is in or on a body or body parts of a patient, and wherein the instructions further comprise:

i) docking the electron beam unit with respect to the patient supported on a motorized table; and ii) after a collision is detected during docking, stopping relative motion between the patient and the table.

24. The system of claim 1, wherein the target site comprises a surface.

25. A method of detecting a collision status of an electron beam radiation unit that emits an electron beam, comprising the steps of:

a) providing an electron beam unit having a unit outlet, wherein the electron beam unit produces the electron beam and emits the electron beam from the unit outlet;

b) providing at least one sensor that measures at least one of torque and/or force, wherein the sensor is coupled to the electron beam radiation system in a manner effective to sense readings indicative of at least one of force and/or torque encountered by the electron beam radiation system;

c) using the sensor to sense force and/or torque readings associated with the electron beam unit;

d) smoothing the sensed force and/or torque readings;

e) using the smoothed readings to determine rate of change information indicative of a rate of change of at least one of the torque and/or force readings as a function of time; and f) using the rate of change information to determine a collision status of the electron beam radiation unit.

* * * * *